United States Patent
Arzi et al.

(10) Patent No.: US 12,171,786 B2
(45) Date of Patent: Dec. 24, 2024

(54) USE OF MESENCHYMAL STEM CELLS FOR THE TREATMENT OF INFLAMMATION

(71) Applicant: The Regents of the University of California, Oakland, CA (US)

(72) Inventors: Boaz Arzi, Davis, CA (US); Emily Mills Ko, Davis, CA (US); Dori L Borjesson, David, CA (US)

(73) Assignee: The Regents of the University of California, Oakland, CA (US)

( * ) Notice: Subject to any disclaimer, the term of this patent is extended or adjusted under 35 U.S.C. 154(b) by 1302 days.

(21) Appl. No.: 15/765,622

(22) PCT Filed: Oct. 5, 2016

(86) PCT No.: PCT/US2016/055529
§ 371 (c)(1),
(2) Date: Apr. 3, 2018

(87) PCT Pub. No.: WO2017/062475
PCT Pub. Date: Apr. 13, 2017

(65) Prior Publication Data
US 2021/0393697 A1 Dec. 23, 2021

Related U.S. Application Data

(60) Provisional application No. 62/237,115, filed on Oct. 5, 2015.

(51) Int. Cl.
*A61K 35/28* (2015.01)
*C12N 5/0775* (2010.01)
*G01N 33/50* (2006.01)
*A61K 35/12* (2015.01)

(52) U.S. Cl.
CPC ............ *A61K 35/28* (2013.01); *C12N 5/0667* (2013.01); *G01N 33/5047* (2013.01); *A61K 2035/124* (2013.01); *G01N 2800/52* (2013.01)

(58) Field of Classification Search
CPC .................................................... A61K 35/28
See application file for complete search history.

(56) References Cited

U.S. PATENT DOCUMENTS

| | | |
|---|---|---|
| 2007/0128174 A1 | 6/2007 | Kleinsek et al. |
| 2007/0269481 A1 | 11/2007 | Li et al. |
| 2009/0054528 A1 | 2/2009 | Whiteford |
| 2010/0254953 A1 | 10/2010 | Honmou et al. |
| 2011/0091430 A1 | 4/2011 | Dzau et al. |
| 2011/0117064 A1 | 5/2011 | Westenfelder |
| 2012/0021414 A1 | 1/2012 | Shen-Orr et al. |
| 2013/0029292 A1 | 1/2013 | Mar et al. |
| 2013/0164267 A1 | 6/2013 | Lin et al. |
| 2014/0072537 A1 | 3/2014 | Kimbrel et al. |
| 2016/0199414 A1 | 7/2016 | Arzi et al. |

FOREIGN PATENT DOCUMENTS

| | | | |
|---|---|---|---|
| EP | 1 421 957 A1 | 5/2004 | |
| WO | WO-2005/093044 A1 | 10/2005 | |
| WO | WO-2008/036374 A2 | 3/2008 | |
| WO | WO 2009/152084 A2 | 12/2009 | |
| WO | WO-2012/142569 A2 | 10/2012 | |
| WO | WO-2012/1142569 A2 | 10/2012 | |
| WO | WO-2015034660 A1 * | 3/2015 | ............. A61K 35/28 |
| WO | WO-2017/062475 A1 | 4/2017 | |

OTHER PUBLICATIONS

Litster A, Lin JM, Nichols J, Weng HY. Diagnostic utility of CD4%:CD8 low% T-lymphocyte ratio to differentiate feline immunodeficiency virus (FIV)-infected from FIV-vaccinated cats. Vet Microbiol. Jun. 4, 2014;170(3-4):197-205. (Year: 2014).*
Wang et al. (1993, Clin. Exp. Immunol., vol. 94, pp. 297-305). (Year: 1993).*
Hof-Nahor et al. (2012, J. Cell Sci., vol. 125, pp. 4640-4650) (Year: 2012).*
Bartholomew et al., "Collection of equine cord blood and placental tissues in 40 Thoroughbred mares", Equine Veterinary Journal, 2009, vol. 41, No. 8 (pp. 724-728).
Beggs et al., "Immunologic Consequences of Multiple, High-Dose Administration of Allogeneic Mesenchymal Stem Cells to Baboons", Cell Transplantation, 2006, vol. 15 (pp. 711-721).
Ben-Ami et al., "Mesenchymal stem cells as an immunomodulatory therapeutic strategy for autoimmune diseases", Autoimmunity Reviews, 2011, vol. 10 (pp. 410-415).
Blaber et al., "Analysis of in vitro secretion profiles from adipose-derived cell populations", Journal of Translational Medicine, 2012, vol. 10, No. 172 (pp. 1-16).
Bohannon et al., "The effects of therapeutic concentrations of gentamicin, amikacin and hyaluronic acid on cultured bone marrow-derived equine mesenchymal stem cells" Equine Veterinary Journal, 2013, vol. 45 (pp. 732-736).
Borjesson et al., "The Regenerative Medicine Laboratory: Facilitating Stem Cell Therapy for Equine Disease", Clin. Lab. Med., 2011, vol. 31 (pp. 109-123).
Carrade et al., "Clinicopathologic findings following intra-articular injection of autologous and allogeneic placentally derived equine mesenchymal stem cells in horses", Cytotherapy, 2011, vol. 13 (pp. 419-430).
Carrade et al., "Immunomodulation by Mesenchymal Stem Cells in Veterinary Species", Comparative Medicine, Jun. 2013, vol. 63., No. 3 (pp. 207-217).
Carrade, et al., "Comparative Analysis of the Immunomodulatory Properties of Equine Adult-Derived Mesenchymal Stem Cells", Cell Medicine, 2012, vol. 4, (pp. 1-11).

(Continued)

*Primary Examiner* — Anoop K Singh
*Assistant Examiner* — David A Montanari
(74) *Attorney, Agent, or Firm* — Foley & Lardner LLP

(57) ABSTRACT

Provided are methods of determining whether a mammalian subject having an inflammatory condition (e.g., an oral inflammatory condition) will respond positively to mesenchymal stem cell (MSC) therapy, as well as method of treating such inflammatory conditions by administering MSCs.

4 Claims, 21 Drawing Sheets

(56) References Cited

OTHER PUBLICATIONS

Carrade, et al., "Intradermal injections of equine allogeneic umbilical cord-derived mesenchymal stem cells are well tolerated and do not elicit immediate or delayed hypersensitivity reactions", Cytotherapy, 2011, 13, (pp. 1180-1192).

Chung et al., "Osteogenic proliferation and differentiation of canine bone marrow and adipose tissue derived mesenchymal stromal cells and the influence of hypoxia", Research in Veterinary Science, 2012, vol. 92 (pp. 66-75).

Corcione et al., "Human mesenchymal stem cells modulate B-cell functions", Stem Cells in Hematology, Blood, Jan. 1, 2006, vol. 107, No. 1 (pp. 367-372).

Dominici et al., "Minimal criteria for defining multipotent mesenchymal stromal cells. The International Society for Cellular Therapy position statement", Cytotherapy, 2006, vol. 8, No. 4 (pp. 315-317).

Erkers et al., "Decidual Stromal Cells Promote Regulatory T Cells and Suppress Alloreactivity in a Cell Contact-Dependent Manner", Stem Cells and Development, 2013, vol. 22, No. 19 (pp. 2596-2605).

Forbes et al., "A Phase 2 Study of Allogeneic Mesenchymal Stromal Cells for Luminal Crohn's Disease Refractory to Biologic Therapy", Clinical Gastroenterology and Hepatology, 2014, vol. 12 (pp. 64-71).

Frey et al., "Has allogeneic stem cell cryopreservation been given the 'cold shoulder'? An analysis of the pros and cons of using frozen versus fresh stem cell products in allogeneic stem cell transplantation", Bone Marrow Transplantation, 2006, vol. 38 (pp. 399-405).

Gimble et al., "Adipose-Derived Stem Cells for Regenerative Medicine", Circulation Research, May 11, 2007, vol. 100 (pp. 1249-1260).

Groh et al., "Human mesenchymal stem cells require monocyte-mediated activation to suppress alloreactive T cells", Experimental Hematology, 2005, vol. 33 (pp. 928-934).

Harley et al., "Cytokine mRNA Expression in Lesions in Cats with Chronic Gingivostomatitis", Clinical and Diagnostic Laboratory Immunology, Jul. 1999, vol. 6, No. 4 (pp. 471-478).

Hoogduijn et al., "Mesenchymal Stem Cells Induce an Inflammatory Response After Intravenous Infusion", Stem Cells and Development, 2013, vol. 22, No. 21 (pp. 1-11).

Huttenhower et al. : The Human Microbiome Project Consortium, "Structure, function and diversity of the healthy human microbiome", Nature, Jun. 14, 2012, vol. 486, (pp. 207-214).

Ivanova-Todorova et al., "Adipose tissue-derived mesenchymal stem cells are more potent suppressors of dendritic cells differentiation compared to bone marrow-derived mesenchymal stem cells", Immunology Letters, 2009, vol. 126 (pp. 37-42).

Jaager, et al., "RNA-Seq Analysis Reveals Different Dynamics of Differentiation of Human Dermis- and Adipose-Derived Stromal Stem Cells", PLoS ONE, Jun. 2012, vol. 7, No. 6 (9 pages).

Jansen et al., "Functional Differences Between Mesenchymal Stem Cell Populations Are Reflected by Their Transcriptome", Stem Cells and Development, 2010, vol. 19, No. 4 (pp. 481-489).

Kang et al., "Soluble Factors-Mediated Immunomodulatory Effects of Canine Adipose Tissue-Derived Mesenchymal Stem Cells", Stem Cells and Development, 2008, vol. 17 (pp. 681-694).

Karlsson et al., "Stromal cells from term fetal membrane are highly suppressive in allogeneic settings in vitro", Clinical and Experimental Immunology, 2011, vol. 167 (pp. 543-555).

Kassem et al., "Mesenchymal Stem Cells: Cell Biology and Potential Use in Therapy", Basic & Clinical Pharmacology & Toxicology, 2004, vol. 95 (pp. 209-214).

Kern et al., "Comparative Analysis of Mesenchymal Stem Cells from Bone Marrow, Umbilical Cord Blood, or Adipose Tissue", Stem Cells, 2006, vol. 24 (pp. 1294-1301).

Keyser et al., "Comparison of Mesenchymal Stem Cells From Different Tissues to Suppress T-Cell Activation", Cell Transplantation, 2007, vol. 16, (pp. 555-562).

Kol et al., "Autologous point-of-care cellular therapies variably induce equine mesenchymal stem cell migration, proliferation and cytokine expression", Equine Veterinary Journal, 2013, vol. 45 (pp. 193-198).

Kolf et al., "Biology of adult mesenchymal stem cells: regulation of niche, self-renewal and differentiation", Arthritis Research & Therapy, Feb. 19, 2007, vol. 9, No. 1 (pp. 1-10).

Kono et al., "Phenotypic and functional properties of feline dedifferentiated fat cells and adipose-derived stem cells" The Veterinary Journal, 2014, vol. 199 (pp. 88-96).

Krampera et al., "Role for Interferon-gamma in the Immunomodulatory Activity of Human Bone Marrow Mesenchymal Stem Cells", Stem Cells, 2006, vol. 24 (pp. 386-398).

Le Blanc et al., "Mesenchymal stem cells: progress toward promise", Cytotherapy, 2005, vol. 7, No. 1 (pp. 36-45).

Lee et al., "Autologous Mesenchymal Stem Cell Therapy Delays the Progression of Neurological Deficits in Patients With Multiple System Atrophy", Clinical Pharmacology & Therapeutics, May 2008, vol. 83, No. 5 (pp. 723-730).

Lehman et al., "Immunization-induced decrease of the CD4+:CD8+ ratio in cats experimentally infected with feline immunodeficiency virus", Veterinary Immunology and Immunopathology, 1992, vol. 35 (pp. 199-214).

Locke et al., "Human adipose-derived stem cells: isolation, characterization and applications in surgery", Anz J Surg, 2009, vol. 79 (pp. 235-244).

Martin, et al., "Isolation and characterization of multipotential mesenchymal stem cells from feline bone marrow", Experimental Hematology, 2002, 30, pp. 879-886 (2 abstracts—4 pages).

Martinello et al., "Canine adipose-derived-mesenchymal stem cells do not lose stem features after a long-term cryopreservation", Research in Veterinary Science, 2011, vol. 91 (pp. 18-24).

Matthews et al., "Hyperactivity and reactivity of peripheral blood neutrophils in chronic periodontitis", Clinical and Experimental Immunology, 2006, vol. 147, (pp. 255-264).

Melief et al., "Adipose Tissue-Derived Multipotent Stromal Cells Have a Higher Immunomodulatory Capacity Than Their Bone Marrow-Derived Counterparts", Stem Cells Translational Medicine, 2013, vol. 2 (pp. 455-463).

Moll et al., "Are Therapeutic Human Mesenchymal Stromal Cells Compatible with Human Blood?", Stem Cells Translational and Clinical Research, 2012, vol. 30 (pp. 1565-1574).

Moutsopoulos et al., "P. gingivalis promotes Th17 inducing pathways in chronic periodontitis", Journal of Autoimmunology, Dec. 2012, vol. 39, No. 4 (pp. 294-303).

Owens et al., "Processing of equine bone marrow using the automated MarrowXpress System: RBC depletion, volume reduction, and mononuclear cell recovery", Veterinary Clinical Pathology, 2011, vol. 40 No.4 (pp. 444-449).

Park et al., "Safety and immunomodulatory effects of allogeneic canine adipose-derived mesenchymal stromal cells transplanted into the region of the lacrimal gland, the gland of the third eyelid and the knee joint", Cytotherapy, 2013, vol. 15 (pp. 1498-1510).

Peroni et al., Anti-Inflammatory and Immunomodulatory Activities of Stem Cells, Vet. Clin. Equine, 2011, vol. 27 (pp. 351-362).

Prasad et al., "Efficacy and Safety of Ex Vivo Cultured Adult Human Mesenchymal Stem Cells (Prochymal) in Pediatric Patients with Severe Refractory Acute Graft-Versus-Host Disease in a Compassionate Use Study", Biol Blood Marrow Transplant, 2011, vol. 17 (pp. 534-541).

Prestwich, "Hyaluronic Acid-Based Clinical Biomaterials Derived for Cell and Molecule Delivery in Regenerative Medicine", J Control Release, Oct. 30, 2011, vol. 155, No. 2 (pp. 193-199).

Quimby et al., "Evaluation of intrarenal mesenchymal stem cell injection for treatment of chronic kidney disease in cats: a pilot study", Journal of Feline Medicine and Surgery, 2011, vol. 13 (pp. 418-426).

Quimby et al., "Safety and efficacy of intravenous infusion of allogeneic cryopreserved mesenchymal stem cells for treatment of chronic kidney disease in cats: results of three sequential pilot studies", Stem Cell Research & Therapy, 2013, vol. 4, No. 48 (pp. 1-12).

(56) References Cited

OTHER PUBLICATIONS

Rasmusson, et al., "Mesenchymal Stem Cells Inhibit the Formation of Cytotoxic T Lymphocytes, but not Activated Cytotoxic T Lymphocytes or Natural Killer Cells", Transplantation, Oct. 7, 2003, vol. 76, No. 8 (pp. 1208-1213).
Ratliff et al., "Mesenchymal Stem Cells, Used As Bait, Disclose Tissue Binding Sites", The American Journal of Pathology, Aug. 2010, vol. 177, No. 2 (pp. 873-883).
Ren et al., "Species Variation in the Mechanisms of Mesenchymal Stem Cell-Mediated Immunosuppression", Stem Cells, 2009, vol. 27 (pp. 1954-1962).
Ryan et al., "Interferon-gamma does not break, but promotes the immunosuppressive capacity of adult human mesenchymal stem cells", Clinical and Experimental Immunology, 2007, vol. 149 (pp. 353-363).
Schuh et al., "Identification of variables that optimize isolation and culture of multipotent mesenchymal stem cells from equine umbilical-cord blood", AJVR, Dec. 2009, vol. 70, No. 12 (pp. 1526-1535).
Semon et al., "Administration of Murine Stromal Vascular Fraction Ameliorates Chronic Experimental Autoimmune Encephalomyelitis", Stem Cells Translational Medicine, 2013, vol. 2 (pp. 789-796).
Singer et al., "Mesenchymal Stem Cells: Mechanisms of Inflammation", The Annual Review of Pathology: Mechanisms of Disease, 2011, vol. 6 (pp. 457-478).
Sole et al., "Distribution and persistence of technetium-99 hexamethyl propylene amine oxime-labelled bone marrow-derived mesenchymal stem cells in experimentally induced tendon lesions after intratendinous injection and regional perfusion of the equine distal limb", Equine Veterinary Journal, 2013, vol. 45 (pp. 726-731).
Sole et al., "Scintigraphic evaluation of intra-arterial and intravenous regional limb perfusion of allogeneic bone marrow-derived mesenchymal stem cells in the normal equine distal limb using 99mTc-HMPAO", Equine Veterinary Journal, 2012, vol. 44 (pp. 594-599).
Stark et al., "Phagocytosis of Apoptotic Neutrophils Regulates Granulopoiesis via IL-23 and IL-17", Immunity, Mar. 2005, vol. 22 (pp. 285-294).
Sun et al., "Systemic administration of autologous adipose-derived mesenchymal stem cells alleviates hepatic ischemia-reperfusion injury in rats", Critical Care Med, 2012, vol. 40, No. 4 (pp. 1279-1290).
Toupadakis et al., "Mobilization of Endogenous Stem Cell Populations Enhances Fracture Healing in a Murine Femoral Fracture Model", Cytotherapy, Sep. 2013, vol. 15, No. 9 (pp. 1136-1147).
Toupadakis, et al., "Comparison of the osteogenic potential of equine mesenchymal stem cells from bone marrow, adipose tissue, umbilical cord blood, and umbilical cord tissue", AJVR, Oct. 2010, vol. 71, No. 10 (pp. 1237-1245).
US Final Office Action on U.S. Appl. No. 14/915,871 dated Mar. 25, 2020 (35 pages).
US Final Office Action on U.S. Appl. No. 14/915,871 dated Nov. 28, 2018 (22 pages).
US Non-Final Office Action on U.S. Appl. No. 14/915,871 dated Dec. 11, 2019 (39 pages).
US Non-Final Office Action on U.S. Appl. No. 14/915,871 dated May 11, 2021 (34 pages).
Vidal et al., "Evaluation of Senescence in Mesenchymal Stem Cells Isolated from Equine Bone Marrow, Adipose Tissue, and Umbilical Cord Tissue", Stem Cells and Development, 2012, vol. 21, No. 2 (pp. 273-283).
Vieira et al., "Isolation, Characterization, and Differentiation Potential of Canine Adipose-Derived Stem Cells", Cell Transplantation, 2010, vol. 19 (pp. 279-289).
Webb et al., "In vitro comparison of feline bone marrow-derived and adipose tissue-derived mesenchymal stem cells", Journal of Feline Medicine and Surgery, 2011, vol. 14, No. 2 (pp. 165-168).
Wood et al., "Periocular and Intra-Articular Injection of Canine Adipose-Derived Mesenchymal Stem Cells: An In Vivo Imaging and Migration Study", Journal of Ocular Pharmacology and Therapeutics, 2012, vol. 28, No. 3 (pp. 307-317).
Wood et al., "The modulation of canine mesenchymal stem cells by nano-topographic cues", Exp. Cell. Res., Nov. 15, 2012, vol. 318, No. 19 (pp. 2438-2445).
Yoo et al., "Comparison of immunomodulatory properties of mesenchymal stem cells derived from adult human tissues", Cellular Immunology, 2009, vol. 259 (pp. 150-156).
Zhang, et al., "Clinical observation of Mesenchymal stem cells for treatment of steroid-resistant chronic graft-versus-host disease", Chinese Journal of Internal Medicine, Jul. 2009, vol. 48, No. 7, pp. 542-546 (abstract 2 pages).
Zhao et al., "Intravenous injection of mesenchymal stem cells is effective in treating liver fibrosis" World Journal of Gastroenterol, Mar. 14, 2012, vol. 18, No. 10 (pp. 1048-1058).
U.S. Requirement for Restriction/Election dated Dec. 27, 2016 issued in U.S. Appl. No. 14/915,871.
U.S. Office Action dated Feb. 21, 2017 issued in U.S. Appl. No. 14/915,871.
U.S. Final Office Action dated Jul. 6, 2017 issued in U.S. Appl. No. 14/915,871.
U.S. Office Action dated Mar. 16, 2018 issued in U.S. Appl. No. 14/915,871.
PCT International Search Report and Written Opinion dated Nov. 7, 2014 issued in PCT/US2014/051524.
PCT International Preliminary Report on Patentability and Written Opinion dated Mar. 17, 2016 issued in PCT/US2014/051524.
PCT International Search Report and Written Opinion dated Dec. 29, 2016 issued in PCT/US16/55529.
PCT International Preliminary Report on Patentability dated Apr. 19, 2018 issued in PCT/US2016/055529 .
European Extended Search Report dated Mar. 15, 2017 issued in Application No. EP 14 841 620.9.
Arzi et al., (2010) "Presence and quantification of mast cells in the gingiva of cats with tooth resorption, periodontitis and chronic stomatitis," *Archives of Oral Biology*, 55:148-154.
Arzi, Boaz et al., (2015) "Feline Foamy Virus Adversely Affects Feline Mesenchymal Stem Cell Culture and Expansion: Implications for Animal Model Development," *Stem Cells and Development*, 24(7):814-823.
Arzi, Boaz et al., (2016) "Therapeutic efficacy of fresh, autologous mesenchymal stem cells for severe refractory gingivostomatitis in cats," *Stem Cells Translational Medicine* 2016, 5:1-12. [Published Ahead of Print on Nov. 18, 2015 as 10.5966/sctm.2015-0127].
Arzi, Boaz et al., (2017) "Therapeutic Efficacy of Fresh, Allogeneic Mesenchymal Stem Cells for Severe Refractory Feline Chronic Gingivostomatitis," *Stem Cells Translational Medicine*, 6:1710-1722.
Bachtiar, et al., "Decreased CD4+/CD8+ Ratio in Major Type of Recurrent Aphthous Ulcers: Comparing Major to Minor Types of Ulcers", Asian Pacific Journal of Allergy and Immunology, 1998, vol. 16, pp. 75-79.
Beckman, Brett, (Oct. 2, 2008) "Potential help for refractory feline chronic gingivo-stomatitis (Proceedings)," *dvm360*, [Downloaded at http://veterinarycalendar.dvm360.com/potential-help-refractory-feline-chronic-gingivo-stomatitis-proceeding], pp. 1-3.
Clark, Kaitlin C. et al., (2016) "Canine and Equine Mesenchymal Stem Cells Grown in Serum Free Media Have Altered Immunophenotype," *Stem Cell Rev and Rep*, 12:245-256. [Published online: Dec. 5, 2015].
Clark, Kaitlin C. et al., (2017) "Human and feline adipose-derived mesenchymal stem cells have comparable phenotype, immunomodulatory functions, and transcriptome," *Stem Cell Research & Therapy*, 8:69, 16pp.
Duffy, et al., "Mesenchymal stern cells effects on T-cell effector pathways", Stern Cell Research & Therapy, 2011, 2:34, pp. 1-9.
Ebersole et al., (Jun. 2013) "Periodontal disease immunology: 'double indemnity' in protecting the host," *Periodontol 2000*, 62(1):163-202, pp. 1-61.
English, K., (2013) "Mechanisms of mesenchymal stromal cell immunomodulation," *Immunol Cell Biol.*, 91(1):19-26, Abstract Only, 2pp. [Downloaded on Sep. 18, 2017 at https://www.ncbi.nlm.nih.gov/pubmed/23090487].

(56) References Cited

OTHER PUBLICATIONS

François et al., (2012) "Cryopreserved mesenchymal stromal cells display impaired immunosuppressive properties as a result of heat-shock response and impaired interferon-γ licensing," *Cytotherapy*, 14:147-152.

Galipeau, J., "Concerns arising from MSC retrieval from cryostorage and effect on immune suppressive function and pharmaceutical usage in clinical trials," ISBT Science Series, vol. 8, May 31, 2013, pp. 100-101.

Ge, S. et al., (Nov. 2012) "Isolation and characterization of mesenchymal stem cell-like cells from healthy and inflamed gingival tissue: potential use for clinical therapy," *Regen Med*, 2012, 7(6):819-832.

Hale, Fraser A., (Dec. 2010) "The Disease Formerly Known As Lymphocytoc/Plasmacytic Gingivo-Stomatitis," *Hale Veterinary Clinic*, www.toothvet.ca, pp. 1-16.

Healey et al., (2007) "Prevalence of feline chronic gingivo-stomatitis in first opinion veterinary practice," *Journal of Feline Medicine and Surgery*, 9:373-381.

Hof-Nahor et al., (Oct. 1, 2012) "Human mesenchymal stem cells shift CD8+ T cells towards a suppressive phenotype by inducing tolerogenic monocytes," *Journal of Cell Science*, 125(19):4640-4650.

Honmou et al., (2011) "Intravenous administration of auto serum-expanded autologous mesenchymal stem cells in stroke", *Brain, A Journal of Neurobiology*, 134:1790-1807.

Lommer et al., (2003) "Concurrent oral shedding of feline calicivirus and feline herpesvirus 1 in cats with chronic gingivostomatitis," *Oral Microbiology Immunology*, 18:131-134.

Lommer, (2013) "Oral Inflammation in Small Animals," *Vet Clin Small Anim*, 43:555-571.

Maue et al., (2009) "CD4+ T Cells and Immunosenescence—A Mini-Review," *Gerontology*, 55:491-495.

Moll et al., (2014) "Do Cryopreserved Mesenchymal Stromal Cells Display Impaired Immunomodulatory and Therapeutic Properties?" *Stem Cells*, 32:2430-2442.

Najar et al., (Feb. 2016) "Mesenchymal stromal cells and immunomodulation: A gathering of regulatory immune cells," *Cytotherapy*, 18(2): 160-171, Abstract Only, 2pp. [Downloaded on Sep. 16, 2017 at https://www.ncbi.nlm.nih.gov/pubmed/26794710].

Otsuru et al., (2015) "Genomic and functional comparison of mesenchymal stromal cells prepared using two isolation methods," *Cytotherapy*, 17:262-270.

Sun, et al., "Expression of Interleukin-2 Receptor by Activated Peripheral Blood Lymphocytes Upregulated by the Plasma Level of Interleukin-2 in Patients with recurrent Aphthous Ulcers", Proc. Natl. Sci, Counc. Roc( B), 2000, vol. 24, No. 3, pp. 116-122.

Wang et al., (2016) "Human mesenchymal stem cells (MSCs) for treatment towards immune- and inflammation-mediated diseases: review of current clinical trials," *Journal of Biomedical Science*, 23:76, 13pp.

Wikipedia, *the Free encyclopedia*, "Immunosenescence," 5pp [Downloaded on Sep. 16, 2017 at https://en.wikipedia.org/wiki/IMMUNOSENESCENCE].

Winer et al., (Jul. 18, 2016) "Therapeutic Management of Feline Chronic Gingivostomatitis: A Systematic Review of the Literature," *Frontiers in Veterinary Science*, 3(54), 10pp [XP055351418, doi: 10.3389/fvets.2016.00054].

Winn Feline Foundation, "Winn Feline Foundation Awards Grants for Feline Health Studies in Partnership With the Miller Trust," Dec. 17, 2012, 3pp.

"Feline Dental Disease," (1988) AVDC American Veterinary Dental College, [Downloaded on Sep. 16, 2017 at https://www.avdc.org/dentaldisease.html], 3pp.

Allocure Inc., "A Study to Evaluate the Safety and Efficacy of AC607 for the Treatment of Kidney Injury in Cardiac Surgery Subjects (ACT-AKI)" ClinicalTrials.gov Identifier: NCT01602328, 2012.

Aratana Therapeutics, "Aratana Therapeutics Announces Study Results for AT-016" www.aratana.com, 2017.

Athersys Inc., "Athersys Announces Results From Phase 2 Study of MultiStem(R) Cell Therapy for Ulcerative Colitis" www.athersys.com Press Release, 2014.

Bersenev, Alexey, "Cell therapy clinical trials failures in 2014" Cell Trials—Current Trends in Cell Therapy, 2015.

Bersenev, Alexey, "Cell therapy trials failures in 2013" Cell Trials—Current Trends in Cell Therapy, 2013.

Bersenev, Alexey, "Lecture: Jacques Galipeau—Industrial MSC product failure analysis" Stem Cell Assays, Jan. 23, 2016; http://stemcellassays.com/2016/lecture-jaques-galipeau-industrial-msc-product-failure-analysis/; accessed Jul. 12, 2018.

Bersenev, Alexey, "Stem cell therapy of type 1 diabetes—recent failed trials" Cell Trials—Current Trends in Cell Therapy, 2012.

Chullikana, et al., "Randomized, double-blind, phase I/II study of intravenous allogeneic mesenchymal stromal cells in acute myocardial infarction" Cythotherapy, Mar. 2015; 17 (3):250-61 (Epub Dec. 4, 2014) [Abstract Only].

Feuerstein, Adam "Osiris Stem Cell Therapy Fails Diabetes Trial" http://www.thestreet.com/story/11362832/1/osiris-stem-cell-therapy-fail, 2012.

Gao, et al., "A critical challenge: Dosage-related efficacy and acute complication intracoronary injection of autologous bone marrow mesenchymal stem cells in acute myocardial infarction" International Journal of Cardiology 128:3191-3199, 2013.

Ghodsi, et al., "The Effect of Fetal Liver-Derived Cell Suspension Allotransplantation on Patients with Diabetes: First Year of Follow-up," Acta Medica Iranica, 2012, pp. 541-546.

Giannopoulou, et al. "Effect of a single autologous cord blood infusion on beta-cell and immune function in children with new onset type 1 diabetes: a non-randomized, controlled trial" Pediatric Diabetes, 2014, pp. 100-109.

Haller, et al., "Autologous Umbilical Cord Blood Transfusion in Young Children With Type 1 Diabetes Fails to Preserve C-Peptide" Diabetes Care, 2011, pp. 1-3.

Lee, et al., "A Randomized, Open-Label, Multicenter Trial for the Safety and Efficacy of Adult Mesenchymal Stem Cells after Acute Myocardial Infraction" J Korean Med Sci, vol. 29, 2014, pp. 29-31.

Llufriu, et al., "A Randomized Placebo-Controlled Phase II Trial of Autologous Mesenchymal Stem Cells in Multiple Sclerosis" PLOS One, 2014, pp. 1-15.

Nasseri, et al., "Phase III randomized clinical trial comparing the effects of autologous bone marrow derived MNC and CD 133 cells transplantation in amipatients during CABG" Cytotherapy, 2013.

Osiris Therapeutics, Inc., "Osiris Therapeutics Provides Update on Groundbreaking Stem Cell Trial for Type 1 Diabetes" JDRF, 2012.

Squillaro, et al., "Clinical Trials With Mesenchymal Stem Cells: An Update" Cell Transplantation, vol. 25, 2016, pp. 829-848.

Surder, et al., "Intracoronary Injection of Bone Marrow Derived Mononuclear Cells, Early or Late after Acute Myocardial Infraction: Effects on Global Left Ventricular Function" Circulation, 2013.

Traverse, et al., "One-Year Follow-up of Intracoronary Stem Cell Delivery on Left Ventricular Function Following ST-Elevation Myocardial Infarction" JAMA, 2014, pp. 301-302.

Trounson, et al., "Stem Cell Therapies in Clinical Trials: Progress and Challenges" Cell Stem Cell, 2015, pp. 11-22.

Zheng, et al., "Treatment of acute respiratory distress syndrome with allogeneic adipose-derived mesenchymal stem cells: a randomized, placebo-controlled pilot study" Respiratory Research, 2014, pp. 1-10.

Non-Final Office Action on U.S. Appl. No. 17/498,683 DTD Mar. 29, 2023, 12 pages.

\* cited by examiner

Stomatitis Index

| Cat # | Entry | Exit | % recovery |
|---|---|---|---|
| 1 | 20.00 | 0.00 | 100.00 |
| 2 | 18.25 | 0.25 | 98.63 |
| 3 | 11.00 | 4.00 | 63.64 |
| 4 | 22.50 | 20.75 | 7.78 |
| 5 | 5.75 | 2.00 | 65.22 |
| 6 | 21.75 | 1.00 | 95.40 |
| 7 | 11.75 | 12.00 | -2.13 |

*Fig. 3B*

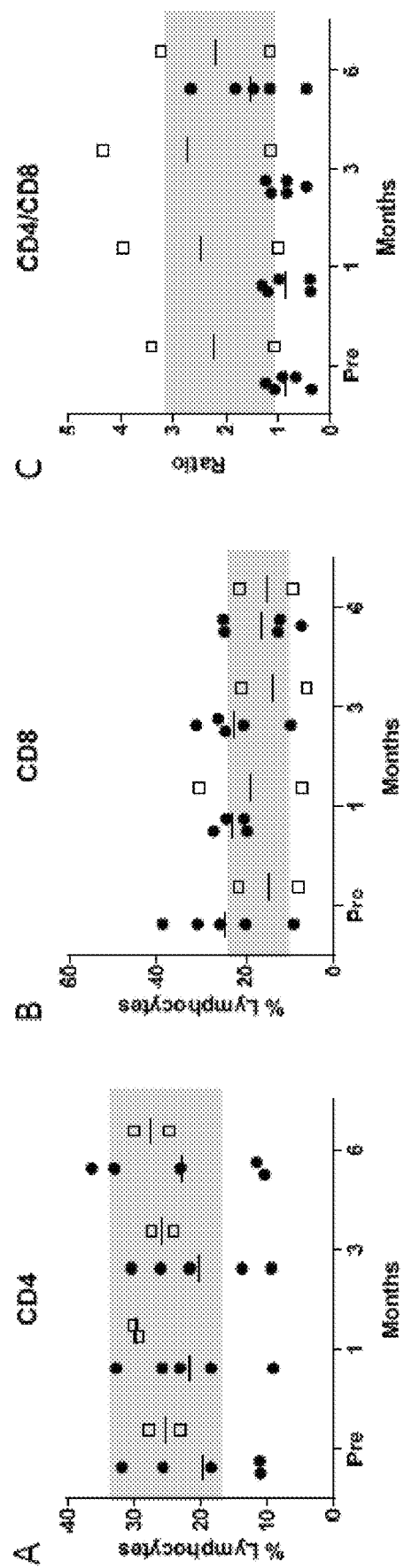
Fig. 5A-C

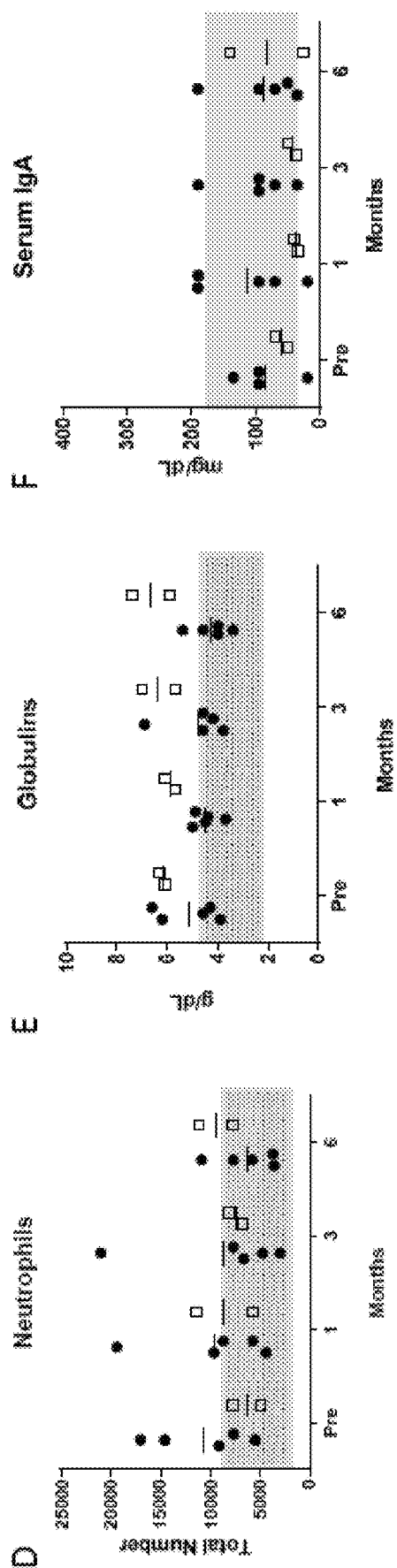
*Fig. 5D-F*

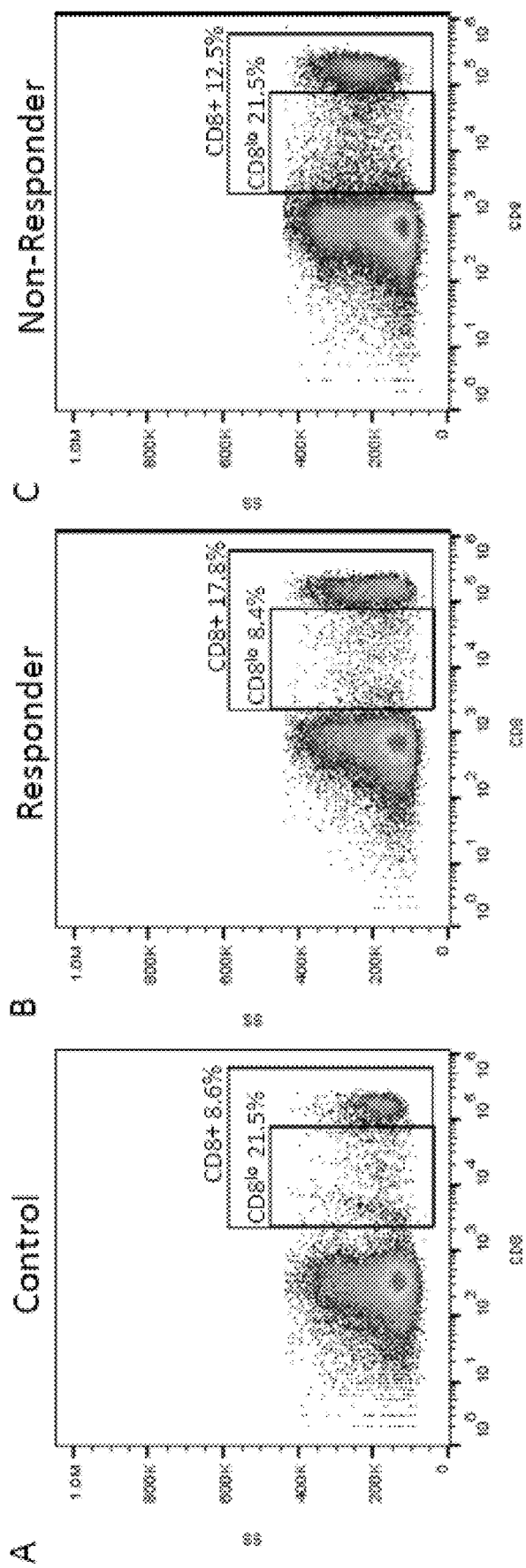
Fig. 6A-C

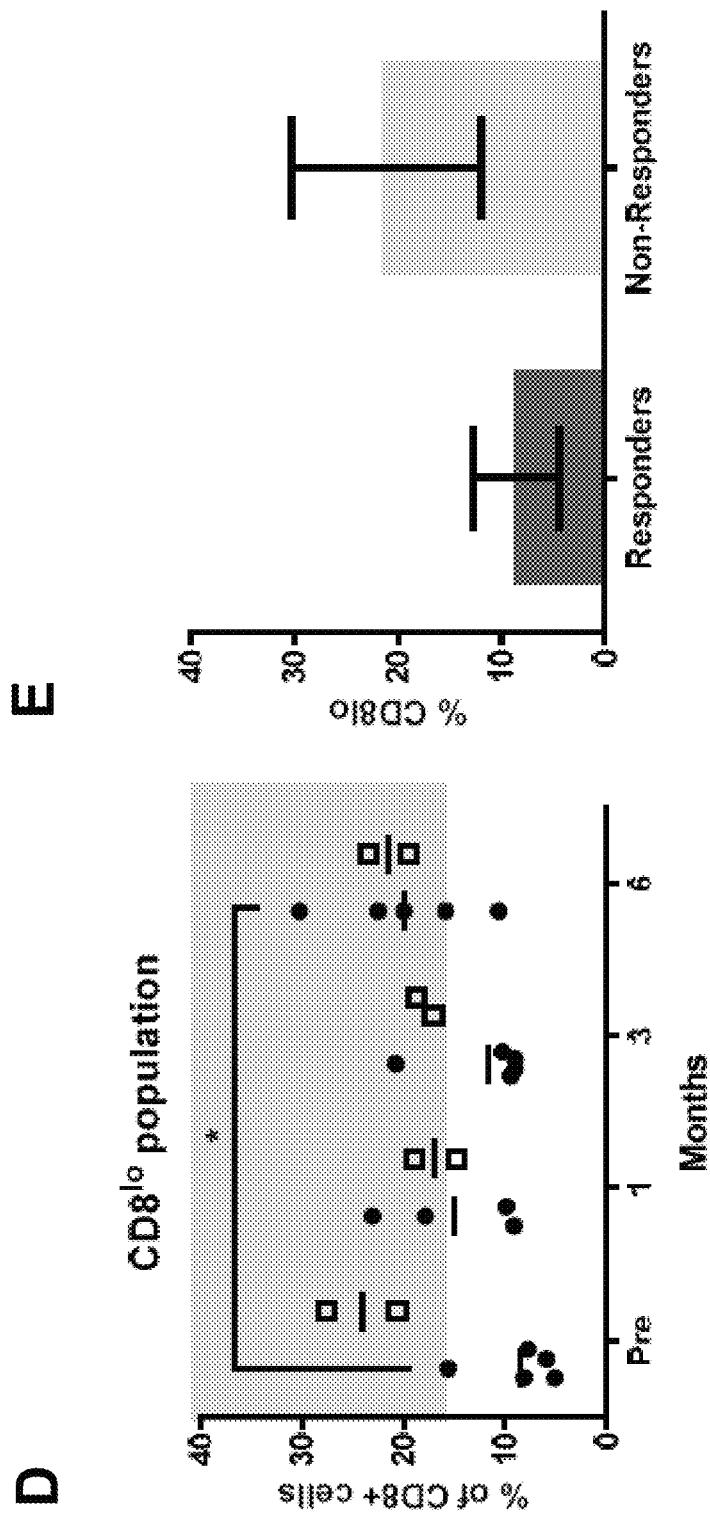
Fig. 6D-E

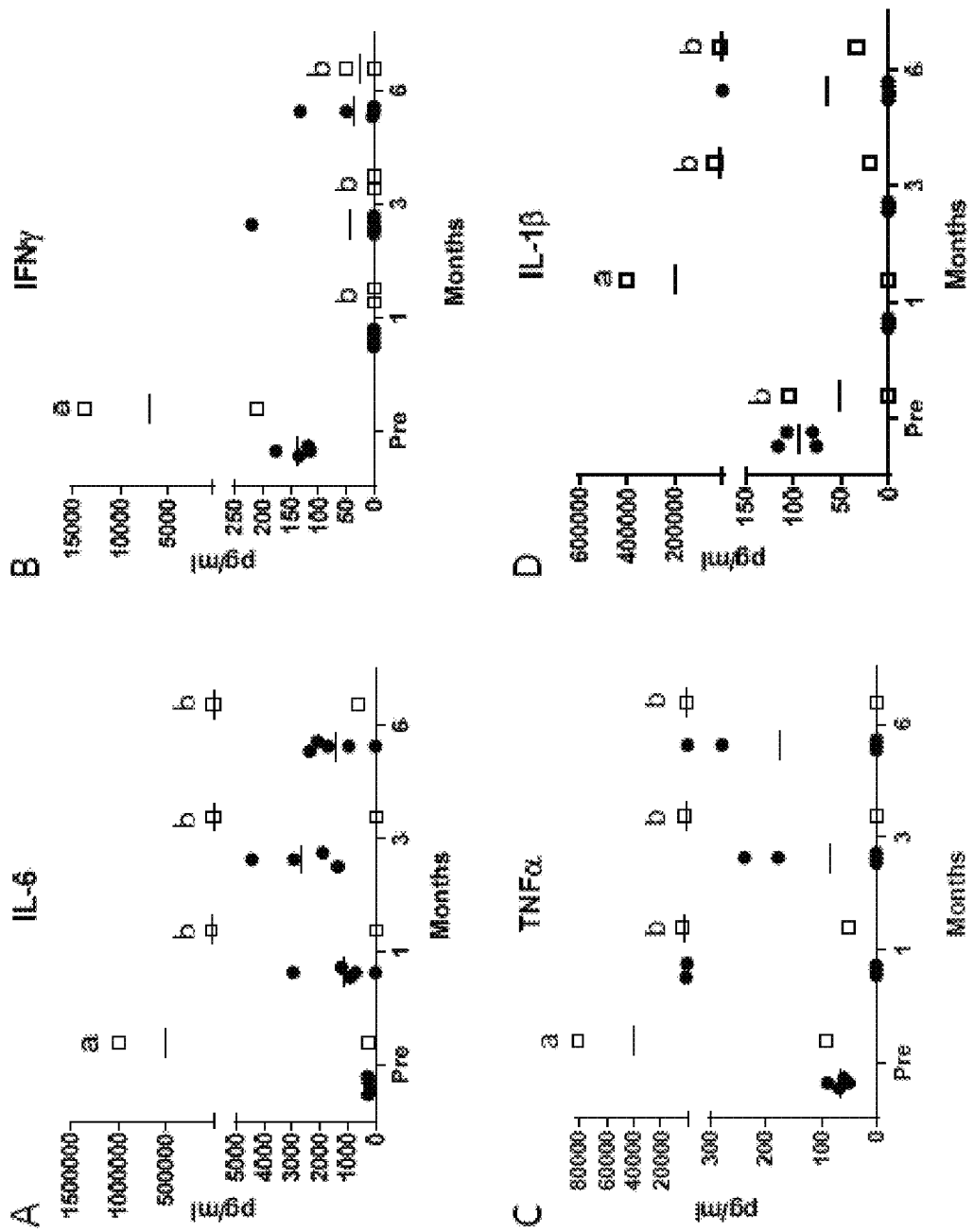
Fig. 7A-D

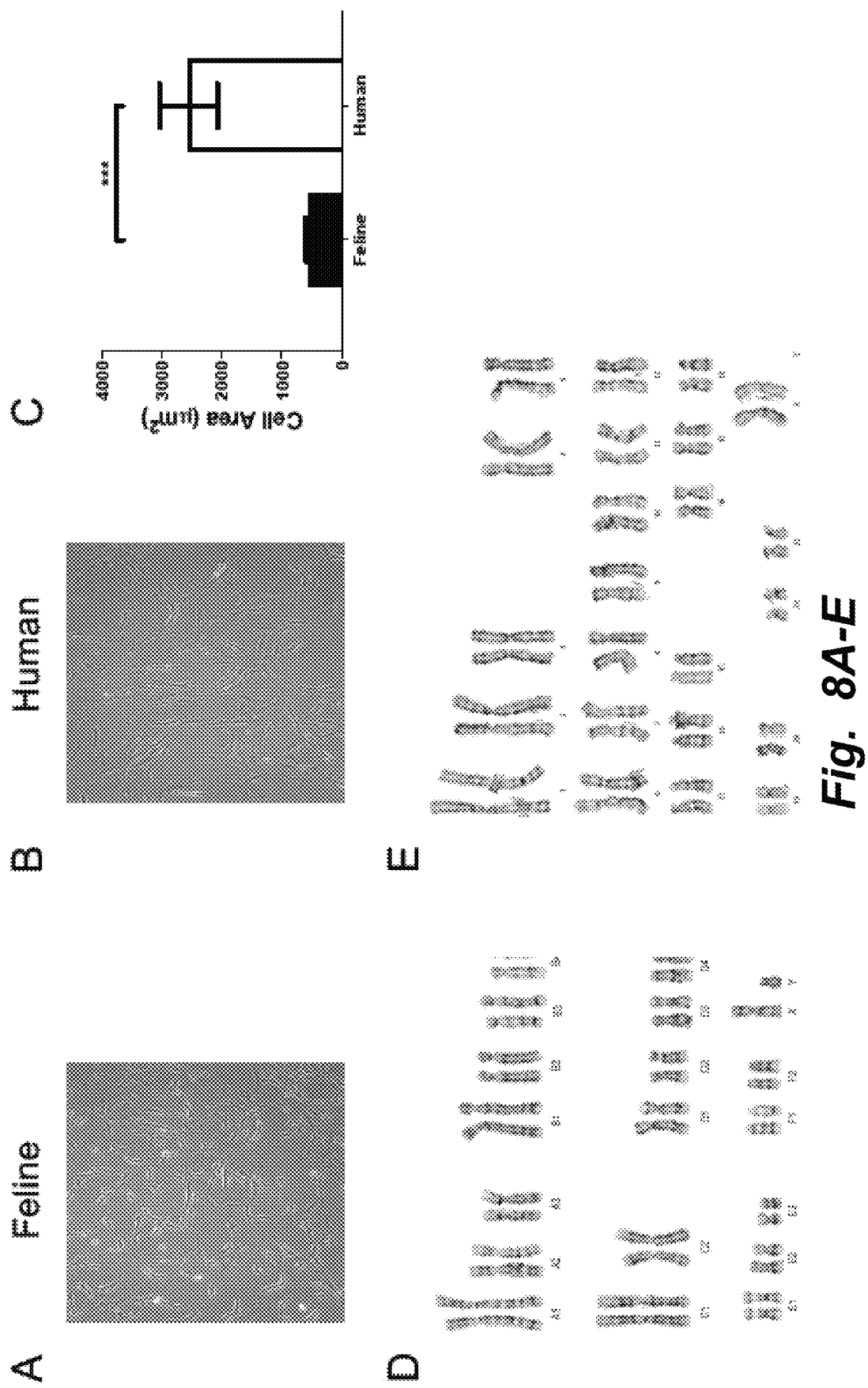
Fig. 8A-E

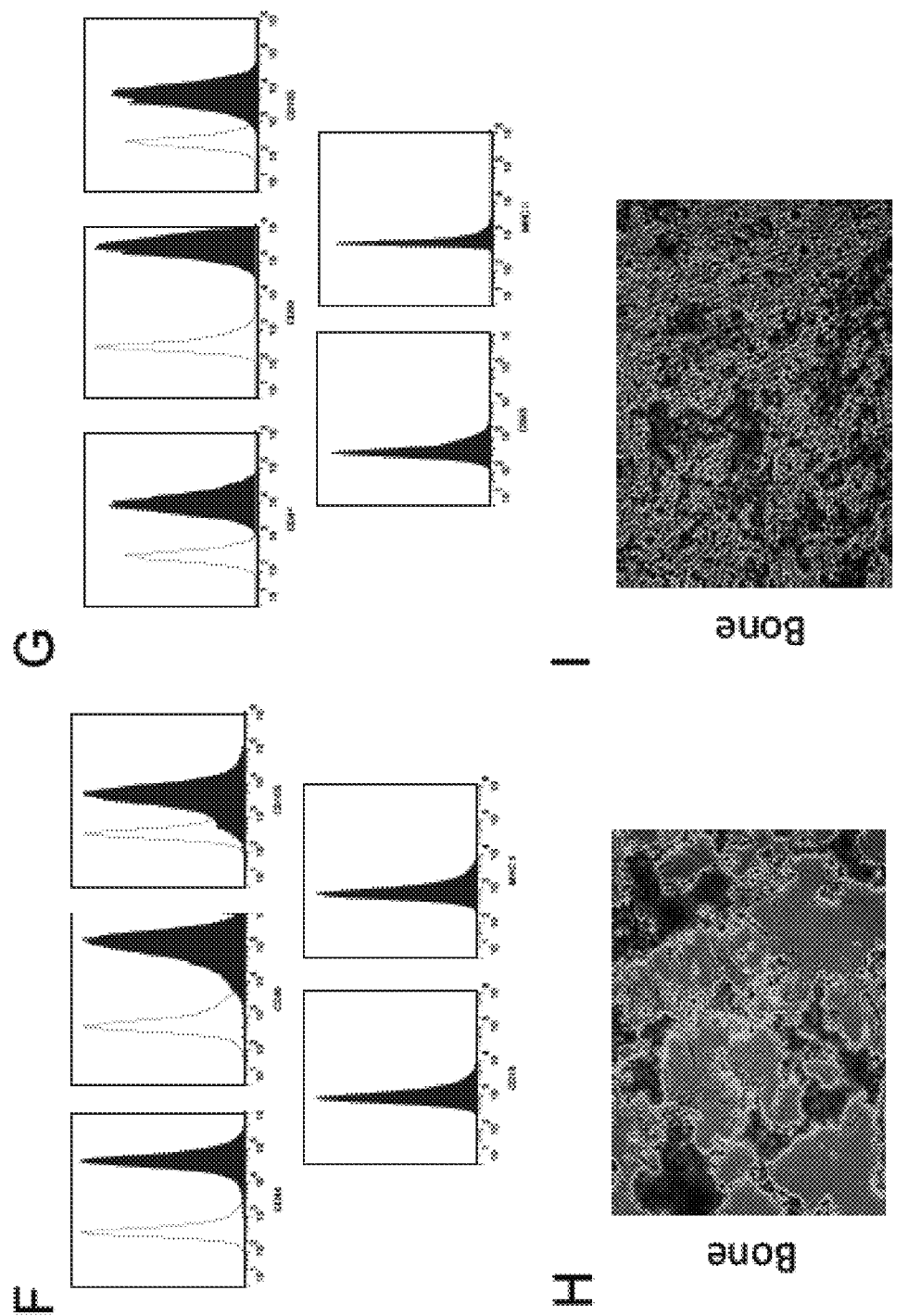
Fig. 8F-I

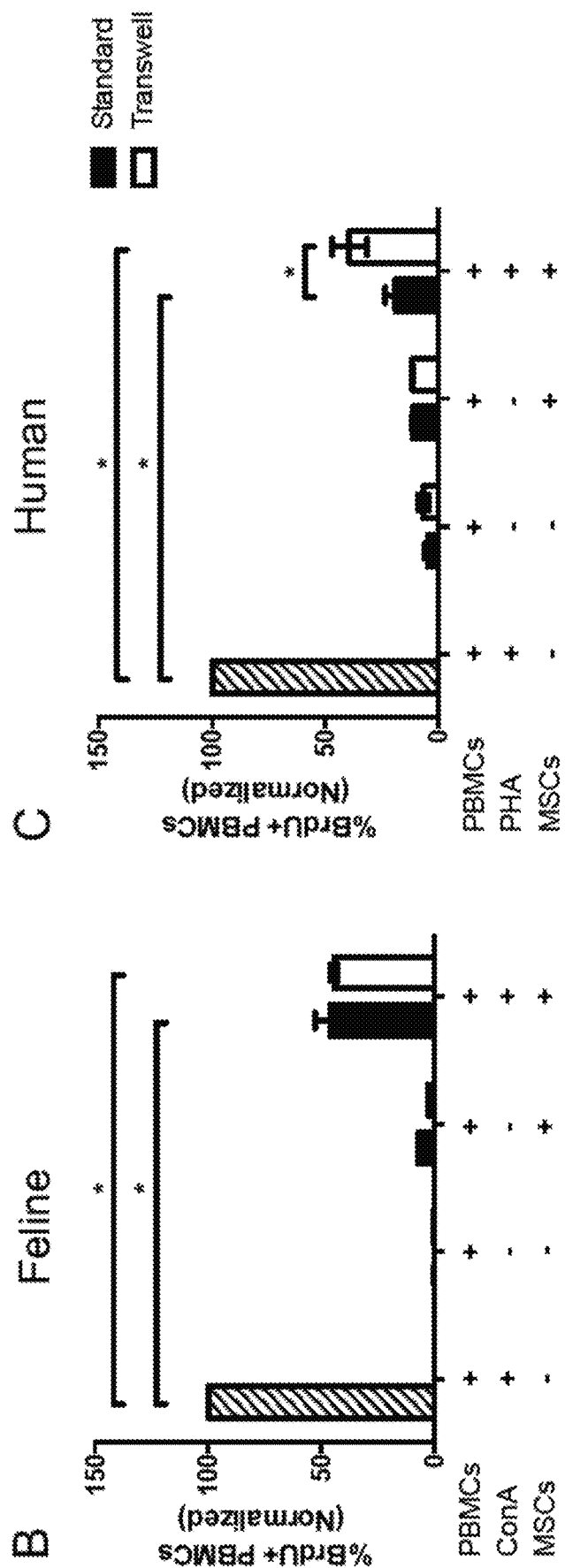
Fig. 9B-C

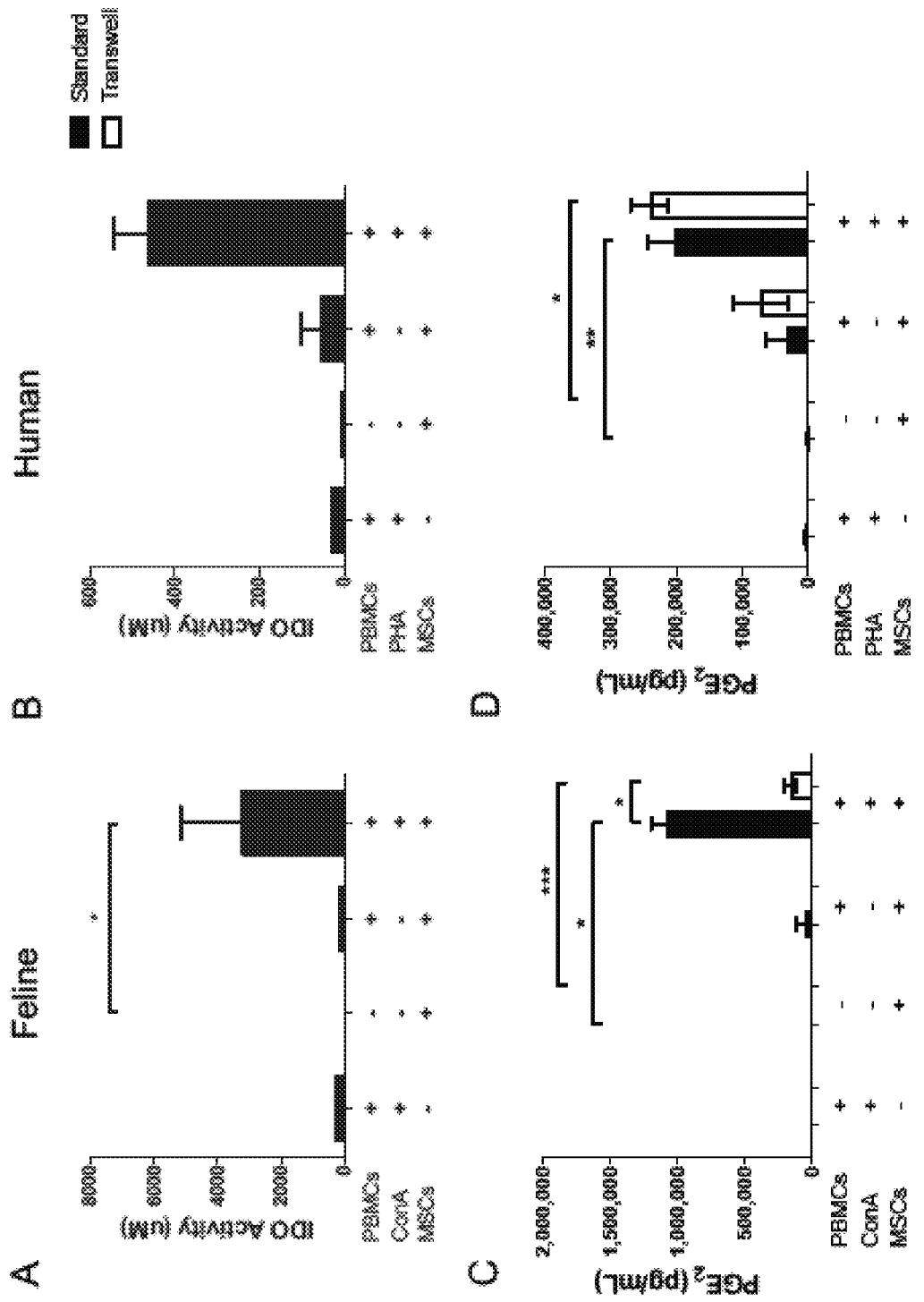
Fig. 10A-D

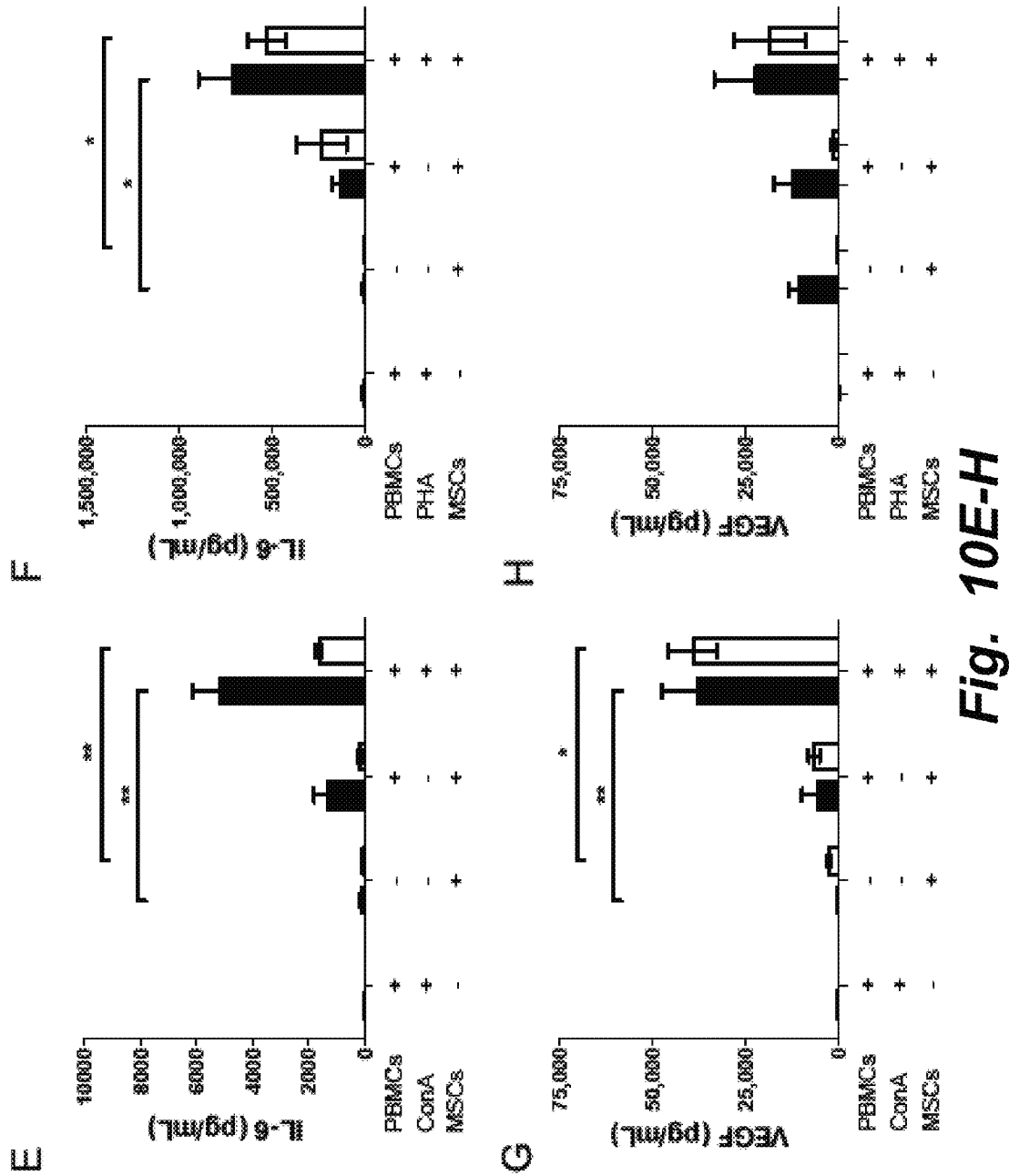
Fig. 10E-H

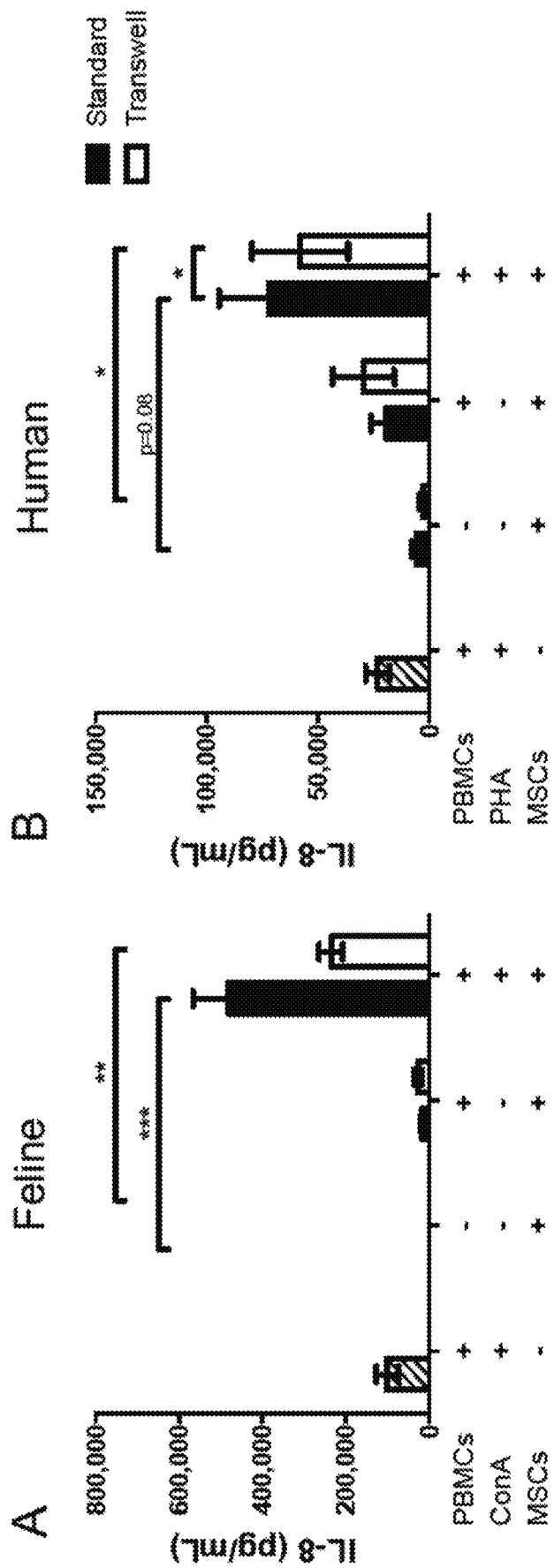
Fig. 11A-B

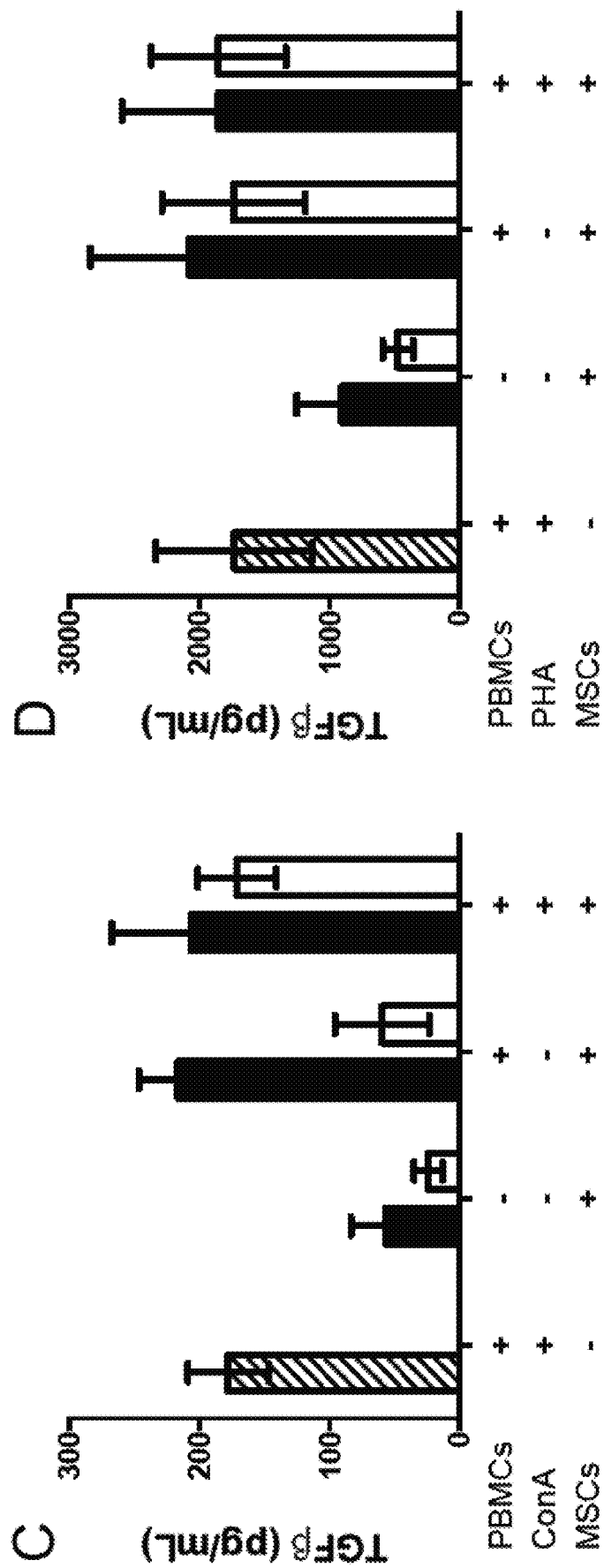
Fig. 11C-D

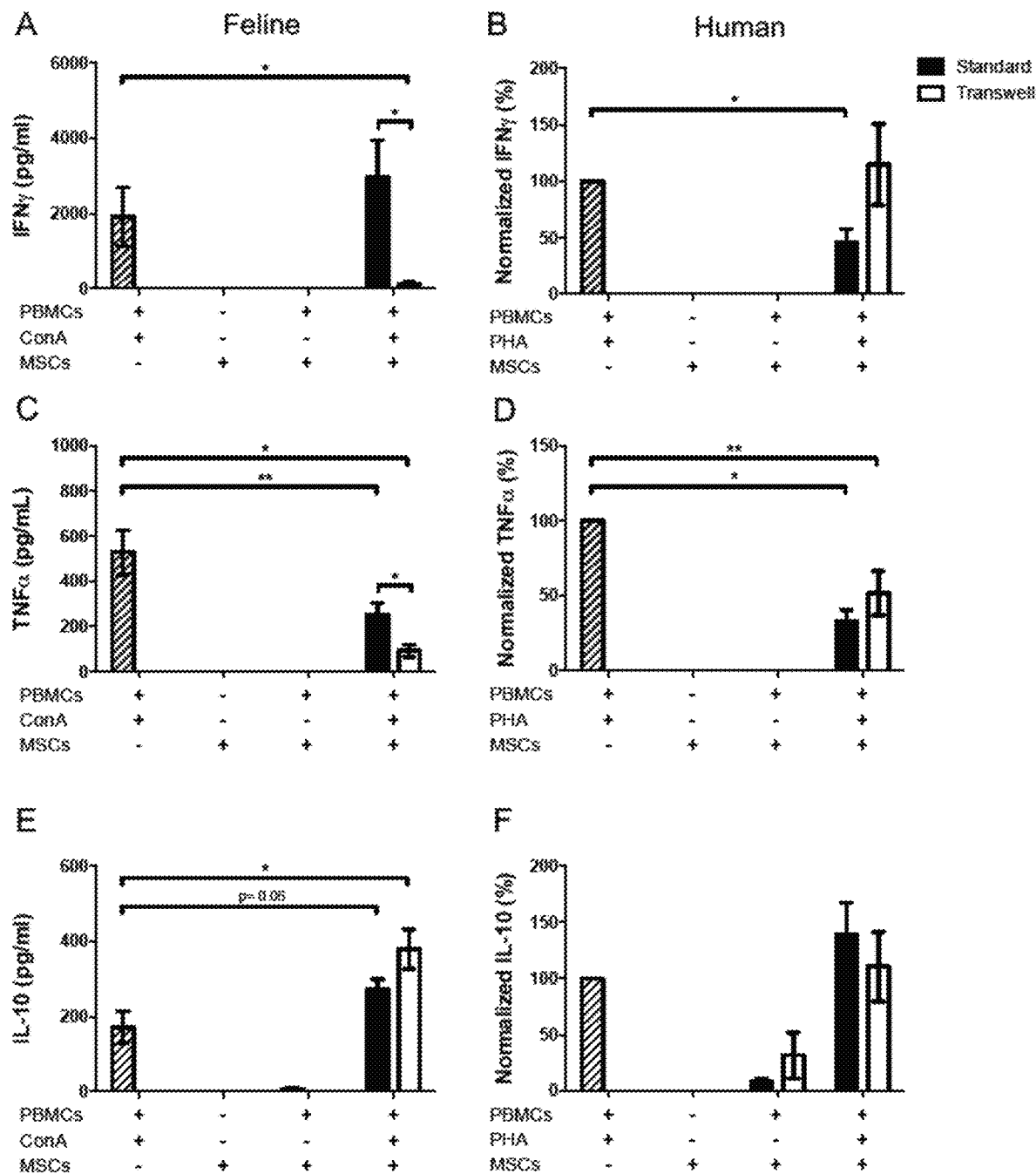
Fig. 12A-F

USE OF MESENCHYMAL STEM CELLS FOR THE TREATMENT OF INFLAMMATION

CROSS-REFERENCE TO RELATED APPLICATIONS

This application is the U.S. National Phase under 35 U.S.C. § 371 of Intl. Application No. PCT/US2016/055529, filed on Oct. 5, 2016, which claims the benefit under 35 U.S.C. § 119(e) of U.S. Provisional Application No. 62/237,115, filed on Oct. 5, 2015, which are hereby incorporated herein by reference in their entireties for all purposes.

STATEMENT OF GOVERNMENTAL SUPPORT

This work was supported in part by Grant No 1R21DE024711-01 from the National Institutes of Health. The Government has certain rights in this invention.

BACKGROUND

Immune-mediated oral mucosal inflammatory diseases are prevalent in the human population and include oral lichen planus (OLP), stomatitis, pemphigus and pemphigoid (1, 2). These disorders cause painful mucosal lesions that markedly reduce quality of life and often require long-term immunosuppressive therapy with significant associated risks and side effects. The pathogenesis of these diseases is complex and heterogeneous, but consistently involves tissue infiltration primarily by activated, effector T and B cells, with a skew towards a Th1 phenotype (3-5).

Naturally occurring diseases in client-owned animal species serve as useful animal models of human disease, as they reflect the complex genetic, environmental and physiologic variation present in outbred populations. Feline chronic gingivostomatitis (FCGS) is a severe, idiopathic oral inflammatory disease of cats that is estimated to affect 0.7% to 10% of the general cat population (6-10). Clinical signs are moderate to severe oral pain and discomfort, including inappetence (e.g., loss of appetite), reduced grooming, weight loss and hypersalivation (7, 8, 11). FCGS can be debilitating, and severely affected cats are often euthanized. Approximately 70% of cats respond to the current standard of care for FCGS, which is full or near-full mouth tooth extraction. The remaining 30% of cats do not respond to tooth extraction and require life-long therapy with antibiotics, corticosteroids, and pain medication (refractory FCGS) (7). Spontaneous disease resolution has not been reported in FCGS affected cats. The pathogenesis of FCGS is poorly understood but is thought to be due to the host immune system responding inappropriately to chronic oral antigenic stimulation secondary to underlying oral disease or clinical/subclinical viral infections (11-14).

Adult mesenchymal stromal/stem cells (MSCs) are adherent, fibroblast-like, multipotent stem cells (15, 16) were isolated from multiple tissue types, including adipose tissue. Adipose-derived MSCs (ASCs) have been isolated from humans and several domestic animal species including cats (17-23). Autologous ASCs are non-immunogenic, safe in people and animals, and have been used clinically in horses and people for more than 8 years with no significant adverse reactions reported other than transient fever in people, occasional transfusion reactions in cats and self-resolving inflammatory flares in horses (22, 24, 25). MSCs regenerative ability is attributed in part to their ability to modulate both innate and adaptive immune responses (26-30). MSCs inhibit T-cell proliferation, alter B-cell function, down-regulate MHC II on antigen presenting cells and inhibit dendritic cell maturation and differentiation (26, 27, 29, 30). MSCs are currently being used in phase I through III human clinical trials for inflammatory diseases including Crohn's disease and Graft vs. Host Disease (GVHD) with variably promising results (26, 31-33). Like the mentioned human inflammatory mucosal lesions, FCGS is characterized by CD8 T cell inflammation and a dysregulated immune response (8, 9), The ability of MSCs to inhibit T cell proliferation and induce T cell anergy suggested that FCGS may be a promising disease target for MSC therapy and a possible animal model that mimics chronic human oral lesions.

The purpose of this study was to evaluate the clinical, histopathological and immunologic effects resulting from systemic administration of fresh, autologous ASCs in a cohort of cats affected by FCGS that did not respond to previous conventional therapy. We hypothesized that ASC therapy would result in systemic immune modulation, reduction of the inflammatory lesions, and improvement of clinical signs. We found that ASCs administered systemically resulted in complete clinical remission or substantial clinical improvement in 5 of the 7 cats. This improvement was correlated with systemic immune modulation and reduced inflammatory lesions. Cats who responded to ASC therapy had increased percentages of circulating total CD8 T cells and decreased percentages of CD8lo cells prior to therapy suggesting that circulating CD8+ T cells and CD8 T cell subsets may be promising biomarkers for patient selection, monitoring response to therapy and elucidating how ASCs modulate oral inflammation and decrease T cell activation.

SUMMARY

In one aspect, provided is a method of preventing, reducing, mitigating, ameliorating and/or reversing inflammation in a mammal in need thereof. In some embodiments, the methods comprise:
a) measuring the level of CD8lo T cells in a biological sample from the mammal, wherein the biological sample comprises CD8+ T cells; and
b) administering to the mammal an effective amount of mesenchymal stem cells (MSCs) when the level of CD8lo T cells in the biological sample is below a predetermined threshold level. In varying embodiments, the MSCs are adipose-derived mesenchymal stem cells (AdMSCs).

In a further aspect, provided is a method of preventing, reducing, mitigating, ameliorating and/or reversing oral inflammation in a mammal in need thereof. In some embodiments, the methods comprise:
 a) measuring the level of CD8lo T cells in a biological sample from the mammal, wherein the biological sample comprises CD8+ T cells;
 b) identifying a level of CD8lo T cells in the biological sample that is below a predetermined threshold level;
 c) isolating mesenchymal stem cells from or receiving mesenchymal stem cells isolated from adipose tissue obtained from the mammal, thereby obtaining adipose-derived mesenchymal stem cells (AdMSCs); and
 d) administering to the mammal an effective amount of the adipose-derived mesenchymal stem cells (MSCs).

In another aspect, provided is a method of preventing, reducing, mitigating, ameliorating and/or reversing gingivostomatitis in a feline in need thereof. In some embodiments, the methods comprise:

a) measuring the level of CD8lo T cells in a biological sample from the feline, wherein the biological sample comprises CD8+ T cells;
b) identifying a level of CD8lo T cells in the biological sample that is below a threshold level;
c) isolating mesenchymal stem cells from or receiving mesenchymal stem cells isolated from adipose tissue obtained from the feline, thereby obtaining adipose-derived mesenchymal stem cells (AdMSCs); and
d) administering to the feline an effective amount of the adipose-derived mesenchymal stem cells (MSCs).

With respect to embodiments of the methods of treatment, in varying embodiments, the predetermined threshold level is in the range of about 0% to about 25% CD8lo T cells of total CD8+ T cells, e.g., about 0% to about 25%, e.g., about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22% 23%, 24% or 25%. In varying embodiments, the CD8lo T cells express cell surface CD8 αβ heterodimer at a level that is about 20% to 80% of CD8+ T cells, e.g., at a level that is about 20% to about 30%, 35%, 40%, 45%, 50%, 55%, 60%, 65%, 70%, 75% or 80% of CD8+ T cells. In varying embodiments, CD8lo T cells express cell surface CD57 (e.g., are CD57+). In varying embodiments, CD8lo T cells do not express cell surface CD28 (e.g., are CD28−). In varying embodiments, CD8lo cells express FoxP3 (e.g., are FoxP3+). In varying embodiments, CD8lo cells express CD25 (e.g., are CD25+). In varying embodiments, the biological sample is blood. In varying embodiments, the mammal is a feline. In varying embodiments, the inflammation is oral inflammation. In varying embodiments, the oral inflammation is chronic. In varying embodiments, the oral inflammation is a condition selected from the group consisting of gingivostomatitis, recurrent apthous stomatitis, oral lichen planus, oral graft-versus-host disease, oral Crohn's disease, oral vesiculobullous disease, pemphigus and pemphigoid. In varying embodiments, the MSCs are autologous to the mammal (e.g., autologous to the feline). In varying embodiments, the MSCs are syngeneic to the mammal (e.g., syngeneic to the feline). In varying embodiments, the MSCs are allogeneic to the mammal (e.g., allogeneic feline). In varying embodiments, the MSCs are xenogeneic to the mammal (e.g., xenogeneic to the feline). In varying embodiments, the MSCs are positive for CD44, CD90 and CD105 (e.g., are CD44+, CD90+ and CD105+ and negative for CD34−, CD45− and MHC class II (e.g., are CD34−, CD45− and MHC class II−). In varying embodiments, the MSCs have not been frozen. In varying embodiments, the MSCs are fresh (i.e., not frozen) and viable. In varying embodiments, the MSCs are a population of cells that is at least about 50% viable. In varying embodiments, the MSCs have been cultured in vitro for at least 1 passage. In varying embodiments, the MSCs have been cultured in serum-free cell culture media. In varying embodiments, the MSCs have been cultured in cell culture media comprising serum proteins allogeneic to the mammal (e.g., allogeneic to the feline). In varying embodiments, the MSCs have been cultured in cell culture media comprising serum proteins xenogeneic to the mammal (e.g., xenogeneic to the feline, e.g., cultured in cell culture media comprising fetal bovine serum). In varying embodiments, the MSCs are substantially free of serum proteins xenogeneic to the mammal (e.g., substantially free of serum proteins xenogeneic to the feline). In varying embodiments, the MSCs are substantially free of bovine serum proteins. In varying embodiments, at least about 1 million MSCs/kg subject are administered. In varying embodiments, about 1 million to about 10 million MSCs/kg subject are administered. In varying embodiments, at least about 5 million MSCs are administered. In varying embodiments, about 5 million to about 100 million MSCs are administered. In varying embodiments, the MSCs are administered at a rate of about 1 million to about 10 million cells per minute. In varying embodiments, the mammal (e.g., feline) is exhibiting symptoms of oral inflammation, e.g., gingivostomatitis, recurrent apthous stomatitis, oral lichen planus, oral graft-versus-host disease, oral Crohn's disease, oral vesiculobullous disease, pemphigus or pemphigoid. In varying embodiments, the MSCs are administered systemically. In varying embodiments, the MSCs are administered intravenously. In varying embodiments, the MSCs are administered intralesionally. In varying embodiments, the MSCs are administered in multiple administrations. In varying embodiments, the mammal has a CD4/CD8 ratio in blood that is less than about 1.0 prior to administration of the MSCs and a CD4/CD8 ratio in blood that is greater than about 1.3 after one or more administrations of the MSCs.

In a further aspect, provided is a method of determining whether a mammalian subject having an inflammatory condition will respond positively to mesenchymal stem cell (MSC) therapy. In some embodiments, the methods comprise:
(a) obtaining a biological sample comprising CD8+ T cells from the mammal;
(b) detecting the level of CD8lo T cells in the biological sample, whereby a level of CD8lo T cells in the biological sample below a predetermined threshold level is indicative that the inflammation in the subject is likely to be reduced, mitigated, ameliorated, inhibited and/or eliminated by MSC therapy; and
(c) characterizing the subject as likely or not likely to respond to MSC therapy to treat the inflammation in the subject.

In another aspect, provided is a method for determining whether a mammalian subject having an inflammatory condition will respond positively to mesenchymal stem cell (MSC) therapy. In some embodiments, the methods comprise:
(a) obtaining a biological sample comprising CD8+T cells from the subject;
(b) detecting the level of CD8lo T cells in the biological sample, wherein detecting the level of CD8lO T cells is by application of flow cytometry; and
(c) comparing the level of CD8lo T cells in the biological sample to a predetermined threshold level, whereby a level of CD8lo T cells in the biological sample below a predetermined threshold level indicatives that the inflammation in the subject is likely to be reduced, mitigated, ameliorated, inhibited and/or eliminated by MSC therapy.

With respect to the diagnostic methods or methods of determining, in some embodiments, the predetermined threshold level is in the range of about 0% to about 25% CD8lo T cells of total CD8+ T cells. T cells, e.g., about 0% to about 25%, e.g., about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22% 23%, 24% or 25%. In varying embodiments, the CD8lo T cells express cell surface CD8 αβ heterodimer at a level that is about 20% to 80% of CD8+ T cells, e.g., at a level that is about 20% to about 30%, 35%, 40%, 45%, 50%, 55%, 60%, 65%, 70%, 75% or 80% of CD8+ T cells. In varying embodiments, CD8lo T cells express cell surface CD57 (e.g., are CD57+). In varying embodiments, CD8lo T cells do not express cell surface CD28 (e.g., are CD28−). In varying embodiments, CD8lo cells express FoxP3 (e.g., are FoxP3 +). In varying embodiments, CD8lo cells express CD25 (e.g., are CD25+). In varying embodiments, the biological sample is blood. In varying embodiments, the mammal is a feline. In varying embodiments, the inflammation is oral inflammation. In varying embodiments, the oral inflammation is chronic. In varying embodiments, the oral inflammation is a condition selected from the group consisting of gingivostomatitis, recurrent apthous stomatitis, oral lichen planus, oral graft-versus-host disease, oral Crohn's disease, oral vesiculobullous disease, pemphigus and pemphigoid. In varying embodiments, the mammal is exhibiting symptoms of oral inflammation. In varying embodiments, the mammal has a CD4/CD8 ratio in blood that is less than about 1.0 prior to administration of the MSCs.

In a further aspect, provided are methods for determining whether mesenchymal stem cell (MSC) therapy is or was efficacious in a mammalian subject having an inflammatory condition, comprising:
(a) obtaining a biological sample comprising CD8+T cells from the subject who has been administered MSCs;
(b) detecting the level of CD8lo T cells in the biological sample, wherein detecting the level of CD8lo T cells is by application of flow cytometry; and
(c) comparing the level of CD8lo T cells in the biological sample to a predetermined threshold level, whereby a level of CD8lo T cells in the biological sample above a predetermined threshold level indicatives that the inflammation in the subject is likely to be reduced, mitigated, ameliorated, inhibited and/or eliminated by MSC therapy. In varying embodiments, the biological sample is obtained at least 1 month after the MSCs were administered. In varying embodiments, the predetermined threshold level is at least about a 1.2-fold increase, e.g., in the range of about in the range of about 1.2-fold to about 4-fold CD8lo T cells, e.g., at least about 1.25-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold, 3.5-fold, 3.6-fold, 3.7-fold, 3.8-fold, 3.9-fold or 4.0-fold increase, in the level of CD8lo T cells after one or more administrations of MSCs in comparison to the baseline level of CD8lo T cells in a biological sample from the same tissue prior to administration of MSCs. In varying embodiments, the CD8lo T cells express cell surface CD8 αβ heterodimer at a level that is about 20% to 80% of CD8+ T cells. In varying embodiments, the CD8lo T cells express cell surface CD57. In varying embodiments, the CD8lo T cells do not express cell surface CD28. In varying embodiments, the CD8lo T cells express cell surface FoxP3. In varying embodiments, the CD8lo T cells express cell surface CD25. In varying embodiments, the biological sample is blood. In varying embodiments, the mammal is a feline. In varying embodiments, the inflammation is oral inflammation. In varying embodiments, the oral inflammation is chronic. In varying embodiments, the oral inflammation is a condition selected from the group consisting of gingivostomatitis, recurrent apthous stomatitis, oral lichen planus, oral graft-versus-host disease, oral Crohn's disease, oral vesiculobullous disease, pemphigus and pemphigoid. In varying embodiments, the mammal is exhibiting symptoms of oral inflammation. In varying embodiments, the mammal has a CD4/CD8 ratio in blood that is less than about 1.0 prior to administration of the MSCs.

Definitions

The terms "individual," "patient,", "subject" interchangeably refer to a mammal, for example, a human, a non-human primate, a domesticated mammal (e.g., a canine or a feline), an agricultural mammal (e.g., equine, bovine, ovine, porcine), or a laboratory mammal (e.g., rattus, murine, Lagomorpha, hamster).

As used herein, the terms "treating" and "treatment" refer to delaying the onset of, retarding or reversing the progress of, reducing the severity of, or alleviating or preventing either the disease or condition to which the term applies (i.e., oral inflammation, e.g., chronic oral inflammation, e.g., gingivostomatitis, stomatitis, glossitis, mucositis), or one or more symptoms of such disease or condition.

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

The term "effective amount" or "therapeutically effective amount" refers to the amount of an active agent sufficient to induce a desired biological result (e.g., prevention, delay, reduction or inhibition of one or more symptoms of an oral inflammation, e.g., chronic oral inflammation, e.g., gingivostomatitis, stomatitis, glossitis, mucositis). That result may be alleviation of the signs, symptoms, or causes of a disease, or any other desired alteration of a biological system. The term "therapeutically effective amount" is used herein to denote any amount of the formulation which causes a substantial improvement in a disease condition when administered once or multiple times over a period of time. The amount will vary with the condition being treated, the stage of advancement of the condition, and the type and concentration of formulation applied. Appropriate amounts in any given instance will be readily apparent to those skilled in the art or capable of determination by routine experimentation.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "inhibiting," "reducing," "decreasing" with respect to oral inflammation refers to inhibiting one or more symptoms of the oral inflammation in a subject by a measurable amount using any method known in the art (e.g., visual inspection for amelioration of inflammatory lesions (increased healing/decreased inflammation), e.g., in the oral cavity, e.g., maxillary buccal mucosa, mandibular buccal mucosa, maxillary attached gingiva, mandibular attached gingiva, molar salivary gland, areas lateral to palatoglossal folds, oropharyngeal tissue, lingual and/or sublingual tissues), changes in blood markers (e.g., a CD4/CD8 ratio in blood that is greater than about 1.3), and behavioral changes in the subject (e.g., appetite, the ability to eat solid foods, grooming, sociability, activity levels, weight gain, exhibition of increased comfort). The one or more symptoms of oral inflammation are inhibited, reduced or decreased if the measurable parameter of the one or more symptoms is at least about 10%, 20%, 30%, 50%, 80%, or 100% reduced in comparison to the measurable parameter of the one or more symptoms prior to administration of the MSCs. In some embodiments, the measurable parameter of the one or more symptoms is inhibited, reduced or decreased by at least about 1-fold, 2-fold, 3-fold, 4-fold, or more in comparison to the measurable parameter of the one or more symptoms prior to administration of the MSCs.

The term "mesenchymal stem cells" refers to stem cells defined by their capacity to differentiate into bone, cartilage, and adipose tissue. With respect to cell surface markers, MSCs generally express CD44, CD90 and CD105, and do not express CD4, CD34, CD45, CD80, CD86 or MHC-H.

The term "CD8lo T cells" refers to T cells that express cell surface CD57 (e.g., are CD57+) and express cell surface CD8 heterodimer at a level that is about 20% to 80% of CD8+ T cells.

As used herein, "administering" refers to local and/or systemic administration, e.g., including enteral and parenteral administration. Routes of administration for the MSCs that find use in the present invention include, e.g., administration as a suppository, intravenous ("iv"), intraperitoneal ("ip"), intramuscular ("im"), intralesional, intranasal, or subcutaneous ("sc") administration. Administration may also be local to the target or damaged tissue, e.g., to oral tissues including the oral mucosa and/or gingival tissue. Administration can be by any appropriate route such that the immunosuppressive agents secreted by the MSCs prevent, reduce or inhibit destruction or damage to the target tissue, e.g., the oral mucosa, the gingiva and other tissues in the oral cavity. Parenteral administration includes, e.g., intravenous, intramuscular, intra-arteriole, intraventricular, intradermal, subcutaneous, intraperitoneal, and intrarectal.

The terms "systemic administration" and "systemically administered" refer to a method of administering a compound or composition to a mammal so that the MSCs delivered to sites in the body, including the targeted site of pharmacological action, via the circulatory system. Systemic administration includes, e.g., intravenous, intra-arteriole, intraventricular intradermal, subcutaneous, intraperitoneal, and rectal administration.

The term "co-administer" and "co-administering" and variants thereof refer to the simultaneous presence of two or more active agents in the blood of an individual. The active agents that are co-administered can be concurrently or sequentially delivered.

The phrase "cause to be administered" refers to the actions taken by a medical professional (e.g., a physician), or a person controlling medical care of a subject, that control and/or permit the administration of the agent(s)/compound(s)/cell(s) at issue to the subject. Causing to be administered can involve diagnosis and/or determination of an appropriate therapeutic or prophylactic regimen, and/or prescribing particular agent(s)/compounds/cell(s) for a subject. Such prescribing can include, for example, drafting a prescription form, annotating a medical record, and the like.

The term "feline" refers to an animal that is a member of the family Felidae; including without limitation the subfamilies, Felinae, Pantherinae, and Acinonychinae; the genera *Caracal, Catopuma, Felis, Herpailurus, Leopardus, Leptailurus, Lynx, Oncifelis, Oreailurus, Otocolobus, Prionailurus, Profelis, Puma, Neofelis, Panthera, Pardofelis, and Uncia;* the species *felis, lybica, jubatus, caracal, badia, bieti, chaus, margarita, nigripes, silvestris, gordonii, yaguarondi, pardalis, tigrinus, wiedi, serval, canadensis, lynx, pardinus, rufus, colocolo, geoffroyi, guigna, jacobita, manul, bengalensis, planiceps, rubiginosus, viverrinus, aurata, concolor, nebulosa, leo, onca, pardus, tigris, marmorata,* and *uncial.*

BRIEF DESCRIPTION OF THE DRAWINGS

FIGS. 3A-C illustrate clinical measure of disease severity. (A) All cats had severe oral mucosal inflammation at the caudal oral cavity (A1, B1, C1). Clinical response among the responder cats was characterized by either complete clinical remission (A2) in 3 cats, and substantial clinical improvement in 2 cats (B2). No response was observed in 2 cats (C2). The stomatitis activity disease index (SDAI) was used to score disease severity of all cats that completed the study. (B) Table showing the SDAI scores at entry and at exit of the study with a calculation of percent recovery, non-responders are grey and italicized (cats number 4 and 7). (C) Graph of SDAI scores at entry and exit indicating 5 responding cats (black circles) and two non-responding cats (open boxes).

FIGS. 5A-F illustrate circulating inflammatory cells and serum immunoglobulins. Flow cytometric analysis of whole blood for CD4 (A), CD8 (B), and neutrophils (D), including the calculated ratio of CD4 to CD8 T cells (C). Globulin (E) and IgA (F) concentrations were measured in serum. Patterned grey bars represent standard reference intervals obtained from UC Davis reference intervals (D and E), plain grey bars represent the range values of control cats (n=6) which were used for parameters that did not have standard reference intervals (A, B, C and F). Responding cats (black circles); non-responding cats (open boxes).

FIGS. 6A-E illustrate low numbers of a subset of CD8+ cells (CD8lo) predict response to ASC therapy and normalize after treatment. CD8+ T cells can be divided into CD8hi and CD8lo populations. (A, B, and C) Representative flow cytometry gating scheme for CD8+ and CD8lo populations for (A) control non-FCGS cat, (B) responder FCGS affected cat, and (C) non-responder FCGS affected cat, including the percent of total lymphocytes that were CD8+, and the percent of CD8+ cells that were CD8lo. (D) Summary of CD8lo percentages of CD8+ cells based on flow cytometry gates above for all cats in the study. Responder cats had a lower percentage of CD8lo cells before ASC treatment than at 6 months after (Multiple comparisons 2 way ANOVA, p<0.05). (E) Comparison of the percent of CD8+ cells that were CD8lo in responder and non-responder groups before ASC treatment for use as a biomarker to predict response to treatment, responders had a lower percentage of CD8+ cells that were CD8lo than non-responders (unpaired t-test, p=0.04). Responding cats (black circles); non-responding cats (open boxes).

FIGS. 7A-D illustrate serum cytokines. Serum cytokines were variably detectable in all cats in the study. ELISA results for serum levels of IL-6 (A), IFNγ (B), TNFα (C) and IL-1β (D). Note that one non-responder showed very high expression of most serum cytokines indicating a severe systemic pro-inflammatory state. Responding cats (black circles); non-responding cats (open boxes).

FIGS. 8A-I illustrate that, like human ASCs, feline ASCs meet the basic defining criteria of mesenchymal stem cells. Feline (A) and human (B) ASCs adhere to plastic and have a spindle, fibroblast morphology in culture. However, human ASCs are significantly larger than feline ASCs (C). Both feline (D) and human (E) ASCs have a normal karyotype. Feline (F) and human (G) ASCs both have positive surface expression of CD44, CD90 and CD105 and are negative for surface expression of CD45 (pan leukocyte, human) or CD18 (pan leukocyte, feline) and MHC H. Both feline (H) and human (I) ASCs undergo osteogenic differentiation. Cell size presented as mean and standard error. *P<0.05, P<0.01, *P<0.001.

FIGS. 9A-C illustrate that human and feline ASCs display similar proliferative capacity and immune-suppressive functions. Doubling times were calculated for feline ASCs at passage 2-6 and for human ASCs at passage 3-6. The proliferation rate of human and feline ASCs is comparable throughout multiple passages (A). Feline ASCs co-incubated with stimulated PBMCs maintain immune-suppressive function regardless of direct contact (transwells) (B). Human ASCs similarly inhibit PHA induced lymphocyte proliferation, however direct contact with stimulated PBMCs leads to stronger inhibition than the transwell condition (C). Data presented as mean and standard error. *P<0.05, P<0.01, *P<0.001.

FIGS. 10A-H illustrate that MSCs in an inflammatory environment become activated and produce regulatory mediators. Indoleamine 2,3-dioxygenase (IDO) is an enzyme involved in the kynurenine pathway that breaks down tryptophan. Depletion of tryptophan in turn decreases the proliferation of lymphocytes. Feline ASCs in the presence of proliferating PBMCs increase IDO activity (A). A trend of increased IDO activity was observed by stimulated human ASCs, but was not statistically significant (B). Next, transwells were included in co-culture conditions to determine if contact was required for the production of MSC mediators. Production of PGE2 occurred in both standard and transwell conditions in cats, however greater production occurred when feline ASCs were in direct contact with stimulated PBMCs (C). Human ASCs produce PGE2 to the same magnitude with or without contact to stimulated PBMCs (D). IL6 was significantly upregulated regardless of contact for both feline (E) and human (F) ASC co-cultures. Production of VEGF occurred above baseline MSC secretion in standard and transwell conditions in cats (G). However, VEGF was not significantly increased above baseline by stimulated human ASCs (H). Data presented as mean and standard error. *P<0.05, P<0.01, *P<0.001.

FIGS. 11A-D illustrate that several regulatory mediators produced by activated MSCs are also secreted by a multitude of cells in peripheral blood. Baseline production by activated PBMCs may contribute to the upregulation of these mediators when co-cultured with MSCs. Production of IL8 by feline ASCs, is significantly increased regardless of contact with stimulated PMBCs (A). IL8 is also produced by stimulated human ASCs without contact, but is not quite significant when in direct contact with activated PBMCs (p=0.08). Human ASCs co-cultured directly with stimulated PBMCs yield higher concentrations of IL8 than in the transwell condition (B), Production of TGFβ by activated MSCs is not altered from baseline expression regardless of contact in both cats (C) and humans (D). Data presented as mean and standard error. *P<0.05, P<0.01, *P<0.001.

FIGS. 12A-F illustrate that activated MSCs provide immunoregulatory properties in part by downregulating the production of inflammatory mediators. Feline ASCs in the presence of proliferating lymphocytes do not inhibit production of IFNγ. Removal of direct contact between. ASCs and stimulated PBMCs lead to a significant reduction of IFNγ production (A). Human ASCs in contact with PBMCs stimulated with PHA inhibit production of IFNγ. However, when contact with activated PBMCs is removed, inhibition of IFNγ does not occur (B). Feline ASCs also inhibit production of TNFα with or without contact, with the transwell condition inhibiting production of the mediator to a greater extent (C). Human ASCs inhibit production of TNFα regardless of contact with proliferating lymphocytes (D). Production of IL10 in feline ASC lymphocyte co-cultures, increase significantly without contact and is not quite significant when contact occurs (p=0.06, E). No alterations of IL10 production were observed by activated human ASCs (F). Data presented as mean and standard error. *P<0.05, P<0.01, *P<0.001.

DETAILED DESCRIPTION

1. Introduction

Figure 1A:
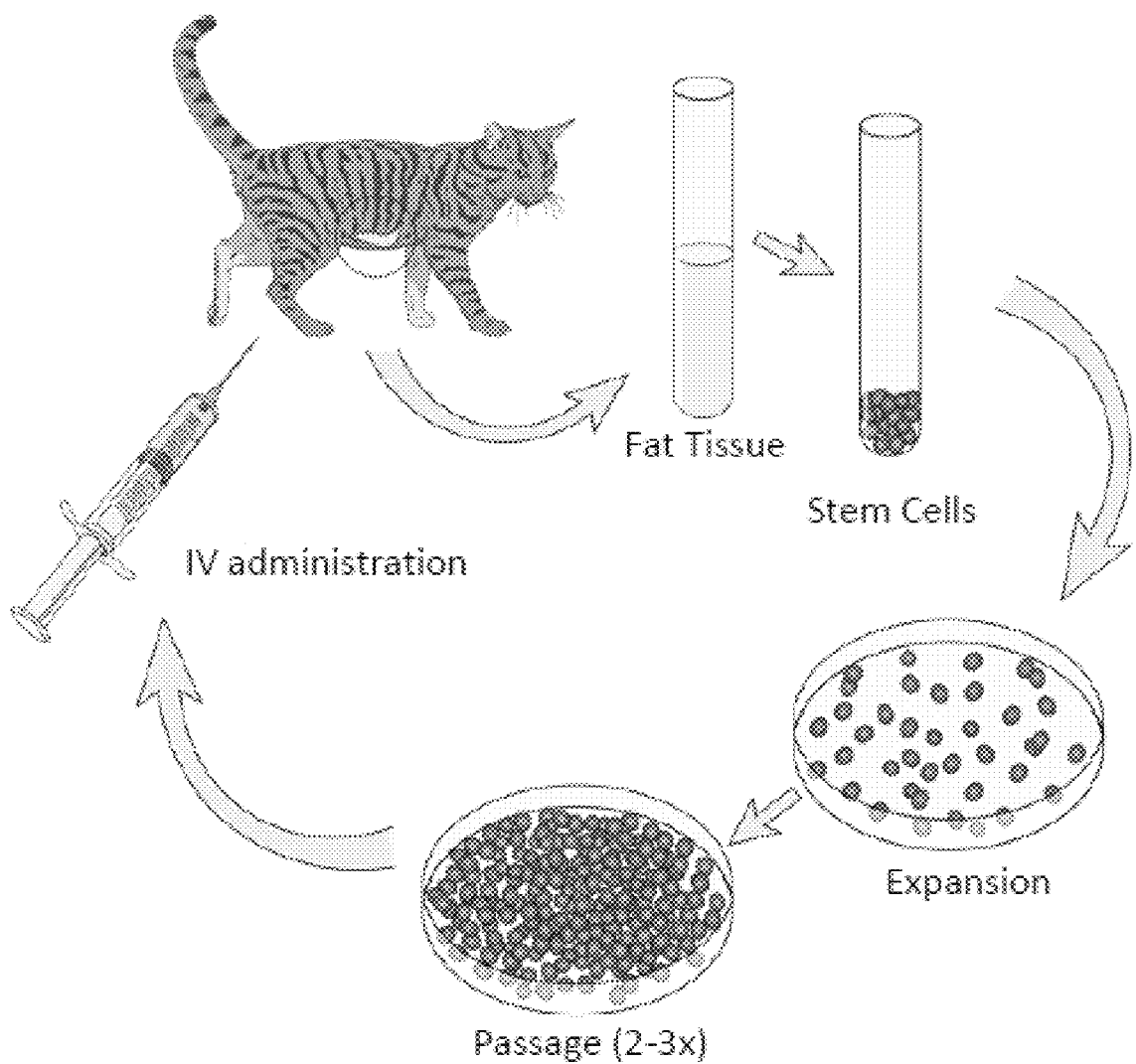
FIGS. 1A-B illustrate a study design (A) and timeline (B).

Mesenchymal stem cells (MSCs) are a promising therapy for immune-mediated and inflammatory disorders due to their potent immunomodulatory properties. The present methods are based, in part, on the use of fresh, autologous, adipose-derived MSCs (ASCs) for feline chronic gingivostomatitis (FCGS), a chronic, debilitating, idiopathic oral mucosal inflammatory disease. Nine cats with refractory FCGS were enrolled in this study. In the illustrative protocol, each cat received 2 intravenous injections of 20 million autologous ASCs, 1 month apart. Oral biopsies were taken prior to and at 6 months after the first ASC injection. Blood immune cell subsets, serum proteins and cytokine levels were measured at 0, 1, 3 and 6 months after treatment to assess immunomodulatory effects. Seven out of 9 cats completed the study. Five cats responded to treatment by either complete clinical remission (n=3) or substantial clinical improvement (n=2). Two cats were non-responders. Cats that responded to treatment also exhibited systemic immunomodulation demonstrated by decreased circulating CD8+ T cells, a normalization of the CD4/CD8 ratio, decreased neutrophil counts, and IFN-γ and IL-1β concentration, and a temporary increase in serum IL-6 and TNFα concentration. No clinical recurrence has occurred following complete clinical remission (follow up of 6-24 months). In this study, it was surprisingly discovered that cats with <15% CD8lo cells were 100% responsive to ASC therapy whereas cats with >15% CD8lo cells were non-responders. Moreover, the relative absence of CD8lo cells serves as a biomarker to predict response to ASC therapy, and sheds light on pathogenesis of FCGS and mechanisms by which ASCs decrease oral inflammation and affect T cell phenotype.

2. Subjects Who Can Benefit

The present methods can prevent, reduce, mitigate, ameliorate and/or reverse inflammation in any mammal suffering from or at risk of suffering from an inflammatory disorder, including an oral inflammation, e.g., a persistent, chronic, recalcitrant and/or otherwise untreatable oral inflammation. Illustrative oral inflammatory conditions that can be treated with MSCs and determined as amenable to treatment with MSCs include without limitation, gingivostomatitis, stomatitis, glossitis, mucositis, recurrent apthous stomatitis, oral lichen planus, oral graft-versus-host disease, oral Crohn's disease, oral vesiculobullous disease, pemphigus and pemphigoid. The mammal may or may not be exhibiting symptoms of oral inflammation. In cases where the inflammation is in remission, the mammal may not be exhibiting symptoms. In other cases, the mammal may be suffering active inflammation, e.g., that impedes the ability to eat and/or has resulted in tooth extractions.

In varying embodiments, the methods find use in preventing, reducing, mitigating, ameliorating and/or reversing inflammation, including oral inflammation, in a mammalian subject, e.g., humans and non-human mammals. Illustrative non-human mammals include without limitation e.g., Felidae (e.g., domesticated cat, cheetah, ocelot, lynx, bobcat, mountain lion, leopard, puma, lion, jaguar, tiger), Equidae (e.g., horse, ass, zebra), Bovidae (e.g., cattle, bison, sheep, goat, yak, impala, antelope, hartebeest, wildebeest, gnu, gazelle, water buffalo, duiker), Cervidae (e.g., deer, elk, moose, reindeer, pudu, bororo, brocket, guemal, muntjac), Suidae (e.g., pig, hog, boar), Canidae (domesticated dog, wolf, fox, coyote, jackal), Rodentia (e.g., mouse, rat, guinea pig, chinchilla, agouti, porcupine, beaver, gopher), Lagomorpha (e.g., rabbit, jackrabbit, hare, pika), Camelidae (e.g., camel, llama, alpaca, guanaco, vicugna), Ursidae (e.g., bear, panda), Procyonidae (e.g., raccoon, coati, olingo), Mustelidae (polecat, weasel, ferret, mink, fisher, badger, otter, wolverine, marten, sable, ermine), Elephantidae (e.g., elephant), rhinoceros, hippopotamus and non-human primates (e.g, chimpanzee, bonobo, macaque, ape).

In varying embodiments, the subject is a feline. The feline can be domesticated or non-domesticated. The domesticated feline can be a domestic short hair, domestic medium hair or domestic long hair. Certain breeds of domesticated cats are more susceptible to developing oral inflammation, e.g., a persistent, chronic, recalcitrant and/or otherwise untreatable oral inflammation, e.g., gingivostomatitis, stomatitis, glossitis and/or mucositis. Illustrative breeds of domesticated cats particularly susceptible to the development of oral inflammation, e.g., feline chronic gingivostomatitis, include without limitation Siamese, Abyssinians, Persians, Himalayans and Burmese. Illustrative breeds of domesticated cats that can benefit from the present methods include without limitation, Abyssinian, American Bobtail, American Bobtail Shorthair (SH), American Curl, American Curl Longhair (LH), American Shorthair, American Wirehair, Balinese, Bengal, Birman, Bombay, British Shorthair, British Longhair, Burmese, Chartreux, Colorpoint Shorthair, Cornish Rex, Cymric, Devon Rex, Egyptian Mau, European Burmese, Exotic Shorthair, Havana Brown, Himalayan, Japanese Bobtail, Japanese Bobtail Longhair, Korat, LaPerm, Maine Coon, Manx, Munchkin, Munchkin Longhair, Nebelung, Norwegian Forest Cat, Ocicat, Oriental Longhair, Oriental Shorthair, Persian, Peterbald, Pixiebob, Pixiebob Longhair, RagaMuffin, Ragdoll, Russian Blue, Scottish Fold, Scottish Fold Longhair, Selkirk Rex, Selkirk Rex Longhair, Siamese, Siberian, Singapura, Snowshoe, Somali, Sphynx, Thai, Tonkinese, Toyger, Turkish Angora, Turkish Van, Chausie, Savannah, Bambino, Donskey, Highlander, Highlander Shorthair, Kurilian Bobtail, Kurilian Bobtail Longhair, Minskin, Ojos Azules, Ojos Azules Longhair, Serengeti and Sokoke, and mixtures thereof. The felines can be pure breeds, partial breeds, mixed breeds or mongrels.

Patients amenable to treatment include individuals at risk of disease but not showing symptoms, as well as patients presently showing symptoms of inflammation, including oral inflammation.

In various methods of treatment, the subject may already exhibit symptoms of disease or be diagnosed as having inflammation, e.g., an oral inflammation, particularly a persistent, chronic, recalcitrant and/or otherwise untreatable oral inflammation, e.g., gingivostomatitis, stomatitis, glossitis and/or mucositis. For example, the subject may be exhibiting one or more symptoms, including inflammatory lesions in the oral cavity, e.g., maxillary buccal mucosa, mandibular buccal mucosa, maxillary attached gingiva, mandibular attached gingiva, molar salivary gland, areas lateral to palatoglossal folds, oropharyngeal tissue, lingual and/or sublingual tissues, changes in blood markers (e.g., a CD4/CD8 ratio in blood that is less than about 1.2), and/or behavioral changes in the subject (e.g., loss of appetite, the inability to eat solid foods, absent or reduced grooming, absent or reduced sociability, absent or reduced activity levels or exhibition of malaise, weight loss, exhibition of pain. In such cases, administration of MSCs can reverse or delay progression of and or reduce the severity of disease symptoms.

The effectiveness of treatment can be determined by comparing a baseline measure of a parameter of disease before administration of the MSCs is commenced to the same parameter one or more time points after MSCs have been administered. Illustrative parameters that can be measured include without limitation amelioration of inflammatory lesions in the oral cavity, e.g., maxillary buccal mucosa, mandibular buccal mucosa, maxillary attached gingiva, mandibular attached gingiva, molar salivary gland, areas lateral to palatoglossal folds, oropharyngeal tissue, lingual and/or sublingual tissues, changes in blood markers (e.g., a CD4/CD8 ratio in blood that is greater than about 1.3), and behavioral changes in the subject (e.g., appetite, the ability to eat solid foods, grooming, sociability, activity levels, weight gain, exhibition of increased comfort), as indicators that the treatment is effective.

For the purposes of prophylaxis, the subject may be asymptomatic but have a risk or predisposition to developing an oral inflammation or oral inflammatory disorder. In such cases, administration of MSCs can prevent or delay onset of disease or progression of oral inflammation into later stages of disease, and/or reduce the severity of the disease once present.

3. Identification of Subjects Having Blood CD8lo T Cells Above or Below Threshold Levels CD8lo T cells can be identified and quantified by flow cytometry. Generally, a biological sample (e.g., blood) is obtained from the subject, and the percentage of CD8lo T cells relative to the total population of CD8+ T cells is determined by flow cytometry. In running a biological sample through a flow cytometer, one first creates a gate on forward and side scatter (e.g., a lymphocyte gate) and determines the total CD8+ T cells within that gate. Then, a second gate is then created within the CD8+ gate. This second gate encompasses all the CD8+ cells that have greater fluorescence than lymphocytes stained with an irrelevant antibody (e.g., lymphocytes which are negative for CD8 expression) and continues up to the fluorescent edge of the lymphocytes that have high, uniform CD8 expression (e.g., CD8+ T cells). These first and second flow cytometry gates are depicted in FIGS. 6A-D. In varying embodiments, the CD8lo T cells express cell surface CD8 αβ heterodimer at a level that is about 20% to 80% of CD8+ T cells, e.g., at a level that is about 20% to about 30%, 35%, 40%, 45%, 50%, 55%, 60%, 65%, 70%, 75% or 80% of CD8+ T cells. In varying embodiments, CD8lo T cells express cell surface CD57 (e.g., are CD57+). In varying embodiments, CD8lo T cells do not express cell surface CD28 (e.g., are CD28−). In varying embodiments, CD8lo T cells are effector suppressor cells.

Cells from the biological sample can be prepared for flow cytometry in a manner that is appropriate to the biological sample. When the biological sample is whole blood, the lymphocytes can be separated from red blood cells using any method known in the art. For example, the red blood cells can be lysed and/or the lymphocytes can be concentrated or enriched by using density gradient centrifugation (e.g., a ficoll gradient) or using magnetic bead separation (e.g., beads conjugated to anti-CD8 antibodies or non-antibody binding proteins).

Subjects suffering from or experiencing an inflammatory condition who are likely to benefit from administration of mesenchymal stem cells have a level of CD8lo T cells in the biological sample (e.g., blood) that is below a predetermined threshold level prior to administration of MSCs. In varying embodiments, the predetermined threshold level is in the range of about 0% to about 25% CD8lo T cells of total CD8+ T cells, e.g., about 0% to about 25%, e.g., about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22% 23%, 24% or 25% CD8lo T cells of total CD8+ T cells.

Subjects suffering from or experiencing an inflammatory condition who are likely to benefit from administration of mesenchymal stem cells have a level of CD8lo T cells in the biological sample (e.g., blood) that is above a predetermined threshold level after administration of MSCs, e.g., 1, 2, 3, 4, 5, 6, 7, 8, 9, 10, 11, 12 months after administration of MSCs. In varying embodiments, the predetermined threshold level is in the range of about 1.2-fold to about 4-fold CD8lo T cells, e.g., at least about 1.2-fold, 1.25-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2,9-fold, 3.0-fold, 3.1-fold, 3.2-fold, 3.3-fold, 3.4-fold, 3.5-fold, 3.6-fold, 3.7-fold, 3.8-fold, 3.9-fold or 4.0-fold, measured at a time point after one or more administrations of MSCs in comparison to the baseline level of CD8lo T cells measured from the same tissue prior to administration of MSCs. Expressed in terms of percentages, in varying embodiments, the predetermined threshold level is in the range of about 120% to about 400% CD8lo T cells, e.g., at least about 120%, 125%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390% or 400%, measured at a time point after one or more administrations of MSCs in comparison to the baseline level of CD8lo T cells measured from the same tissue prior to administration of MSCs.

4. Preparation and Administration of Mesenchymal Stem Cells a. Mesenchymal Stem Cells The bone marrow and adipose tissue of an adult mammal is a repository of mesenchymal stem cells (MSCs). Bone marrow MSCs are self-renewing, clonal precursors of non-hematopoietic tissues. MSCs for use in the present methods can be isolated from a variety of tissues, including bone marrow, muscle, fat (i.e., adipose), liver, dermis, gingiva and periodontal ligament, using techniques known in the art. Illustrative techniques are described herein and reported in, e.g., Chung, et al., *Res Vet Sci*. (2012) 92(1):66-75; Toupadakis, et al., *Am J Vet Res*. (2010) 71(10):1237-45. Depending on the stimulus and the culture conditions employed, these cells can form bone, cartilage, tendon/ligament, muscle, marrow, adipose, and other connective tissues.

In some embodiments, the MSCs are derived from adipose tissue. Adipose-derived MSCs (AdMSCs) can be obtained from either autologous (self) and allogeneic (non-self) sources. The use of allogeneic MSCs in patients is possible due to their low immunogenicity. However, autologous AdMSCs are non-immunogenic and considered to be safe in people and animals. AdMSCs can be administered either systematically (e.g., intravenous or intraarterially) or locally (e.g., to any inflamed oral mucosa, e.g., into the gingiva, oral mucosal and/or periodontal tissues and/or other soft tissue of the oral cavity) in the treatment of disorders. Illustrative oral mucosal tissues that may be inflamed and ameliorated by local administration of MSCs include without limitation, e.g., maxillary buccal mucosa, mandibular buccal mucosa, maxillary attached gingiva, mandibular attached gingiva, molar salivary gland, areas lateral to palatoglossal folds, oropharyngeal tissue, lingual and/or sublingual tissues. MSCs can be generated more efficiently and rapidly from adipose tissue than from bone marrow. Fat- or adipose-derived MSCs are present in higher number and have a significantly higher proliferation rate then bone-marrow derived MSCs.

Generally, the MSCs useful for administration express on their cell surface CD44, CD90 and CD105 and do not express on their cell surface CD4, CD34, CD45, CD80, CD86 or MHC-II In various embodiments, the MSCs are adipose-derived mesenchymal stem cells (AdMSC). AdMSCs can be characterized by the surface expression of CD5, CD44, CD90 (Thy-1) and CD105; and by the non-expression of CD3, CD4, CD18, CD34, CD45, CD49d, CD80, CD86 and MHC class II. In other embodiments, the MSCs are derived from a non-adipose tissue, for example, bone marrow, liver, periodontal ligament, gingiva and/or dermal tissues. In some embodiments, the MSCs are non-hematopoietic stem cells derived from bone marrow (e.g., do not express CD34 or CD45).

As appropriate, the MSCs can be autologous (i.e., from the same subject), syngeneic (i.e., from a subject having an identical or closely similar genetic makeup); allogeneic (i.e., from a subject of the same species) or xenogeneic to the subject (i.e., from a subject of a different species).

In various embodiments, the MSCs may be altered to enhance the viability of engrafted or transplanted cells. For example, the MSCs can be engineered to overexpress or to constitutively express Akt. See, e.g., U.S. Patent Publication No. 2011/0091430.

b. Preparation

Tissue comprising MSCs is obtained and processed. As appropriate the tissue can be adipose, bone marrow, periodontal ligament, gingiva, muscle, liver or dermis. The obtained MSCs can be autologous, syngeneic, allogeneic or xenogeneic to the subject mammal. The tissue is processed to isolate the MSCs such that they can be cultured in vitro.

Solid tissues can be minced and digested with a proteinase (e.g., collagenase), as appropriate. In varying embodiments, the isolated MSCs can be cultured in vitro for at least 1 passage, e.g., from about 2 passages to about 8 passages, e.g. for 2, 3, 4, 5, 6, 7, 8 passages, as appropriate. In certain embodiments, the isolated MSCs are cultured in media comprising xenogeneic serum (e.g., feline or human MSCs are cultured in medium comprising fetal bovine serum).

In varying embodiments, at least 24 hours prior to injection into the subject, e.g., 24, 36 or 48 hours prior to injection, the cultured MSCs are washed and then cultured in media comprising serum of the same species of the subject mammal (e.g., autologous, syngeneic and/or allogeneic serum) and in the absence of serum xenogeneic to the subject mammal to wash out serum proteins allogeneic to the subject mammal in order to avoid or minimize the risk of a potential transfusion reaction. For example, the present MSCs can be substantially free of bovine and/or equine serum proteins prior to injection to a feline or canine subject. In some embodiments, the MSCs are cultured and/or resuspended in serum-free media. In certain embodiments, the isolated MSCs are cultured in media comprising xenogeneic serum (e.g., feline or human MSCs are cultured in medium comprising fetal bovine serum) and then the cells are washed prior to injection to remove serum proteins allogeneic to the subject mammal in order to avoid or minimize the risk of a potential transfusion reaction.

Prior to injection or engraftment into the subject mammal, the MSCs are rinsed and resuspended in a serum-free isotonic buffered solution (e.g., phosphate-buffered saline, 0.9% sodium chloride, lactated Ringer's solution (LRS), Hank's Balanced Salt Solution (HESS), Earle's Balanced Salt Solution (EBSS), etc.).

Generally, the MSCs administered to the subject are fresh (i.e., not frozen) and viable. In varying embodiments, the MSCs have been cultured in vitro for one or more passages prior to injection, so the administered MSCs have never been frozen. The MSCs are evaluated for viability prior to administration. In varying embodiments, the population of administered MSCs are at least about 50% viable, e.g., at least about 55%, 60%, 65%, 70%, 75%, 80%, 85%, 90%, 95%, 98%, 99%, 100% viable. In varying embodiments, for second and subsequent administrations, the original cells from the first administration are frozen, thawed, culture expanded as described above and administered fresh.

c. Administration

The MSCs can be administered by any appropriate route such that the anti-inflammatory and/or immunomodulatory factors secreted by the cells exert an anti-inflammatory and/or immune-inhibitory effect on the mediators of damage and/or destruction of the gingival and oral mucosal tissues and/or other soft tissues within the oral cavity. The anti-inflammatory and/or immune inhibitory effect can be local or systemic. In various embodiments, the MSCs are systemically administered, e.g., intravenously.

In some embodiments, the MSCs are administered locally, e.g., intralesionally, into the gingiva, oral mucosal and/or periodontal tissues and/or other soft tissue of the oral cavity. As appropriate, the MSCs can be engrafted or transplanted into and/or around the gingiva, oral mucosal and/or periodontal tissues and/or other soft tissues of the oral cavity. When engrafted or transplanted into and/or in the vicinity of one or more tissues of the oral cavity, the MSCs are administered within or within sufficient proximity of the inflamed lesions in the oral cavity to exert an anti-inflammatory and/or immune-inhibitory effect on the mediators of damage and/or destruction of the gingival and oral mucosal tissue. For example, the MSCs are engrafted or transplanted into or within sufficient proximity to the tissues of the oral cavity such that any anti-inflammatory and/or immunosuppressive factors secreted by the MSCs prevent, reduce or inhibit damage and/or destruction to the tissues of the oral cavity, e.g., the gingiva and/or the oral mucosal tissues. Depending on the stage or extent of oral inflammation, MSCs may be administered before or after tooth extractions. Administration of MSCs prior to tooth extraction may allow for prevention or avoidance of the necessity of tooth extraction.

As appropriate, injections of MSCs can be done after local anesthetics (e.g., lidocaine, bupivacaine) have been administered. It is also possible to inject the MSCs in conjunction with local anesthetics added to the cell suspension. Injections can also be made with the subject under general anesthesia with or without the use of local anesthetic agents (e.g., lidocaine).

In various embodiments, engraftment or transplantation of the MSCs can be facilitated using a matrix or caged depot. For example, the MSCs can be engrafted or transplanted in a "caged cell" delivery device wherein the cells are integrated into a biocompatible and/or biologically inert matrix (e.g. a hydrogel or other polymer or any device) that restricts cell movement while allowing the cells to remain viable. Synthetic extracellular matrix and other biocompatible vehicles for delivery, retention, growth, and differentiation of stem cells are known in the art and find use in the present methods. See, e.g., Prestwich, *J Control Release*. (2011) 155(2): 193-9; Perale, et al., *Int J Artif Organs*. (2011) 34(3):295-303; Suri, et al., *Tissue Eng* Part A. (2010) 16(5):1703-16; Khetan, et al., *J Vis Exp*. (2009) October 26; (32). pii: 1590; Salinas, et al., *J Dent Res*. (2009) 88(8): 681-92; Schmidt, et al., *J Biomed Mater Res* A. (2008) 87(4):1113-22 and Xin, et al., *Biomaterials* (2007) 28:316-325.

As appropriate or desired, the engrafted or transplanted MSCs can be modified to facilitate retention of the MSCs at the region of interest or the region of delivery. In other embodiments, the region of interest for engraftment or transplantation of the cells is modified in order to facilitate retention of the MSCs at the region of interest or the region of delivery. In one embodiment, this can be accomplished by introducing stromal cell derived factor-1 (SDF-1) into the region of interest, e.g., using linkage chemistry or integrated biodegradable matrix (e.g., poly(D,L-lactide-co-glycolide (PLGA) beads) that would provide a tunable temporal presence of the desired ligand up to several weeks. MSCs bind to the immobilized SDF-1, thereby facilitating the retention of MSCs that are delivered to the region of interest for engraftment or transplantation. In other embodiments, integrating cyclic arginine-glycine-aspartic acid peptide into the region of interest can facilitate increased MSC binding and retention at the region of interest for engraftment or transplantation. See, e.g., Ratliff, et al., *Am J Pathol*. (2010) 177(2):873-83.

In some embodiments, at least about 1 million MSCs/kg subject are administered or engrafted, e.g., at least about 2 million, 2.5 million, 3 million, 3.5 million, 4 million, 5 million, 6 million, 7 million, 8 million, 9 million or 10 million MSCs/kg subject are administered. In varying embodiments, about 1 million to about 10 million MSCs/kg subject, e.g., about 2 million to about 8 million MSCs/kg are administered or grafted.

In varying embodiments, at least about 5 million MSCs are administered or engrafted, e.g., at least about 10 million, 15 million, 20 million, 25 million, 30 million, 35 million, 40 million, 45 million, 50 million, 55 million, 60 million, 65 million, 70 million, 75 million, 80 million, 85 million, 90 million, 95 million or 100 million MSCs are administered or engrafted. In varying embodiments, about 5 million to about 100 million MSCs are administered or engrafted, e.g., about 10 million to about 80 million MSCs are administered or engrafted.

In varying embodiments, the MSCs are administered, e.g., intravenously, at a rate of about 1 million to about 10 million cells per minute, e.g., at a rate of about 2 million to about 4 million cells per minute, e.g., at a rate of about 2.5 million to about 3.5 million cells per minute.

A regime of treatment or prevention may involve one or multiple injections. For example, MSCs may be administered to the subject 1, 2, 3, 4, 5, 6, 7, 8, 9, 10, or more times, as appropriate. Subsequent administrations of MSCs may be administered systemically or locally. If administered locally, multiple injections of MSCs may be administered to the same or different locations. Multiple injections of MSCs can be administered daily, weekly, bi-weekly, monthly, bi-monthly, every 3, 4, 5, or 6 months, or annually, or more or less often, as needed by the subject. The frequency of administration of the MSCs can change over a course of treatment, e.g., depending on how well the engrafted or transplanted MSCs establish themselves at the site of administration and the responsiveness of the subject. The MSCs may be administered multiple times over a regime course of several weeks, several months, several years, or for the remainder of the life of the subject, as needed or appropriate.

The total amount of cells that are envisioned for use depend upon the desired effect, patient state, and the like, and may be determined by one skilled within the art. Dosages for any one patient depends upon many factors, including the patient's species, size, body surface area, age, the particular MSCs to be administered, sex, scheduling and route of administration, general health, and other drugs being administered concurrently.

Preparation and administration of MSCs, e.g., to feline subjects is described in Intl. Publ. No. WO2015/034660, which is hereby incorporated herein by reference in its entirety for all purposes.

5. Monitoring Efficacy

Clinical efficacy can be monitored using any method known in the art. Measurable parameters to monitor efficacy include, but are not limited to, visual inspection of amelioration of inflammatory lesions in the oral cavity, e.g., maxillary buccal mucosa, mandibular buccal mucosa, maxillary attached gingiva, mandibular attached gingiva, molar salivary gland, areas lateral to palatoglossal folds, oropharyngeal tissue, lingual and/or sublingual tissues), changes in blood markers (e.g., increased levels of CD8lo T cells, a CD4/CD8 ratio in blood that is greater than about 1.3), and behavioral changes in the subject (e.g., appetite, the ability to eat solid foods, grooming, sociability, activity levels, weight gain, exhibition of increased comfort). These parameters can be measured using any methods known in the art. The different parameters can be assigned a score, and the scores can be combined to provide a Stomatitis Disease Activity Index for the subject. Input can be provided by the client/caretaker/owner of the mammal and/or by self-reporting (in cases where the subject is a human) and/or by a trained clinician.

Observation of the stabilization, improvement and/or reversal of one or more symptoms or parameters by a measurable amount indicates that the treatment or prevention regime is efficacious. Observation of the progression, increase or exacerbation of one or more symptoms indicates that the treatment or prevention regime is not efficacious. For example, observation of the amelioration of one or more inflammatory lesions in the oral cavity, e.g., maxillary buccal mucosa, mandibular buccal mucosa, maxillary attached gingiva, mandibular attached gingiva, molar salivary gland, areas lateral to palatoglossal folds, oropharyngeal tissue, lingual and/or sublingual tissues), changes in blood markers (e.g., increased levels of CD8lo T cells, a CD4/CD8 ratio in blood that is greater than about 1.3), and behavioral changes in the subject (e.g., increased appetite, the ability to eat solid foods, improved/increased grooming, improved/increased sociability, improved/increased activity levels, weight gain and/or stabilization, exhibition of increased comfort) after one or more administrations of MSCs indicates that the treatment or prevention regime is efficacious. Likewise, observation of increased numbers or severity of inflammatory lesions in the oral cavity, e.g., maxillary buccal mucosa, mandibular buccal mucosa, maxillary attached gingiva, mandibular attached gingiva, molar salivary gland, areas lateral to palatoglossal folds, oropharyngeal tissue, lingual and/or sublingual tissues), changes in blood markers (e.g., decreased levels of CD8lo T cells (or a failure to increase), a CD4/CD8 ratio in blood that is less than about 1.2), and behavioral changes in the subject (e.g., decreased appetite, the inability to eat solid foods, reduced or absent grooming, reduced or absent sociability, reduced or absent activity levels, weight loss, exhibition of pain and/or malaise), after one or more administrations of MSCs indicates that the treatment or prevention regime was not efficacious.

As appropriate, efficacy can be monitored over 1, 2, 3, 4, 5, 6, 7, 8, 9, 10, 11, 12, 13, 14, 15, 16, 17, 18, 19, 20, 21, 22, 23, 24 months, or longer, e.g., 1, 1.5, 2, 2.5, 3, 3.5 or 4 years, or longer. In varying embodiments, efficacy may be observed after 1, 2, 3, 4, 5, 6, 7, 8, 9, 10, 11, 12, 13, 14, 15, 16, 17, 18, 19, 20, 21, 22, 23 or 24 months of treatment, with one or more administrations of MSCs.

In certain embodiments, the monitoring methods can entail determining a baseline value of a measurable biomarker or disease parameter in a subject before administering a dosage of the one or more active agents described herein, and comparing this with a value for the same measurable biomarker or parameter after a course of treatment.

In other methods, a control value (i.e., a mean and standard deviation) of the measurable biomarker or parameter is determined for a control population. In certain embodiments, the individuals in the control population have not received prior treatment and do not have an inflammatory disorder of the oral cavity (e.g., chronic oral inflammation, e.g., gingivostomatitis, stomatitis, glossitis, mucositis, recurrent apthous stomatitis, oral lichen planus, oral graft-versus-host disease, oral Crohn's disease, oral vesiculobullous disease, pemphigus and/or pemphigoid), nor are at risk of developing an inflammatory disorder of the oral cavity (e.g., chronic oral inflammation, e.g., gingivostomatitis, stomatitis, glossitis, mucositis, recurrent apthous stomatitis, oral lichen planus, oral graft-versus-host disease, oral Crohn's disease, oral vesiculobullous disease, pemphigus and/or pemphigoid). In such cases, if the value of the measurable biomarker or clinical parameter approaches the control value, then treatment is considered efficacious. In other embodiments, the individuals in the control population have not received prior treatment and have been diagnosed with an inflammatory disorder of the oral cavity (e.g., chronic oral inflammation, e.g., gingivostomatitis, stomatitis, glossitis, mucositis, recurrent apthous stomatitis, oral lichen planus, oral graft-versus-host disease, oral Crohn's disease, oral vesiculobullous disease, pemphigus and/or pemphigoid). In such cases, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and need not be resumed. In all of these cases, a significant difference relative to the control level (i.e., more than a standard deviation) is an indicator that treatment should be resumed in the subject.

EXAMPLES

The following examples are offered to illustrate, but not to limit the claimed invention.

Example 1

Therapeutic Efficacy of Fresh, Autologous Mesenchymal Stem Cells for Severe Refractory Gingivostomatitis in Cats Materials and Methods Study population. This study was conducted with approval of the Institutional Animal Care and Use Committee, and the Clinical Trials Review Board, University of California, Davis. All owners signed an informed consent. Nine client-owned cats with refractory FCGS, non-responsive to full-mouth tooth extractions and immunosuppressive therapies, were recruited to the study. Inclusion criteria included cats affected by FCGS only with no other primary co-morbidities that did not respond to full mouth extraction performed at least 6 months before enrollment. If corticosteroid or other immunosuppressive therapy was prescribed it had to be discontinued two weeks prior to and for the entire duration of the trial. Full-mouth dental radiographs were obtained to confirm the absence of retained root tips and to rule out any other underlying pathologies. All cats were screened and tested negative for feline immune deficiency virus and feline leukemia virus infection.

Figure 1B:
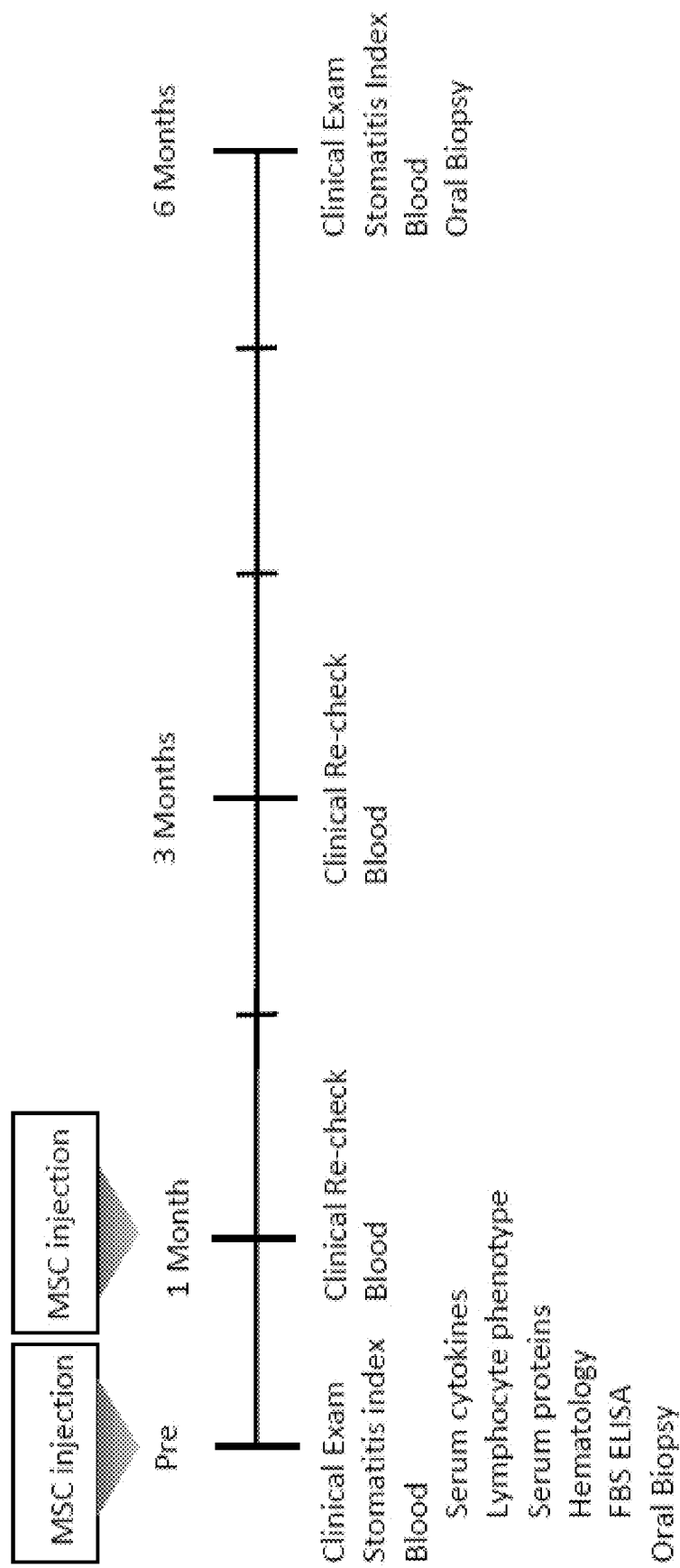
Figure 2:
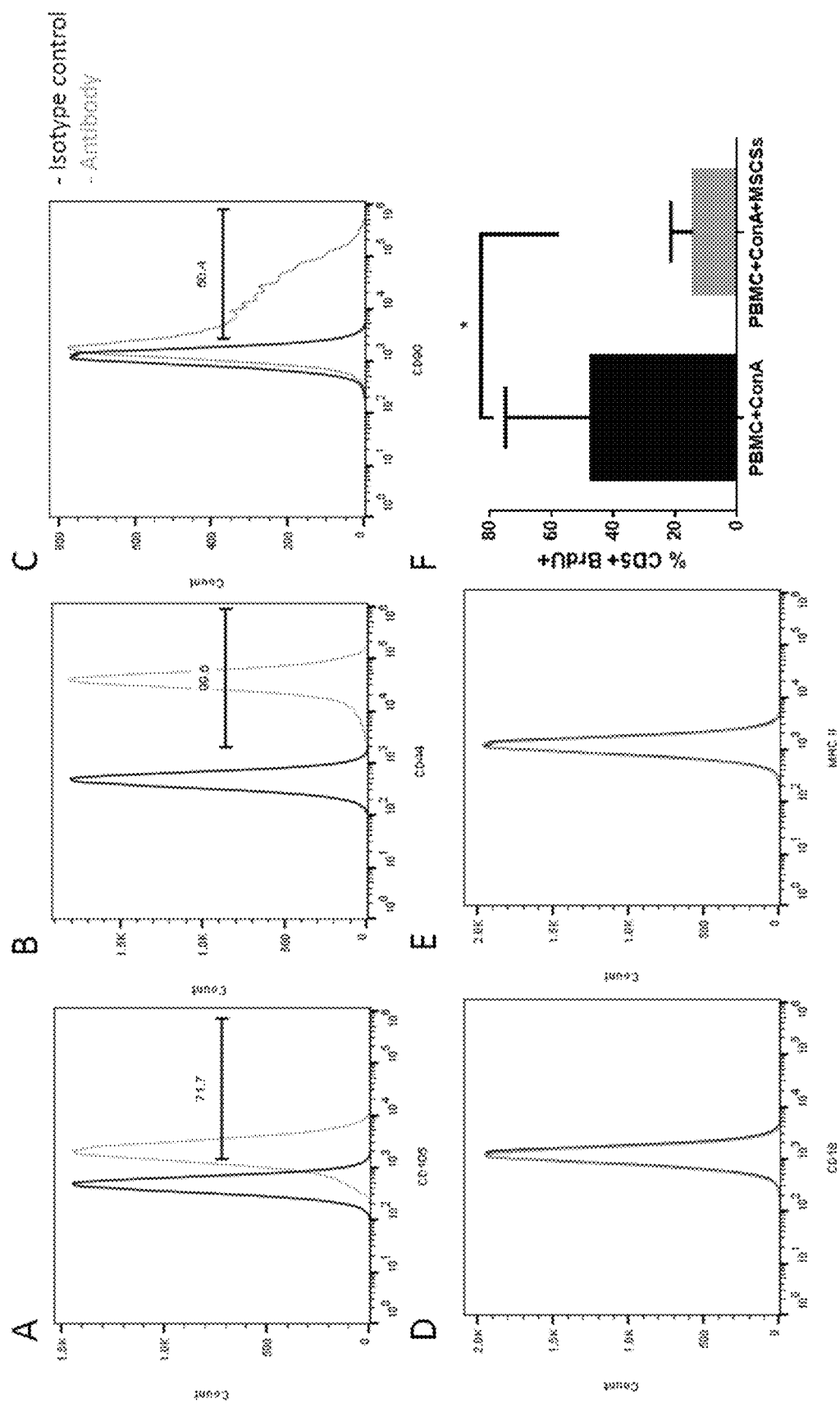
FIGS. 2A-E illustrates that feline ASCs are mesenchymal stem cells (MSCs). Feline ASCs expressed surface markers consistent with an MSC phenotype. They were CD105+ (A), CD44+ (B), CD90+ (C), CD18− (D), and MHC II− (E). They also suppressed proliferation of activated PBMCs in mixed leukocyte reactions (MLR) experiments (n=5, p=0.03) (F).

Study design. The study design is illustrated in FIG. 1. Cats that met the inclusion criteria had subcutaneous abdominal fat collected under general anesthesia. Peripheral blood was obtained prior to treatment and at 1, 3 and 6 months post treatment for a complete blood count, serum biochemistry profile, serum protein analyses, lymphocyte phenotyping, and cytokine analyses. In addition, presence of anti-bovine serum albumin (anti-FBS) antibodies was evaluated prior to and at 6 months post ASC administration. Oral biopsies were collected prior to ASC administration (n=9) and at 6 months post administration (n=3). Clinical disease severity was evaluated using a Stomatitis Disease Activity Index (SDAI) scoring system (34). The SDAI scoring was performed at the time of study enrollment and at the exit examination, (34). Briefly, the cat's owners completed a brief questionnaire and scored the appetite, activity level, grooming behavior and perceived oral comfort on a scale of 0 to 3. In addition, 2 veterinary dentists specialists (BA, FV), experienced in FCGS evaluation, scored the severity of oral inflammatory lesions as 0 (no lesion), 1 (mild), 2 (moderate) and 3 (severe). The SDAI score for each cat was calculated at each time point (range=0, no disease, to 20, severe disease). A final examination was performed at 6 months after the first ASC treatment. During the study period, the cats received only opioid analgesic management (i.e., buprenorphine or oxymorphone) without any immunosuppressive, antibiotic or non-steroidal anti-inflammatory medication. In order to evaluate the true therapeutic efficacy and safety of autologous ASCs administered systemically, we elected to administer only ASCs and no additional immunosuppressive or antibiotic therapy during the entire period of the study (i.e., 6 months). Our outcome measures (lymphocyte subsets, inflammatory parameters) could all potentially be altered by steroid therapy and would confound data analysis. In addition, as the mechanism(s) by which ASCs heal oral tissues and alter immune subsets is unknown, concurrent administration of immunosuppressive agents could alter ASC efficacy. In addition, blood from 6 cats that presented to the Dentistry and Oral Surgery service for mild dental disease was used to generate reference ranges for variables where robust reference intervals were not available (i.e. CD4 and CD8 numbers and serum IgA).

ASC isolation and expansion. ASC isolation and expansion was performed at the Regenerative Medicine Laboratory (RML) at the William T Pritchard Veterinary Medical Teaching Hospital according to previously established protocols (17). Briefly, ASCs were cultured in low-glucose Dulbecco's modified Eagle's medium (DMEM, Mediatech, Manassas, VA), 10% fetal bovine serum (FBS, HyClone Inc., Logan, Utah) and 1% penicillin/streptomycin (Thermo Fisher Scientific, Waltham, MA) in tissue culture flasks (Nunc, Roskilde, Denmark) and incubated at 37° C., 5% $CO_2$. Cells were passaged once they reached 70% confluency. Fresh, expanded, early passage cells were used for treatment (P2 or P3) and the remaining cells were cryopreserved. For the subsequent dose (at 4 weeks after the first dose), an aliquot of P1 cells were thawed and cultured expanded for 72 hrs to regain cell viability and function prior to infusion, effectively using P2 or P3. Cells are provided in glass vials to avoid plastic adherence while awaiting administration.

ASC phenotyping. Surface protein expression on fMSC lines was determined using flow cytometry as described previously (17). All antibodies were purchased from the Leukocyte Antigen Biology Laboratory, UCD, unless otherwise indicated. Antibodies included MHC II (42.3), CD18 (FE3.9F2), CD90 (CA1.4G8), CD44 (IM7; BioLegend), and CD105 (SN6; eBioscience). For unconjugated antibodies, a mouse IgG-phycoerythrin (PE) antibody (Jackson ImmunoResearch Labs) was used for secondary labeling. Canine CD8a (CA9.JD3), rat immunoglobulin G-allophycocyanin (IgG-APC) (eBR2a; eBioscience), and mouse IgG-APC (MCA928; AbD Serotec) were used as isotype controls. Samples were run on a flow cytometer (Cytomics FC500). Flow cytometry data were analyzed using FlowJo flow cytometry software (Tree Star, Inc.)

PBM proliferation assay. Peripheral blood mononuclear cell (PBMC) isolation and mixed leukocyte reactions (MLRs) were carried out as described (58) with modifications described below. Histopaque 1119 (Sigma-Aldrich) was mixed with Ficoll-Paque (GE Healthcare, Piscataway, NJ) and diluted with tissue culture water for a final specific gravity of 1.066. This diluted Ficoll-Paque was layered over the Histopaque. Whole blood was diluted with modified Tyrode's/HEPES buffer containing EDTA (12 mM $NaHCO_3$, 138 mM NaCl, 2.9 mM KCl, 10 mM HEPES, and 1M EDTA), and layered on top of the diluted Ficoll-Paque layer. The blood was centrifuged and PBMCs were collected and resuspended in activation medium (DMEM+10% FBS+1% P/S), and stored on ice until plating. PBMCs were activated with 5 mg/mL concanavalin A (Con-A; Sigma-Aldrich). To measure proliferation via BrdU, cells were collected and processed per manufacturer's instructions (BrdU Flow Kit; BD Biosciences), stained with a viability dye (Fixable Viability Dye eFlour®780; eBioscience, San Diego, CA), and anti-BrdU conjugated to Alexa Flour®647 (clone MoBU-1; Invitrogen), and analyzed on a flow cytometer (Cytomics FC500). Flow cytometry data were analyzed using FlowJo flow cytometry software (Tree Star, Inc.).

ASC treatment. Each cat received an ASC transfusion 10-14 days post fat harvest. All cats were admitted one day prior to treatment. Intravenous (IV) fluid administration (lactated Ringer solution) was initiated at least 30 min prior to treatment. A single dose (2 mg/kg) of diphenhydramine was administered subcutaneously 20 min prior to treatment. Each cat received 2 IV transfusions of $20 \times 10^6$ (about 5 million ASCs/kg) fresh autologous ASCs. Each dose of 20 million ASCs was administered slowly, over a period of 20-30 min. Each dose was drawn from the glass vial into the syringes in 4 separate aliquots (about 5 million cells at a time) just prior to administration to prevent ASC adherence to syringe plastic. All cats were hospitalized for 48-72 h after transfusion to monitor for adverse reactions. Opioid analgesics were administered during hospitalization every 8-12 h to be consistent with the cat's opioid analgesic management.

Histology and immunohistochemistry. Oral biopsies were fixed en bloc in 10% neutral buffered formalin. Transverse sections were embedded in paraffin and 5-μm sections were cut, mounted and stained with hematoxylin and eosin (H&E) according to standard laboratory protocols. Immunohistochemistry was performed on 4-μm thick, formalin-fixed, paraffin-embedded tissue sections, mounted on charged slides, and air-dried overnight. Sections were deparaffinized in xylene and rehydrated through graded alcohols to phosphate buffered saline (PBS). Endogenous peroxidases were quenched with 0.3% hydrogen peroxide for 30 min in methanol prior to rehydration. Antigen retrieval was performed in Dako Target Retrieval Solution (S1699) for 30 min at 95° C. and then cooled for 20 min. Sections were blocked for 20 min in 10% normal horse serum in Dulbecco's phosphate buffered saline (DPBS). Primary antibodies and dilutions were: rat anti CD3 (clone 3-12, diluted 1:10, Dr. Moore's Leukocyte Antigen Biology Lab, UC Davis School of Veterinary Medicine, Davis CA); and rabbit anti-CD20 (NeoMarker RB-9013-P1; 1:300; Thermo Fisher Scientific). Primary antibodies were incubated for 1 hr, rinsed, and detected with a Streptavidin-HRP label (anti-rabbit link, or anti-rat link; Biocare Medical's 4+ Detection System GR608, or GR607 and HP604, respectively). Each reagent was incubated for 10 minutes at room temperature, and 2, 3 min rinses occurred between each reagent application. Detection was visualized with Vector NovaRED for peroxidase (SK-4800), per manufacturer's instructions. Sections were counterstained in Mayer's hematoxylin. Non-specific background was evaluated with duplicate sections that received diluent in place of the primary antibody. Biopsies were interpreted by a board-certified veterinary pathologist (NV).

Hematology and protein analysis. Blood samples were collected into potassium EDTA vacutainers (Becton Dickinson, Franklin Lakes, NJ). White blood cells, lymphocytes and neutrophils were quantified by an automated analyzer (Bayer ADVIA 120, Bayer Diagnostics, Tarrytown, New York, USA). Serum was isolated from whole blood collected without an anticoagulant. After clotting, blood was centrifuged (1,000 g, 10 min) to isolate serum and aliquots were stored at −80° C. until analyzed. Serum biochemical profile was determined by an automated analyzer (Cobas c501, Roche Diagnostics International Ltd., Switzerland). Samples for serum IgA and IgG (radial immunodiffusion) and protein electrophoresis were shipped on dry ice overnight to the Cornell University Veterinary Diagnostic Laboratory, Ithaca, New York, USA.

Cytokine ELISAs. Interferon gamma (IFNγ), tumor necrosis factor alpha (TNFα), interleukin 1 beta (IL-1β), and interleukin 6 (IL-6) were measured in serum prior to and at 1, 3 and 6 months after the first ASC therapy using feline-specific ELISA kits (Duosets, R&D Systems, Minneapolis, MN). ELISA kits were run following the manufacturer's instructions except that samples were diluted at least ¼ in reagent diluent to dilute out serum effects. All ELISA samples were read on a Synergy HT Multi-Mode microplate reader with Gen5 software (Biotek, Winooski, VT).

Anti-Bovine Serum Albumin (BSA) ELISA. The anti-BSA ELISA was adapted from Gershwin et. al (35). Briefly 96-well ELISA plates (Thermo Fisher Scientific) were coated with 100 μL 1 μg bovine serum albumin (Fraction V, Fisher) in a carbonate-bicarbonate buffer (63.5 mM carbonate, pH 9.5), overnight at 4° C. The wells were then blocked by adding 100 μL, of 1% rabbit serum albumin (Sigma, St. Louis, MO) in DPBS (Life Technologies) to each well, followed by incubation at 37° C. for 1 hr. The wells were washed with DPBS+0.1% Tween20 (EMD Chemicals, San Diego, CA; "wash buffer") once for 10 minutes, followed by 6 brief washes. Feline serum samples were diluted 1:5,000 in wash buffer, and plated in triplicate (100 μL per well). Known negative and high positive feline samples were run as assay controls. Plates were incubated at 37° C. for 1 hr, then washed as above. 1004 of rabbit anti-feline IgG H&L-HRP (Southern Biotech, Birmingham, AL) diluted 1:10,000 was added to each well. The plates were incubated at 37° C. for 1 hr, then washed as above. 100 μL of freshly prepared TMB Peroxidase Substrate (KPL, Gaithersburg, MD) was added to each well and plates were incubated at room temperature in the dark until color developed. The colorimetric reaction was stopped with 100 μL of 2N $H_2SO_4$, and plates were read at 450-540 on a Synergy HT Multi-Mode microplate reader with GenS software (Biotek, Winooski, VT). The fold increase in color relative to the negative control sample was determined for each patient sample.

Flow cytometry. 100 μL aliquots of whole blood (EDTA) were labeled with 25 μL mouse anti feline CD4 (clone FE1.7B12), CD8α (clone FE1.10E9) or CD21 (clone CA2.1D6) (Leukocyte Antigen Biology Laboratory, UC Davis). Red blood cells were lysed with an ammonium chloride lysing buffer (154 mM ammonium chloride, 10 mM potassium bicarbonate, 100 μM EDTA, pH 7.2). Cells were pelleted and washed twice in flow buffer (DPBS with 1% equine serum (HyClone), 5 mM EDTA pH 7.2, and 0.01% sodium azide). Antibodies were detected using a PE-conjugated donkey anti-mouse IgG H+L F(ab')2, diluted 1/50 in flow buffer (Jackson Immunotech, West Grove, PA). Samples were read on a Beckman Coulter FC500 Flow Cytometer with Cytomics software (Hialeah, FL), and analyzed using FlowJo software (Treestar, Inc., Ashland, OR). Approximately 20,000 events were collected within a lymphocyte scatter gate, and cell fluorescence was analyzed for cells within this gate.

Statistical analyses. Data analysis was performed using GraphPad Prism version 6.05 software (GraphPad Software, San Diego, CA). Statistical significance between 2 groups was determined by two-tailed paired t tests (stomatitis index, biomarkers), and between timepoints by 2-way ANOVA (cytokine and T cell phenotype analyses). The number of cats in the non-responding group (n=2) prohibited accurate statistical analyses comparing responder cats to non-responders for most parameters. As such, basic descriptive statistics were used in these situations. P values of <0.05 were considered statistically significant.

Results

Feline ASCs have a typical MSC surface phenotype and inhibit lymphocyte proliferation in vitro. Feline ASCs were uniformly positive for CD105, CD44, and CD90, and negative for CD18, and MHCII (FIG. 2A-E). ASCs significantly suppressed T-cell proliferation when stimulated with ConA in co-culture with allogeneic PBMCs (FIG. 2F, n=5, p=0.03) as measured by BrdU incorporation.

Figure 3A:
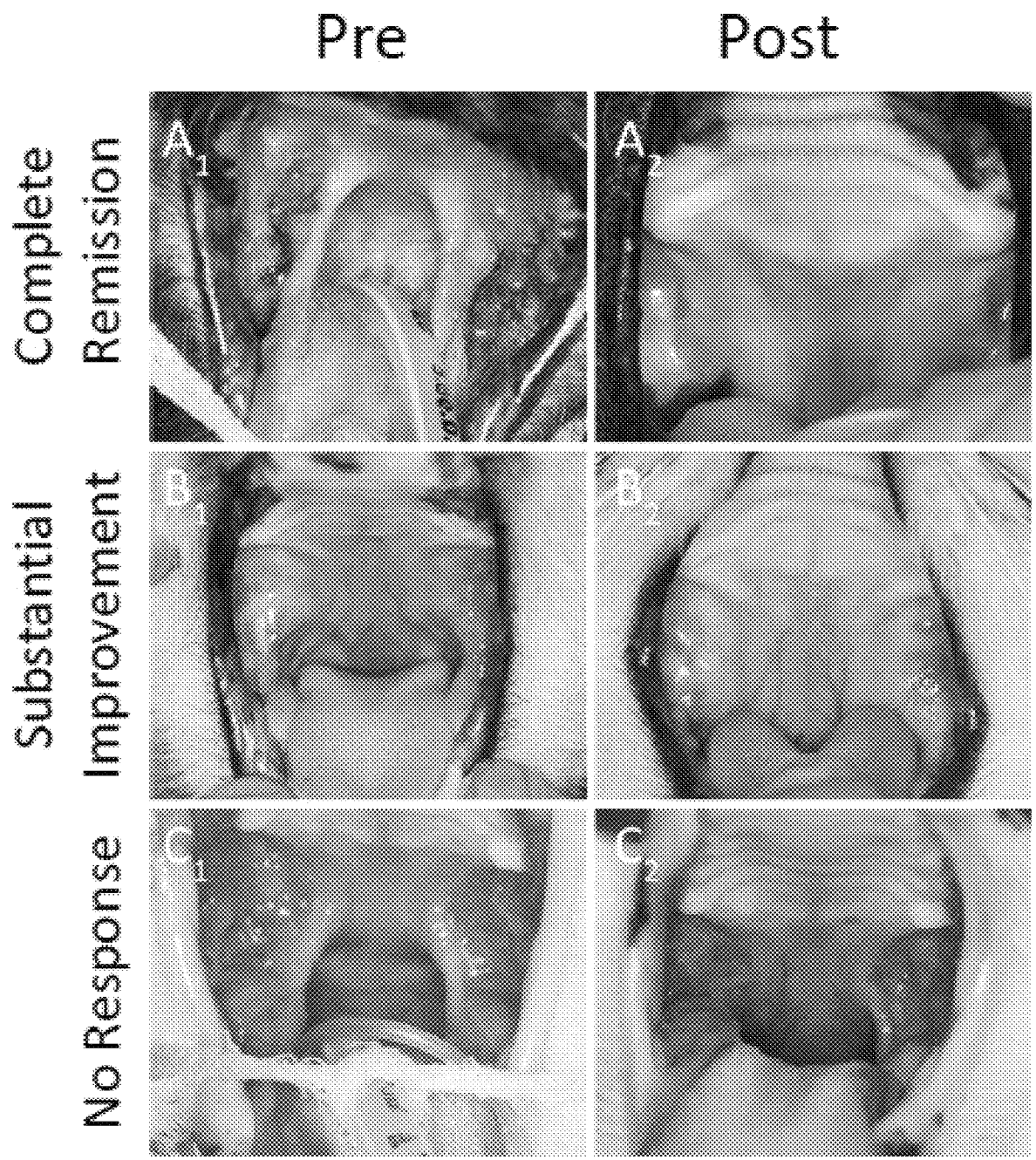
Figure 3C:
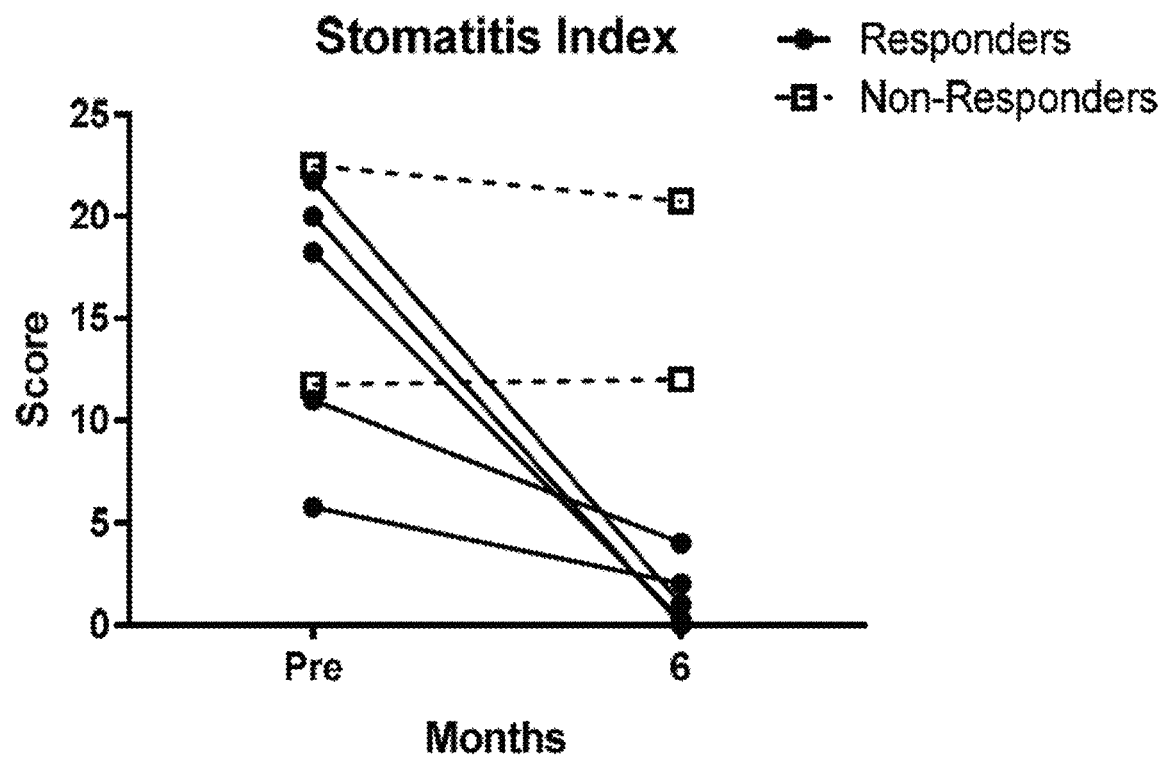

ASC treatment induced marked clinical improvement in cats with FCGS. Nine cats were enrolled in the study however 2 cats discontinued the clinical trial within the first 2 months of the study due to the owner's decision to administer corticosteroids to the cats. Seven cats completed the study and their signalment is presented in FIG. 1. All cats had full mouth tooth extractions and were considered non-responsive to any therapeutic intervention. All had chronic severe mucosal inflammation in the caudal oral cavity and various other locations within the oral cavity with a disease duration of 1-7 years (mean 2.7 years). During treatment, 2 cats experienced immediate transfusion reactions characterized by rapid respiration, urination, vomiting and apathy. These reactions were infusion rate-dependent and spontaneously resolved within 10-15 min after which the transfusion was completed at a slower rate (2 million cells/minute). No other short or long term adverse reactions were noted in any of the cats. Of the 7 cats, 5 cats responded to treatment and exhibited either complete clinical remission (n=3) or substantial clinical improvement (n=2) within 1-4 months of the first ASC administration (FIG. 3A1, A2, B1 and B2). Two cats had either minimal or no clinical response (FIG. 3C1, C2).

Clinical assessment of disease severity, by means of the SDAI, confirmed our clinical observations (FIG. 3D, E). In general, the improvement of clinical signs corresponded with improvement of the oral mucosal lesions. The responder cats began eating more, gaining weight, resuming grooming behavior and resuming sociability. The owners reported a return to pre-FCGS activity levels in 4 responder cats and near return to pre-FCGS activity in one responder cat. The 2 cats that did not respond had static SDAI and the owners reported the same activity levels as with historic immunosuppressive therapy. There was no significant difference between responder and non-responder stomatitis index before treatment, indicating that clinical severity does not predict response (FIG. 3D, E).

Figure 4:
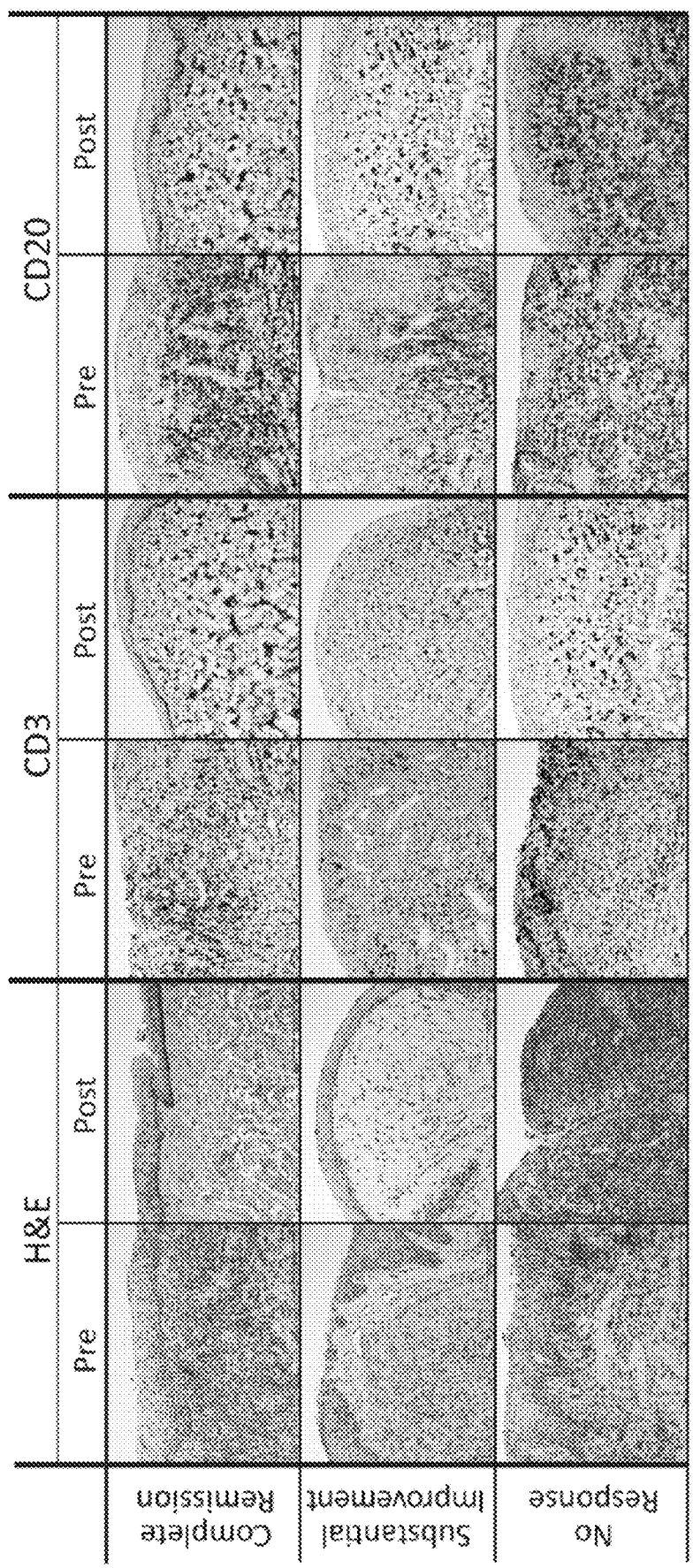
FIG. 4 illustrates histological and immunohistochemical evaluation of the FCGS oral mucosa. Histomorphology of sections from all patients pretreatment was consistent with severe lymphoplasmacytic and neutrophilic stomatitis accompanied with epithelial hypertrophy and multifocal ulcerations (complete remission (A), substantial improvement (B), no response (C) in H&E column). Pretreatment CD3+ T cell were present within the epithelium and submucosa and CD20+ B cells were mainly present within the subepithelial stroma. Sections obtain from a cat with complete clinical remission (A 'Post') had histology consistent with normal mucosa. Histomorphology of sections from a substantial responder (B 'Post') was consistent with mild lymphoplasmacytic stomatitis accompanied by mild epithelial hyperplasia and superficial stromal edema. After treatment, moderate numbers of CD3+ T cells were observed within the epithelium and stroma in sections form partial responders and moderate numbers of CD20+ T cells were located in the subepithelial stroma. Histomorphology of sections obtained from non-responder cat after treatment (C 'Post') was consistent with severe chronic lymphoplasmacytic and neutrophilic ulcerative stomatitis which was histologically to the sections prior to treatment. Distribution of CD3+ and CD20+ cells was similar to that observed before treatment. Scale bar=200 μm.

Clinical and histopathological correlation between responders and non-responder cats. Oral mucosal biopsies were obtained from all cats prior to study enrollment. Post ASC treatment oral biopsies were available from one cat that achieved complete clinical remission, one cat that exhibited substantial improvement and one cat that did not respond to treatment. All biopsies were analyzed histologically and post treatment biopsies were compared to the corresponding pre-treatment biopsy. All cats that showed improvement in SADI clinical scores also exhibited improved tissue inflammation on histopathological examination (FIG. 4).

In all pretreatment biopsies the epithelium and subepithelial stroma were heavily infiltrated by lymphocytes, plasma cells, and neutrophils, with occasional. Mott cells, mast cells and histiocytes. The surface epithelium was multifocally ulcerated and hyperplastic with multiple rete pegs extending deep into the subjacent stroma. Immunohistochemistry reveled that CD3+ cells were present within the epithelium and subepithelial stroma, while CD20+ were restricted to the subepithleial stroma (FIG. 4).

Upon completion of the study, a complete return to normal tissue architecture was observed in a cat with complete clinical remission. Rare lymphocytes were observed within subepithelial stroma with no evidence of epithelial hyperplasia, ulceration or inflammation. The absence of CD3 and CD20 lymphocytes was confirmed by immuno-histochemistry (FIG. 4, top full panel).

There was mild lymphoplasmacytic infiltration in the oral mucosal sections from cat with substantial clinical improvement. There was no evidence of neutrophilic inflammation or ulceration. Occasional rete pegs were present and superficial stroma was moderately expanded by edema. Moderate numbers of CD3+ T cells were scattered randomly within the epithelium and the stroma while moderate numbers of CD20+ B cells were primarily located in the subepithelial stroma (FIG. 4, middle full panel).

Histologic sections of oral mucosa from a nonresponsive cat post treatment was consistent with severe, chronic, lymphoplasmacytic and neutrophilic ulcerative stomatitis which was identical to the findings prior to treatment. There were moderate numbers of randomly scattered CD3+ T cells intraepithelially and within the subepithelial stroma. The subepithelial stroma was densely and diffusely infiltrated by CD20+ B cells (FIG. 4, bottom full panel).

ASC administration modulates immune cell subsets: cats with FCGS have high circulating CD8+ T cells that normalize with therapy. Cats with FCGS typically have systemic evidence of inflammation including blood neutrophilia, polyclonal hypergammaglobulinemia and increased expression of pro-inflammatory serum cytokines (9, 36). The cats in this study recapitulated this phenotype. Neutrophil counts were generally elevated above the reference interval in responding cats (responders pre injection: $10.7 \times 10^3 +/- 4.8 \times 10^3$, reference range: $2.0 \times 10^3 - 9.0 \times 10^3$) and returned to normal or near-normal levels within 6 months post first injection (FIG. 5A; responders 6 months: $6.3 \times 10^3 +/- 3.0 \times 10^3$), while non-responding cats showed no change in neutrophil number and remained in or near the reference interval throughout the study (non-responders pre injection: $6.4 \times 10^3 +/- 2.0 \times 10^3$, non-responders 6 months: $9.5 \times 10^3 +/- 2.4 \times 10^3$; FIG. 5A). Non-responding cats had higher total serum globulin levels and lower serum IgA levels than responding cats, however neither group showed a change after ASC therapy (FIG. 5B, C).

Most cats had normal percentages of circulating CD4+ T cells (with 2 cats having decreased percentages) and this did not change over 6 months regardless of clinical response (FIG. 5D). In contrast, in 3 out of 5 cats who responded to ASC therapy, baseline circulating CD8+ T cells levels were elevated above the reference range (FIG. 5E) resulting in a low CD4/CD8 ratio in 4/5 responder cats at time 0 (FIG. 5F). CD8+ T cells remained high one month after the first injection (responders pre injection: 29%+/−18.57%, non-FCGS controls: 16%+/−4.18%). However by 6 months post ASC treatment, the percentage of CD8 T cells had nearly normalized in all responder cats with a resultant normalization of the blood CD4/CD8 ratio by 6 months in 4/5 responder cats (FIGS. 5E and 5F). One of the non-responding cats showed a consistently low percentage of CD8 T cells and high CD4/CD8 ratio throughout. Interestingly, this cat had a very high B cell count in peripheral blood. The other non-responder showed higher than normal CD8 percentage and low CD4/CD8 ratio which did not change throughout the study (FIGS. 5E and 5F).

Decreased percentage of CD8lo cells in blood of cats with FCGS predict an increased likelihood of response to MSC infusion. Circulating CD8+ T cells were further interrogated to identify a population of CD8+hi and a population of CD8+lo cells (FIGS. 6A and 6B). A majority (>80%) of these CD8lo cells were CD5+ confirming that they were CD8lo T cells. Cats that responded to ASC therapy had a significantly lower percentage of CD8lo cells (as a percentage of total CD8+ T cells) than normal cats and cats that did not respond to therapy (FIG. 6A-C). By 6 months after the first injection, the CD8lo population increased significantly, such that 3 of the 5 responder cats were within the control range and were no longer significantly different from the non-responders (FIG. 6D). The level of <15% CD8lo cells in the blood of FCGS cats was 100% predictive of response to ASC therapy in this small cohort of cats.

Cats with FCGS that respond to ASC transfusion show increased serum IL6. The proinflammatory serum cytokines TNFα, IL-1β and IFN-γ were generally elevated in all cats prior to ASC transfusion (FIG. 7). One of the non-responding cats exhibited a marked proinflammatory cytokine profile, indicative of a severe systemic inflammatory state, throughout the study with only IFN-γ normalizing (FIG. 7). Although an outlier, we elected to include this cat given the small number of patients in this study. The other non-responding cat showed very low levels of all cytokines (FIG. 7). Both IFN-γ and IL-1β decreased in most cats after the first. ASC injection and stayed low or undetectable with variable, small increases in IFN-γ (n=2) and IL-1β (n=1) at later time points (FIGS. 7A and 7B). TNFα was more variable with three responder cats showing decreased TNFα while two maintained high serum concentrations (FIG. 7C). Interestingly, two cats that achieved complete clinical cure maintained high serum TNFα throughout the study. Interestingly, serum IL-6 was unmeasurable at baseline in all but the one proinflammatory, non-responding outlier cat. Response to therapy was associated with an increase in serum IL-6 in all responder cats by 3 months that plateaued through the 6 month time point (FIG. 7D).

BSA antibody levels. Feline ASCs were cultured in FBS, and, as such, we wanted to determine 1) if cats developed antibodies to BSA, the primary protein in FBS, and 2) if the development of antibodies was associated with treatment failure. All cats had varying amounts of BSA antibody prior to ASC administration however titers did not change after cell administration (stayed high or stayed low) and did not correlate with the response (or absence of a response) to ASC therapy (Table 1).

TABLE 1

Table 1: Patient Signalment and Clinical Information

| | Signalment | | | | Clinical | Data | | FBS Antibody (fold | |
|---|---|---|---|---|---|---|---|---|---|
| | | | | | Length of | Follow | | | |
| Cat | Age | | | | disease | up | Adverse | increase over neg) | |
| ID | (Year) | Breed | Sex | Weight | (year) | Response | (months) | Effects | Pre | Post |
| 1 | 11 | DSH | F | 3.8 | 4.5 | Cure in 4 months | 24 | Short episodes of vomiting | 6.31 | 1.38 |
| 2 | 14.5 | DSH | M | 3.5 | 1.4 | Cure in 3 months | 8* | None | 0.69 | 0.59 |
| 3 | 3 | DSH | M | 5.1 | 1 | Clinical improvement | 11 | None | 0.68 | 1.67 |
| 4 | 10 | DSH | F | 4.8 | 1 | No response | 6* | None | 11.27 | 10.22 |
| 5 | 10 | Siamese | M | 5.1 | 7 | Clinical improvement | 11 | None | 9.26 | 11.87 |
| 6 | 4 | DSH | M | 4.6 | 2.5 | Cure in 2 months | 8 | None | 2.08 | 1.74 |
| 7 | 11 | DLH | M | 4.9 | 1.5 | No response | 13 | N/A | 8.16 | 5.54 |
| 8 | 11.5 | DSH | F | 7.2 | 2 | No response | 8 | Rapid respiration, urination, apathy | 2.12 | N/A |

*Indicates animals are deceased due to unrelated causes

Discussion

This is the first study to investigate the use of ASCs for treatment of severe oral mucosal inflammatory disease in a naturally occurring animal model. We found that systemically administered fresh, autologous ASCs can achieve cure or substantial reduction in inflammatory lesions associated with FCGS resulting in regeneration of the oral mucosa and improved clinical signs. Although this safety and efficacy study did not explicitly include a no-treatment control group, spontaneous recovery or even significant clinical improvement has never been reported in cats with refractory FCGS. Cats that responded to therapy had a skewed peripheral blood CD4/CD8 ratio due to increased circulating CD8+ cells with a decreased percentage of CD8lo cells being highly predictive of response to MSC therapy. Full clinical response to therapy was delayed, generally took 2-4 months post the first ASC transfusion, and followed an increase in serum IL-6 concentration (and, for those cats with complete cure, a concurrent increase in serum TNFα) with a resultant normalization of the CD4/CD8 ratio, a reduction in blood neutrophil number and a general reduction of the pro-inflammatory serum cytokines, IFNγ and IL-1β. Transfusion reactions were rare and were transfusion rate-dependent. Cats had varying amounts of anti-BSA antibody prior to ASC administration which did not change after cell administration and which did not correlate to the presence of absence of response to therapy.

In this study we demonstrated that the IV infusion of a relatively high dose (20 million cells/cat, equivalent to about 5 million cells/kg) of autologous ASCs is safe and well tolerated in cats with severe oral inflammatory disease. During cell administration, we observed rare transfusion reactions that were rate-of-cell administration dependent. A safe infusion rate was determined (2 million cells/min) that eliminated these reactions. Cats that had transfusion reactions recovered rapidly and were no less likely to respond to ASC treatment than those cats that did not exhibit transfusion reactions. The reactions were independent of anti-BSA antibody titers. Our findings suggest that previous FBS exposure via vaccination does not predispose animals to react to autologous IV stem cell injections with cells grown in FBS-containing media. Transfusion reactions have been previously reported in a study where cats received low doses of ASCs. However there were differences in our studies that might explain the relatively minor transfusion reactions that we noted that were easy to eliminate by slowing the transfusion. For example, cats in the other study received a substantially lower dose of cells, however, the cells were allogeneic, had been frozen in DMSO/FBS and were not culture expanded after cryopreservation prior to administration (22).

One objective of this study was to determine if a biomarker could be found that could both predict response to ASC therapy and help narrow down possible mechanism(s) by which ASCs work to heal oral inflammation that is secondary to chronic antigenic stimulation and characterized by T cell activation in tissues. We found that circulating CD8+ T cells were elevated in most FCGS cats prior to ASC treatment (and hence these cats had a skewed CD4/CD8 ratio), and, of these CD8+ cells, very few were CD8lo. In fact a decreased CD8lo percentage within the CD8+ blood cells was 100% predictive of response to ASC therapy.

CD8lo cells have been characterized in humans, mice and cats. These cells are associated with chronic viral infections such as Epstein-Barr virus (37) and HIV in humans, and FIV in cats (38-40), as well as chronic antigen stimulation in a mouse skin graft model. In cats, CD8lo cells express CD44, CD49d, and CD18 as well as high MHCII and low or absent CD62L, consistent with an activated phenotype (38-40). They have strong anti-FIV suppressor activity (38), and can be used as a biomarker to differentiate cats with FIV infection from FIV-vaccinated cats (41). Receptor expression on CD8 cells may dictate whether a CD8 cell has a suppressive or cytotoxic phenotype. Decreased receptor expression of CD8 limits the ability of cells to be classically activated to a cytotoxic phenotype and increases suppressive functions. These CD8lo cells likely represent a subset of activated CD8 effector/suppressor cells capable of down-regulating the activation of naïve T cells, and resulting from repeated and/or continuous exposure to self-antigen. The decreased percentage of CD8lo cells in FCGS cats that responded to ASC therapy may imply that these cats have decreased suppressor function and that ASC administration supports the expansion of CD8lo cells helping to resolve the inflammatory oral response. In non-responders, these cells are not lacking before treatment and thus ASCs do not induce a response via this mechanism.

ASC administration resulted in complete clinical remission or substantial clinical improvement in 5 out of 7 FCGS cats that completed the study. This clinical improvement was associated with histological clearing of both CD3+ T cells and CD20+ B cells from the lesions of responder cats. If we had screened for CD8 predominance in blood and a concurrent decrease in CD8lo cells, we could have predicted with 100% accuracy the response to therapy in this small cohort of cats. The elevation of CD8+ T cells found in circulation support the theory that FCGS is an inappropriate response to chronic oral antigenic stimulation from clinical/subclinical viral infections (11-14). In the case of FCGS, it is likely that CD8+ T cells are contributing to the inflammatory lesions, and we observe correlation between the reduction of CD8+ T cells in circulation and the reduction in clinical signs and histological markers of inflammation. A predominance of CD8+ T cells has been reported previously, suggestive of an underlying cytotoxic cell-mediated immune response (9). We did not collect frozen tissue samples in this cohort of cats, and therefore we were unable to discriminate between CD4+ and CD8+ tissue cells in this study.

Our data are consistent with the conclusion that ASC administration to cats with FCGS has immunomodulatory effects. Aside from the reduction in CD8+ T cells, responding cats show a reduction in the systemic inflammatory response following ASC treatment including a reduction of circulating neutrophils, and reduced serum levels of IFN-γ and IL-1β. The cats that responded with complete clinical remission showed a sustained increase in serum TNFα and all responder cats showed elevation in serum IL-6 concentration. IL-6 is a pleiotropic cytokine involved in pro- and anti-inflammatory processes (42). In humans, IL-6 induces IL-21 production under Th1 priming conditions which promotes Th17 differentiation (43-45). However, IL-21 also promotes IL-10 secretion and inhibits IFNγ production in the developing Th17 cells, preventing the generation of pathogenic Th1/Th17 effector cells. IL-21 also inhibits the differentiation of CD8+ T cells. This inhibition of excessive CD8+ T cell differentiation, leading to functional T cell exhaustion, may be important for the protective role of IL-21 in chronic viral infections (46-50).

IL-6 is a major regulator of the balance between regulatory T cells (Tregs) and effector Th17 cells (51). Th17 cells are a key player in the pathogenesis of autoimmune diseases while Tregs maintain tolerance and restrain excessive effector T cell responses (51). IL-6 together with TGFβ, induce Th17 cells while IL-6 inhibits TGFβ-induced Treg differentiation (52-56). However, this effect of IL-6 seems to be restricted to the development of naïve CD4 T cells, while transgenic mice in which serum IL-6 levels are constitutively elevated actually have more Foxp3+ natural Tregs than non-transgenic mice, and those Tregs normally suppress proliferation of naïve T cells in vitro (57). Hence, in the context of chronic immune activation, this function of IL-6 is likely more relevant. ASCs constitutively express TGFβ, while IL-6 is expressed upon activation with PHA (58). IL-6 is secreted by ASCs from all species tested to date including horses, dogs and cats (58, 59). Ongoing work in our lab is focused on both in vitro and in vivo exploration of Th17 and Treg cells in cats.

Clinical trials using MSC products have often favored frozen aliquots of allogeneic cells for trials focused on chronic inflammatory lesions or acute ischemic lesions due to the relative ease of FDA approval for "lots" of frozen cells and the advantage of an "off-the-shelf" product that can be administered without the lag time associated with cell expansion. Recently, however, it has been shown that 2-3 days of culture and stem cell expansion for patients receiving allogeneic stem cell transfusions may increase cell viability and cell activation readiness (60). In addition, the use of DMSO as a cryoprotectant may account for the higher incidence of transfusion reactions seen with frozen cells and potentially interfere with therapeutic outcomes (60, 61). Our group favors fresh cells to frozen cells for therapeutic administration and we believe much of our efficacy data, in FCGS cats, and other ongoing clinical trials, are related to the infusion of freshly expanded cells.

There remains controversy and a paucity of data, in any given species, to support the use of autologous versus allogenic stem cells in terms of efficacy and outcome (60, 61). There is some evidence that the IV administration of human MSCs may induce an inflammatory cell response (62-64) and it has been shown in horses that completely unmatched allogeneic cell infusion can result in anti-MSC antibody production although the significance of antibody development is not known (25). Although the convenience and practicality of using allogeneic cell sources for treatment in the clinical setting is attractive, we elected to use autologous cells as our first line of therapy to maximize the potential for efficacy while minimizing interference from an immune response. In our hands, the autologous cells were safe and efficacious for this particular disease process and, given that the disease is chronic, the time needed for cell expansion does not hinder patient health. Additional investigation using fresh, allogeneic cells to treat this disease is ongoing. It appears that the use of allogeneic cells may be permissible in some animal species, even when administered systemically, while the use of allogeneic cells may be less feasible in other species. As with the issue of fresh versus frozen stem cells, there is a lack of long term, randomized, placebo-controlled studies to make definitive statements. However, as FCGS is a common disease with limited therapeutic options, approaching these questions in a naturally occurring model of disease becomes practical.

Response to ASC therapy was often delayed by up to 4 months after the first injection even in cats who fully responded. This delayed response may be due to ASCs acting through a systemic mechanism that prevents activation of new T cells, or slowly provides regulatory signals to activated cells, which would then reveal clinical response only as activated pathogenic cells apoptose or reach an exhausted state. This delayed response is important for clinicians to note, to avoid a premature conclusion that therapy was ineffective.

CONCLUSION/SUMMARY

In summary, the IV injection of ASCs in cats diagnosed with FCGS that have not responded to conventional therapy is safe and >70% effective. Cell therapy was most effective in cats with decreased percentages of blood CD8lo cells. Successful ASC therapy resulted in: (1) complete clinical remission or reduction in clinical disease severity, (2) histological resolution of the oral lesions, (3) reduction of total circulating CD8+ T cells (and increased CD8lo cells) (4) resolution of neutrophilia and reduction of serum proinflammatory cytokine concentrations (IL-1β and IFNγ) and (5) increases in serum IL-6. While the full mechanisms by which ASC treatment reduces inflammation in this model remain to be elucidated, this study demonstrates the clinical potential of ASC therapy for oral inflammatory lesions characterized by CD8+ cells and T cell activation. We also identified a potentially useful biomarker that could both dictate patient enrollment (decreased percentage of CD8lo cells) as well as shed light on the mechanisms by which ASCs modulate healing in these inflammatory lesions. These results are encouraging both for the treatment of a refractory, severe lesion in cats, but also as a potentially translatable therapy for the treatment of human oral inflammatory disease.

REFERENCES FOR EXAMPLE 1 AND BACKGROUND

1. Alpsoy E, Akman-Karakas A, Uzun S. Geographic variations in epidemiology of two autoimmune bullous diseases: pemphigus and bullous pemphigoid. ARCH. DERMATOL. RES. 2015.

2. Joly P, Litrowski N. Pemphigus group (vulgaris, vegetans, foliaceus, herpetiformis, brasiliensis). CLIN. DERMATOL. 2011; 29(4).432-436.

3. di S D, Guida A, Salerno C et al. Oral lichen planus: a narrative review. FRONT BIOSCI. (ELITE. ED.) 2014; 6:370-376.

4. Omar A A, Hietanen J, Kero M et al. Oral lichen planus and chronic junctional stomatitis: differences in lymphocyte subpopulations. ACTA ODONTOL. SCAND. 2009; 67(6): 366-369.

5. Lavanya N, Jayanthi P, Rao U K et al. Oral lichen planus: An update on pathogenesis and treatment. J. ORAL. MAXILLOFAC. PATHOL. 2011; 15(2):127-132.

6. Girard N, Servet E, Biourge V et al. Periodontal health status in a colony of 109 cats. J. VET. DENT. 2009; 26(3):147-155.

7. Jennings M W, Lewis J R, Soltero-Rivera M M et al. Effect of tooth extraction on stomatitis in cats: 95 cases (2000-2013). J. AM. VET. MED. ASSOC 2015; 246(6):654-660.

8. Arzi B, Murphy B, Cox D P et al. Presence and quantification of mast cells in the gingiva of cats with tooth resorption, periodontitis and chronic stomatitis. ARCH. ORAL BIOL. 2010; 55(2):148-154.

9. Harley R, Gruffydd-Jones T J, Day M J. Immunohistochemical characterization of oral mucosal lesions in cats with chronic gingivostomatitis. J. COMP PATHOL 2011; 144(4):239-250.

10. Healey K A, Dawson S, Burrow R et al. Prevalence of feline chronic gingivo-stomatitis in first opinion veterinary practice. J. FELINE. MED. SURG. 2007; 9(5):373-381.

11. Pedersen N C. Inflammatory oral cavity diseases of the cat. VET. CLIN. NORTH AM. SMALL ANIM PRACT. 1992; 22(6):1323-1345.

12. Dowers K L, Hawley J R, Brewer M M et al. Association of Bartonella species, feline calicivirus, and feline herpesvirus 1 infection with gingivostomatitis in cats. J. FELINE. MED. SURG. 2010; 12(4):314-321.

13. Hennet P R, Camy G A, McGahie D M et al. Comparative efficacy of a recombinant feline interferon omega in refractory cases of calicivirus-positive cats with caudal stomatitis: a randomised, multi-centre, controlled, double-blind study in 39 cats. J. FELINE. MED. SURG. 2011; 13(8):577-587.

14. Lommer M J, Verstraete F J. Concurrent oral shedding of feline calicivirus and feline herpesvirus 1 in cats with chronic gingivostomatitis. ORAL MICROBIOL. IMMUNOL. 2003; 18(2):131-134.

15. Bodesson D L, Peroni J F. The regenerative medicine laboratory: facilitating stem cell therapy for equine disease. CLIN. LAB MED. 2011; 31(1):109-123.

16. Dominici M, Le B K, Mueller I et al. Minimal criteria for defining multipotent mesenchymal stromal cells. The International Society for Cellular Therapy position statement. CYTOTHERAPY. 2006; 8(4):315-317.

17. Arzi B, Kol A, Murphy B et al. Feline Foamy Virus Adversely Affects Feline Mesenchymal Stem Cell Culture and Expansion: Implications for Animal Model Development. STEM. CELLS. DEV. 2014.

18. Beggs K J, Lyubimov A, Borneman J N et al. Immunologic consequences of multiple, high-dose administration of allogeneic mesenchymal stem cells to baboons. CELL TRANSPLANT. 2006; 15(8-9):711-721.

19. Carrade D D, Borjesson. D L. Immunomodulation by mesenchymal stem cells in veterinary species. COMP MED. 2013; 63(3):207-217.

20. Martinello T, Bronzini I, Maccatrozzo L et al. Canine adipose-derived-mesenchymal stem cells do not lose stem features after a long-term cryopreservation. RES. VET. SCI. 2011; 91(1):18-24.

21. Quimby J M, Webb T L, Gibbons D S et al. Evaluation of intrarenal mesenchymal stem cell injection for treatment of chronic kidney disease in cats: a pilot study. J. FELINE. MED. SURG. 2011; 13(6):418-426.

22. Quimby J M, Webb T L, Habenicht L M et al. Safety and efficacy of intravenous infusion of allogeneic cryopreserved mesenchymal stem cells for treatment of chronic kidney disease in cats: results of three sequential pilot studies. STEM CELL RES. THER. 2013; 4(2):48.

23. Vieira N M, Brandalise V, Zucconi E et al. Isolation, characterization, and differentiation potential of canine adipose-derived stem cells. CELL TRANSPLANT. 2010; 19(3):279-289.

24. Kang M H, Park H M. Evaluation of adverse reactions in dogs following intravenous mesenchymal stem cell transplantation. ACTA VET. SCAND. 2014; 56:16.

25. Kol A, Wood J A, Carrade Holt D D et al. Multiple intravenous injections of allogeneic equine mesenchymal stem cells do not induce a systemic inflammatory response but do alter lymphocyte subsets in healthy horses. STEM. CELL RES. THER. 2015; 6(1):73.

26. Ben-Ami E, Berrih-Aknin S, Miller A. Mesenchymal stem cells as an immunomodulatory therapeutic strategy for autoimmune diseases. AUTOIMMUN. REV. 2011; 10(7):410-415.

27. Corcione A, Benvenuto F, Ferretti E et al. Human mesenchymal stem cells modulate B-cell functions. BLOOD 2006; 107(1):367-372.

28. Le B K, Pittenger M. Mesenchymal stem cells: progress toward promise. CYTOTHERAPY. 2005; 7(0:36-45.

29. Peroni J F, Borjesson D L. Anti-inflammatory and immunomodulatory activities of stem cells. VET. CLIN. NORTH AM. EQUINE PRACT. 2011; 27(2):351-362.

30. Singer N G, Caplan A I. Mesenchymal stem cells: mechanisms of inflammation. ANNU. REV. PATHOL. 2011; 6:457-478.

31. Forbes G M, Sturm M J, Leong R W et al. A phase 2 study of allogeneic mesenchymal stromal cells for luminal Crohn's disease refractory to biologic therapy. CLIN. GASTROENTEROL. HEPATOL. 2014; 12(1):64-71.

32. Prasad V K, Lucas K G, Kleiner G I et al. Efficacy and safety of ex vivo cultured adult human mesenchymal stem cells (Prochymal) in pediatric patients with severe refractory acute graft-versus-host disease in a compassionate use study. BIOL. BLOOD MARROW TRANSPLANT. 2011; 17(4):534-541.

33. Zhang L S, Liu Q F, Huang K et al. [Mesenchymal stem cells for treatment of steroid-resistant chronic graft-versus-host disease]. ZHONGHUA NEI KE. ZA ZHI. 2009; 48(7):542-546.

34. Lommer M J. Efficacy of cyclosporine for chronic, refractory stomatitis in cats: A randomized, placebo-controlled, double-blinded clinical study. J. VET. DENT. 2013; 30(1):8-17.

35. Gershwin L J, Netherwood K A, Norris M S et al. Equine IgE responses to non-viral vaccine components. VACCINE. 2012; 30(52):7615-7620.

36. Harley R, Helps C R, Harbour D A et al. Cytokine mRNA expression in lesions in cats with chronic gingivostomatitis. CLIN. DIAGN. LAB IMMUNOL. 1999; 6(4): 471-478.

37. Trautmann A, Ruckert B, Schmid-Grendelmeier P et al. Human CD8 T cells of the peripheral blood contain a low CD8 expressing cytotoxic/effector subpopulation. IMMUNOLOGY 2003; 108(3):305-312.

38. Gebhard D H, Dow J L, Childers T A et al. Progressive expansion of an L-selectin-negative CD8 cell with anti-feline immunodeficiency virus (FIV) suppressor function in the circulation of FIV-infected cats. J. INFECT. DIS. 1999; 180(5):1503-1513.

39. Lehmann R, von B B, Niederer E et al. Immunization-induced decrease of the CD4+:CD8+ ratio in cats experimentally infected with feline immunodeficiency virus. VET. IMMUNOL. IMMUNOPATHOL. 1992; 35(1-2): 199-214.

40. Willett B J, Hosie M J, Callanan J J et al. Infection with feline immunodeficiency virus is followed by the rapid expansion of a CD8+ lymphocyte subset. IMMUNOLOGY 1993; 78(1):1-6.

41. Litster A, Lin J M, Nichols J et al. Diagnostic utility of CD4%:CD8 low % T-lymphocyte ratio to differentiate feline immunodeficiency virus (FIV)-infected from FIV-vaccinated cats. VET. MICROBIOL. 2014; 170(3-4):197-205.

42. Hoogduijn M J, Roemeling-van R M, Engela A U et al. Mesenchymal stem cells induce an inflammatory response after intravenous infusion. STEM. CELLS. DEV. 2013; 22(21):2825-2835.

43. Caprioli F, Sarra M, Caruso R et al. Autocrine regulation of IL-21 production in human T lymphocytes. J. IMMUNOL. 2008; 180(3):1800-1807.

44. Nurieva R, Yang X O, Martinez G et al. Essential autocrine regulation by IL-21 in the generation of inflammatory T cells. NATURE. 2007; 448(7152):480-483.

45. Zhou L, Ivanov I I, Spolski R et al. IL-6 programs T(H)-17 cell differentiation by promoting sequential engagement of the IL-21 and IL-23 pathways. NAT. IMMUNOL. 2007; 8(9):967-974.

46. Elsaesser H, Sauer K, Brooks D G. IL-21 is required to control chronic viral infection. SCIENCE. 2009; 324 (5934): 1569-1572.

47. Frohlich A, Kisielow J, Schmitz I et al. IL-21R on T cells is critical for sustained functionality and control of chronic viral infection. SCIENCE. 2009; 324(5934):1576-1580.

48. Hinrichs C S, Spolski R, Paulos C M et al. IL-2 and IL-21 confer opposing differentiation programs to CD8+ T cells for adoptive immunotherapy. BLOOD, 2008; 111(10: 5326-5333.

49. Kastirr I, Maglie S, Paroni M et al. IL-21 is a central memory T cell-associated cytokine that inhibits the generation of pathogenic Th1/17 effector cells. J. IMMUNOL. 2014; 193(7):3322-3331.

50. McPhee C G, Bubier J A, Sproule T J et al. IL-21 is a double-edged sword in the systemic lupus erythematosus-like disease of BXSB.Yaa mice. J. IMMUNOL. 2013; 191(9):4581-4588.

51. Kimura A, Kishimoto T. IL-6: regulator of Treg/Th17 balance. EUR. J. IMMUNOL. 2010; 40(7): 1830-1835.

52. Bettelli E, Carrier Y, Gao W et al. Reciprocal developmental pathways for the generation of pathogenic effector TH17 and regulatory T cells. NATURE. 2006; 441(7090): 235-238.

53. Chen W, Jin W, Hardegen N et al. Conversion of peripheral CD4+. J. EXP. MED. 2003; 198(12): 1875-1886.

54. Dominitzki S, Fantini M C, Neufert C et al. Cutting edge: trans-signaling via the soluble IL-6R abrogates the induction of FoxP3 in naive CD4+CD25 T cells. J. IMMUNOL 2007; 179(4):2041-2045.

55. Fantini M C, Becker C, Monteleone G et al. Cutting edge: TGF-beta induces a regulatory phenotype in CD4+. J. IMMUNOL. 2004; 172(9):5149-5153.

56. Veldhoen M, Hocking R J, Atkins C J et al. TGFbeta in the context of an inflammatory cytokine milieu supports de novo differentiation of IL-17-producing T cells. IMMUNITY. 2006; 24(2):179-189.

57. Fujimoto M, Nakano M, Terabe F et al. The influence of excessive IL-6 production in vivo on the development and function of Foxp3+ regulatory T cells. J. IMMUNOL. 2011; 186(1):32-40.

58. Carrade D D, Lame M W, Kent M S et al. Comparative Analysis of the Immunomodulatory Properties of Equine Adult-Derived Mesenchymal Stem Cells( ). CELL MED. 2012; 4(1):1-11.

59. Kol A, Foutouhi S, Walker N J et al. Gastrointestinal microbes interact with canine adipose derived mesenchymal stem cells in vitro and enhance immunomodulatory functions. STEM CELLS DEV. 2014.

60. Frey N V, Lazarus H M, Goldstein S C. Has allogeneic stem cell cryopreservation been given the 'cold shoulder'? An analysis of the pros and cons of using frozen versus fresh stem cell products in allogeneic stem cell transplantation. BONE MARROW. TRANSPLANT. 2006; 38(6):399-405.

61. Parody R, Caballero D, Marquez-Malaver F J et al. To freeze or not to freeze peripheral blood stem cells prior to allogeneic transplantation from matched related donors. EUR. J. HAEMATOL. 2013; 91(5):448-455.

62. Pezzanite L M, Fortier L A, Antczak D F et al. Equine allogeneic bone marrow-derived mesenchymal stromal cells elicit antibody responses in vivo. STEM. CELL RES. THER. 2015; 6(1):54.

63. Moll G, Rasmusson-Duprez I, von B L et al. Are therapeutic human mesenchymal stromal cells compatible with human blood? STEM. CELLS. 2012; 30(7):1565-1574.

64. Isakova I A, Lanclos C, Bruhn J et al. Allo-reactivity of mesenchymal stem cells in rhesus macaques is dose and haplotype dependent and limits durable cell engraftment in vivo. PLOS. ONE. 2014; 9(1):e87238.

Example 2

Administration of Allogeneic Adipose-Derived Mesenchymal Stem Cells; Use of CD8lo T Cells as a Biomarker for Monitoring Efficacy As demonstrated in Example 1, we found that autologous ASCs administered systemically resulted in complete clinical remission or substantial clinical improvement in 5 of 7 cats. All 5 cats who responded to autologous ASC therapy had decreased percentages of CD8lo cells prior to therapy (<15% CD8lo cells). 3 out of 5 cats who responded to autologous ASC therapy had increased percentages of circulating total CD8 T cells. Cats who responded to autologous ASC therapy had increased percentages of circulating total CD8 T cells and decreased percentages of CD8lo cells prior to therapy suggesting that circulating CD8+ T cells and CD8 T cell subsets may be promising biomarkers for patient selection, monitoring response to therapy and elucidating how ASCs modulate oral inflammation and decrease T cell activation.

We have further systemically administered allogenic ASCs to 7 additional cats. Of the 7 cats treated with allogeneic ASCs, all 7 had <15% CD8lo cells prior to treatment. Systemic administration of allogeneic ASCs resulted in complete clinical remission or substantial clinical improvement in 4 of the 7 cats. This improvement was correlated with systemic immune modulation and reduced inflammatory lesions.

Additionally, increased levels of CD8lo T cells over time after the initial course of therapy further appears indicative of efficacious response and is useful for monitoring therapy. Of the 4 cats positively responding to administration of allogeneic ASCs, 3 showed pronounced increases in CD8lo % over time post therapy, correlating with clinical response. The 3 non-responding cats did not increase their CD8lo cells at any point post therapy and, at 6 months had the same or even decreased percentages of CD8lo cells than at the outset. Only 1 out of the 4 cats who responded to allogeneic ASC therapy had an increased percentage of circulating CD8 T cells. In contrast, 2 of the 3 non-responders had increased percentages of circulating CD8 T cells. In summary, if the percentage of CD8lo cells are increased/induced post therapy (after one or more administrations of MSCs), e.g., at the third or sixth month check, at least about 85% of those cats go on to respond. Only one cat in the autologous study and one cat in the allogenic study responded to treatment in the absence of increased percentages of CD8lo cells over time. None of the 3 non-responding cats who received allogeneic MSCs showed an increase in CD8lo cells at any point. The data are summarized in Table 2.

TABLE 2

| Cat number | Outcome | PRE | | 1 Month | | 3 Month | | 6 Month | | % Change from baseline | Fold change |
|---|---|---|---|---|---|---|---|---|---|---|---|
| | | % CD8 Positive | % CD8 low of CD8 pos | % CD8 Positive | % CD8 low of CD8 pos | % CD8 Positive | % CD8 low of CD8 pos | % CD8 Positive | % CD8 low of CD8 pos | | |
| 1 | Resolved | 19.0 | 14.4 | n/d | n/d | 17.0 | 21.7 | 17.1 | 23.5 | 63% | 1.5 |
| 2 | Resolved | 40.5 | 15.0 | n/d | n/d | 36.8 | 10.1 | 34.7 | 12.1 | -33% | |
| 3 | Resolved | 8.5 | 8.7 | 24.5 | 9.8 | 25.6 | 21.8 | 26.3 | 9.5 | 151% | 2.5 |
| 4 | Resolved | 3.6 | 11.4 | 16.5 | 10.4 | 30.2 | 11.6 | 29.7 | 16.1 | 41% | 1.4 |
| 5 | No cure | 29.2 | 14.9 | 14.3 | 13.1 | 29.3 | 12.6 | 18.2 | 9.4 | -15% | |
| 6 | No cure | 27.4 | 11.3 | 33.4 | 12.6 | 32.9 | 10.6 | 34.5 | 11.6 | -6% | |
| 7 | No cure | 12.9 | 9.2 | n/d | n/d | 24.6 | 9.2 | 33.0 | 6.8 | 0% | |

Example 3

Human and Feline Adipose-Derived Mesenchymal Stem Cells Have Comparable Phenotype, Immunomodulatory Functions and Transcriptome Abstract The objective of this study was to complete a comprehensive side-by-side comparison of human and feline adipose-derived mesenchymal stem cells (ASCs) with an emphasis on their immunomodulatory capacity and transcriptome. Similar to human ASCs, feline ASCs were highly proliferative at low passages and fit the minimal criteria of multipotent stem cells including a compatible surface protein phenotype, osteogenic capacity and normal karyotype. Like ASCs from all species, feline ASCs inhibited mitogen activated lymphocyte proliferation in vitro, with or without direct ASC-lymphocyte contact. Feline ASCs mimic human ASCs in their mediator secretion pattern including prostaglandin E2, indoleamine 2,3 dioxygenase, transforming growth factor beta and interleukin-6, all augmented by interferon gamma secretion by lymphocytes. The transcriptome of 3 unactivated feline ASC lines were highly similar. Functional analysis of the most highly expressed genes highlighted processes including: 1) the regulation of apoptosis, 2) cell adhesion, 3) response to oxidative stress, and 4) regulation of cell differentiation. Finally, feline ASCs had a similar gene expression profile to noninduced human. ASCs. These data will help inform clinical trials using cats with naturally occurring diseases as surrogate models for human clinical trials in the regenerative medicine.

Introduction

Naturally occurring diseases in companion animals are increasingly recognized for the important role they play in discovery about human diseases and translational medicine (19). These diseases in companion animals may better reflect the complex genetic, environmental, and physiological variation present in human diseases compared to induced diseases in laboratory animals (20). Clinical trials in academic veterinary medicine mirror that of human health care systems, and animal owners are eager to enroll in these trials (20). The selection of appropriate large animal models for preclinical testing in human stem cell trials should rely on solid comparative studies as MSCs from rodents may or may not recapitulate the immunomodulatory profile of human MSCs. For example, there are important differences between human and murine MSC secretion profiles that may dictate how predictive mouse models are for studies that focus on MSCs and innate immune cells, CD8+ T cells, and mechanism of action studies (9, 21-23).

Companion animals can serve as relevant, preclinical, surrogate, translational models for MSC therapy and contribute directly to investigational new drug applications for human clinical trials. Cats with naturally occurring diseases analogous to human conditions can provide insight into feasibility, safety, and biologic activity of novel stem cell therapies. Cats develop a variety of spontaneous inflammatory and immune-mediated diseases and stem cell therapy trials are already underway for chronic oral mucosa inflammation (24), asthma (25), and chronic enteropathy (26). For example, feline chronic gingivostomatitis has a similar phenotype, T cell activation, to the human oral inflammatory diseases, oral lichen planus, apthous stomatitis and pemphigus vulgaris (27, 28).

The objectives of this work were to delineate a comprehensive immunomodulatory profile of feline ASCs and to perform a direct side-by-side comparison of feline and human ASCs as a first step in determining how ASCs from this relevant large animal species compare to human ASCs. We found that cat ASCs largely mimic human ASCs in basic phenotype, early proliferative ability, transcriptome, secretion profile (notably DO and PGE2), and functional downregulation of activated T cell proliferation.

Materials and Methods

Tissue Samples. Human adipose tissue was obtained as discarded material from female patients undergoing a breast reduction procedure in compliance with an approved protocol (University of California, Davis (UCD) Institutional Research Board). Subcutaneous feline adipose tissue was surgically obtained from specific pathogen free (SPF) cats (n=3) and from client-owned cats (n=3) undergoing routine surgery. Fat collection was conducted according to a protocol approved by the Institutional Animal Care and Use Committee, and the Clinical Trials Review Board, UCD. All owners of client-owned cats signed an informed consent form. All cats were free of feline immune deficiency virus and feline leukemia virus infection.

Human ASC isolation and expansion. Adipose tissue (approximately 20 g) was mixed with 10 mL phosphate buffered saline (PBS) and homogenized (gentleMACS dissociator, Miltenyi Biotec, San Diego, CA, http://www.m-iltenyibiotec.com/). Samples were centrifuged at 1500 rpm for 5 mins and the cell/tissue pellet was incubated with 10 mL animal-origin-free collagenase (CLSAFA, 267 U/mL; Worthington Biochemical, Lakewood, NJ, http://www.worthington-biochem.com/) for 30 mins with gentle agitation at 37° C. Samples were centrifuged at 2000 rpm for 7 mins and cell pellets were resuspended and plated in plastic culture flasks using standard culture medium (Minimum Essential Medium α [MEMα], GE Healthcare Life Sciences HyClone Laboratories, Logan, UT, http://www.gelifesciences.com/) supplemented with 10% fetal bovine serum (FBS, Atlanta Biologicals, Flowery Branch, GA, https://www.atlantabio.com/), 1% L-glutamine and 1% penicillin/streptomycin (ThermoFisher Scientific, Gibco, Pittsburgh, PA, https://www.thermofisher.com/). After 2 days, non-adherent cells were removed by washing twice with PBS. MSCs from passages 3-4 were used for experimentation.

Feline ASC isolation and expansion. ASCs were isolated from fat and cultured exactly as previously described (24). ASCs from passages 3-4 were used for experimentation.

MSC morphology and size. Feline and human ASCs were imaged on a phase contrast microscope using bright field. To quantify cell sizes, images were taken of 5 random areas of 2 human and 2 feline ASC lines grown in T225 flasks. Twenty cells from each image were measured using ImageJ software.

Karyotype. Feline and human ASCs were karyotyped exactly as previously described (29). ASCs were plated in a 6-well plate, treated with colcemid (ThermoFisher Scientific) to arrest the mitotic cells in metaphase, lifted and prepared with serial washes and fixations for staining and microscopic analysis. Analysis included scanning all slides, counting a minimum of 20 metaphases, analysis of a minimum of 7 metaphases, and karyotyping a minimum of 2 metaphases.

ASC surface phenotype. Human and feline ASCs were incubated for 45 mins with fluorophore-conjugated antibodies including CD44, CD45, CD90, CD105, and MHCII exactly as previously described (24, 30). All human antibodies were purchased from BD Biosciences (BD Biosciences, Pharmingen, San Jose, CA, http://www.bdbiosciences.com/) and feline antibodies were purchased from the Leukocyte Antigen Biology Laboratory, UCD, unless otherwise indicated [MHC II (clone 42.3), CD18 (clone FE3 9F2), CD90 (clone CA1.4G8), CD44 (clone IM7; BioLegend, San Diego, CA, http://www.biolegend.com), and CD105 (SN6; eBioscience, SanDiego, CA, http://www.ebioscience.com). Mouse IgG-APC (MCA928; AbD Serotec, Kidlington, Oxford, UK, http://www.abdserotec.com) was used as an isotype control. All samples were run on a flow cytometer (Cytomics FC500; Beckman Coulter, Brea, CA, http://www.beckmancoulter.com). Flow cytometry data were analyzed using FlowJo flow cytometry software (Tree Star, Ashland, OR, http://company.flowjo.com).

Osteogenesis. Osteogenic assays were performed exactly as previously described (31, 32). In brief, 10,000 ASCs/cm$^2$ were cultured for 14 days with media changes every 3 days. Osteogenic medium consisted of standard culture medium supplemented with 0.2 mM ascorbic acid (Sigma-Aldrich, St. Louis, MO, http://www.sigmaaldrich.com), 0.1 µM dexamethasone (Sigma-Aldrich) and 20 mM β-glycerolphosphate. Cells were fixed with 10% vol/vol formalin solution for 15 minutes, washed once with PBS, and stained for 20 minutes with 1% wt/vol Alizarin Red S (ARS, Ricca Chemical Company, Arlington, TX, http://www.riccachemical.com/) with gentle shaking to stain for precipitated calcium (Sigma-Aldrich). Samples were then photographed.

ASC proliferation. ASCs were plated into two T25 flasks at 5,000 cells/cm$^2$. At each passage, ASC viability was determined (trypan blue exclusion dye, ThermoFisher Scientific) and ASCs were enumerated (hemocytometer). Population doubling times were calculated exactly as previously described (33). Cultures were terminated at passage 6.

Mixed leukocyte reaction (MLR). MLRs were run, with and without a transwell, to compare the ability of feline and human ASCs to inhibit activated T cell proliferation and to determine if T cell-ASC contact is necessary for inhibition of lymphocyte proliferation. Feline peripheral blood mononuclear cell (PBMC) isolation and MLRs were carried out exactly as previously described (14, 24). In brief, PBMCs were isolated from whole blood using gradient centrifugation and were co-incubated with irradiated ASCs in culture wells at a 1:5 (PBMCs:ASCs) ratio and activated with 5 mg/ml concanavalin A (ConA; Sigma-Aldrich). Cells were co-cultured for 4 days. Control wells included PBMCs alone, ASCs alone, ConA stimulated PBMCs, and PBMCs mixed with ASCs without ConA stimulation. To determine the role of contact, cells were plated in transwell dishes (Corning 0.4 µM polycarbonate membrane 24 well plate, Corning, NY https://www.corning.com/) with PBMCs in the bottom and ASCs in the insert. To determine IDO activity, the experiment was run as described however media was supplemented with L-tryptophan (Sigma-Aldrich) to a final concentration of 600 µM.

For human MLRs, PBMCs were isolated using Ficoll-Paque (GE Healthcare) according to manufacturer's instructions and MSC-PBMC co-incubation, with and without transwells, was performed exactly as previously described for feline MLRs except the medium used was aMEM (GE Healthcare Life Sciences) with 16% FBS (Atlanta Biologicals), 1% penicillin/streptomycin (ThermoFisher Scientific) and 1% Glutamax (ThermoFisher Scientific) and the PBMCs were stimulated with Leucoagglutinin (PIIA; 2.5 µg/ml).

Human and feline PBMC proliferation was measured via 5-bromo-29-deoxyuridine (BrdU) incorporation (BrdU Flow Kit; BD Biosciences) and analyzed on a flow cytometer (Cytomics FC500). Flow cytometry data were analyzed using FlowJo flow cytometry software (Tree Star).

Mediator Secretion (ELISA). Feline and human PGE2, TGFβ1, VEGF, IFN-γ, TNF-α, IL-6, IL-8 and IL-10 were measured in MLR supernatants using enzyme-linked immunosorbent assay (ELISA) kits following manufacturer's instructions. Feline analytes were measured with feline-specific or feline-validated kits (IFN-γ, TNF-α, IL-6, IL-8 and IL-10: Duosets; R&D Systems, Minneapolis, MN, http://www.mdsystems.com; TGFβ1: human DuoSet (R&D), VEGF: human QuantiKine Kit (R&D), PGE2: competitive ELISA, Enzo Life Sciences, Farmingdale, NY, http://www.enzolifesciences.com/). Human TGFβ1, VEGF, IFN-γ, TNF-α (QuantiKine), PGE2, (competitive ELISA kit), IL-6, IL-8 and IL-10 (DuoSets) were all purchased from R&D. All ELISA samples were read on a Synergy HTMulti-Mode micro plate reader with Gen5 software (Biotek, Winooski, VT, http://www.biotek.com).

IDO Assay. IDO catalyzes the conversion of tryptophan to N-formyl kynurenine, which is then catabolized to kynurenine. Kynurenine levels are directly proportional to IDO activity. Two volumes of MLR media (that had been supplemented with tryptophan) were treated with 1 volume of 30% trichloroacetic acid (Sigma-Adrich) and centrifuged. Equal parts of trichloroacetic acid-treated supernatant and Ehrlich's reagent (1% p-dimethylaminobenzaldehyde in glacial acetic acid, Sigma-Aldrich) were mixed and read at 490 nm on a microplate reader (Synergy HT Multi-Mode Gen5 software) (14).

RNA Isolation. Total RNA was isolated from primary ASC cultures using the RNeasy Mini Kit (Qiagen, Inc., Valencia, CA, https://www.qiagen.com/us/). RNA quantity and quality were assessed on a NanoDrop spectrophotometer (Thermo Scientific) and the Agilent 2100 Bioanalyzer (Agilent Technologies, Santa Clara, CA, http://www.agilent.com/home), respectively.

RNA-Seq library preparation and next generation sequencing (NGS). Whole transcriptome profiling was performed using a directional, strand-specific mRNA-Seq approach. Briefly, total RNA samples were submitted to the UC Davis Comprehensive Cancer Center's Genomics Shared Resource (GSR), and indexed RNA-Seq libraries were prepared from 200 ng total RNA using the KAPA Stranded mRNA-Seq Kit (Kapa Biosystems, Inc., Wilmington, MA, https://www.kapabiosystems.com) according to the manufacturer's standard protocol. Poly-adenylated mRNA was purified from total RNA and ribosomal RNA removed by binding to oligo (dT) beads, which was followed by RNA fragmentation by incubation at 94° C. in the presence of magnesium. Double-stranded cDNA was then generated by random-primed first-strand synthesis and subsequent second strand synthesis in the presence of dUTP for strand marking. The double-stranded cDNA was then 3'-A tailed and indexed, Illumina-compatible adapters were ligated. The libraries were then enriched by high-fidelity PCR amplification (15 cycles) with KAPA HiFi HotStart DNA Polymerase and adapter-specific primers. Subsequently, libraries were combined for multiplex sequencing on an Illumina HiSeq 4000 System (100-bp, paired-end; approximately 30 million reads/sample) (34).

Next Generation Sequencing data analysis. Image processing, base calling, quality scoring (Phred), and sample demultiplexing were executed by HiSeq Control Software with Real Time Analysis (HCS v3.3.41/RTA 2.5.2) and bcl2fastq Conversion Software (Illumina; San Diego, CA, http://www.illumina.com). FASTQ-formatted sequence data was analyzed using a standard HISAT (hierarchical indexing for spliced alignment of transcripts)-Cufflinks workflow. RNA-Seq sequence reads (FASTQ format) were aligned to the reference cat genome assembly (November 2014, ICGSC Felis Catus 8.0) using HISAT software (35). Gene- and transcript-level expression were comprehensively quantified with Cufflinks software (36), which performed 1) transcript assembly, 2) identification of splice variants, 3) quantification of expression as FPKM (fragments per kilobase of transcript per million mapped reads) values, and 4) normalization. Normalized FPKM values (Cuffnorm output) were utilized for downstream analysis steps. Statistical analyses and hierarchical clustering of the data were performed with GeneSpring GX software (Agilent Technologies, Inc.), and gene-annotation enrichment analysis performed with tools available from the Database for Annotation, Visualization and Integrated Discovery (DAVID v6.7) (37, 38).

Meta-analysis of the feline ASC expression data was performed with RNA-Seq data for human ASCs (NCBI GEO Accession GSE37521).39 For this, gene expression values from both datasets [feline ASCs: FPKM; human ASCs: RPKM (Reads Per Kilobase of transcript per Million mapped reads)] were separately normalized (quantile), joined on similar Gene IDs, and then baseline-transformed. Values for replicate samples were averaged, and subsequently, hierarchical clustering (similarity measure: Euclidean; linkage rule: centroid) was performed on the genes exhibiting variance across the human ASC cell types ($\geq 2\times$ fold change relative to undifferentiated ASCs).

Statistical Analyses. For all cell-based assays, normal distribution of the data was tested using the Kolmogorov and Smirnov test. For normally distributed data, a one sample Student's t-test (normalized data; lymphocyte proliferation) or paired t-test (non-normalized data) or ANOVA (>2 comparisons) was used. For feline non-normally distributed data, a Mann-Whitney-Wilcoxon test was used to determine differences in protein secretion data. Human data were analyzed using Wilcoxon matched pairs test. Human inflammatory mediators were normalized to paired lymphocyte donors before analysis was performed. A commercially available statistical software was used for all statistical analyses (GraphPad InStat version 3.06 for Windows; GraphPad, La Jolla, CA, USA). Results are presented as mean and standard error. A P value of <0.05 was considered statistically significant.

Results

Human and Feline ASCs are morphologically and phenotypically similar. The ASCs derived from feline and human adipose tissue had typical spindle-shaped, adherent morphology (FIGS. 8A and 8B). However, human ASCs were significantly larger than feline ASCs (p<0.001; FIG. 8C). Both feline and human ASCs had a normal metaphase spread and karyotype (FIGS. 8D and 8E). The surface protein expression on feline and human ASCs were compared using markers that define MSCs (1). Both feline and human ASCs were strongly positive for CD44, CD90 and CD105 and were negative for leukocyte markers [CD18 (feline) and CD45 (human)], and MHCII (FIGS. 8F and 8G) (30, 40, 41). Both feline and human ASCs were capable of osteogenic differentiation (FIGS. 8H and 8I), and have been established to be capable of chondrogenic and adipogenic differentiation as well (42). Together, these data are consistent with the conclusion that feline ASCs are karyotypically normal, meet the minimal criteria of multipotent stem cells and are smaller but otherwise morphologically and phenotypically identical to human ASCs.

Figure 9A:
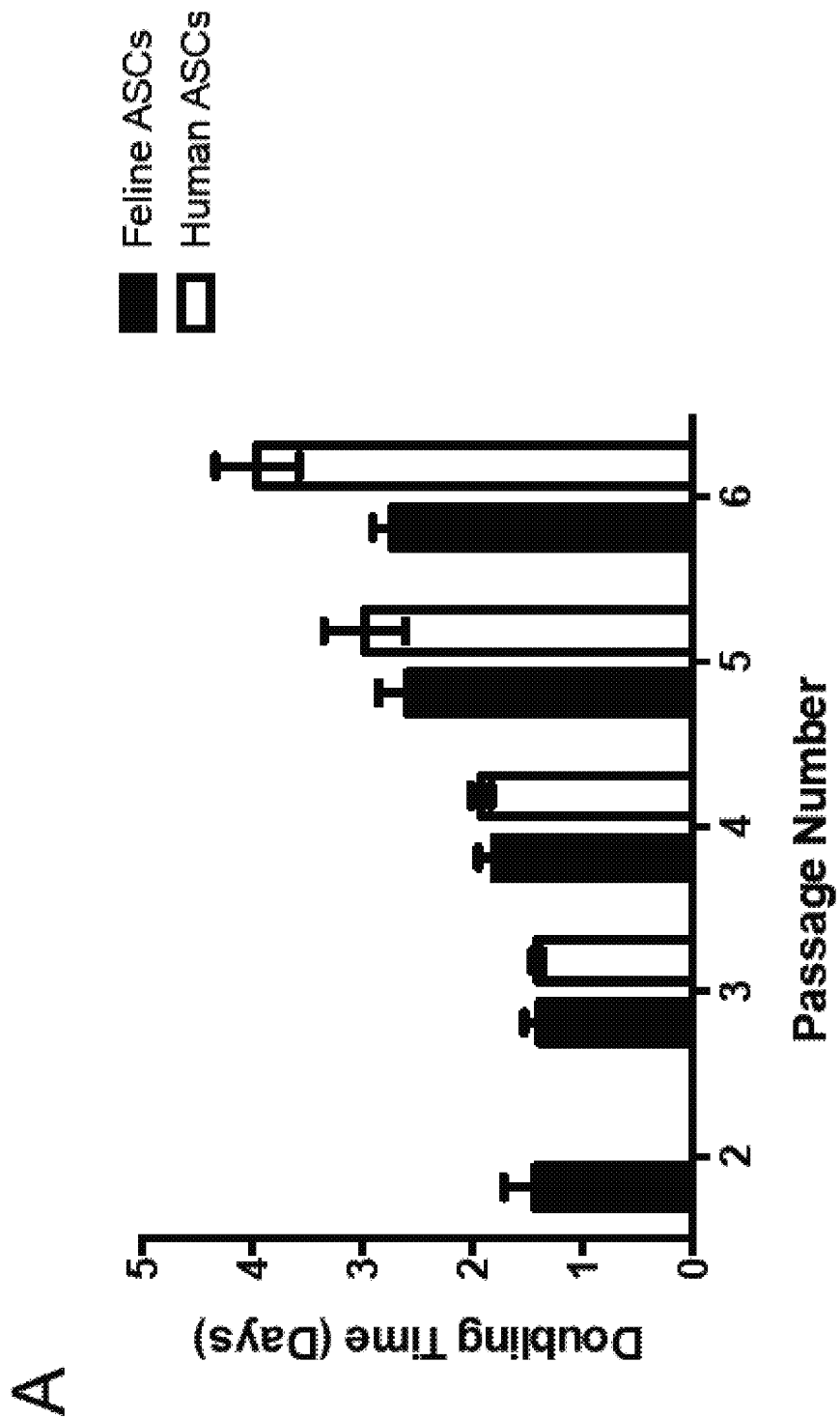

Human and Feline ASCs are highly proliferative and inhibit allogeneic activated 7' cell proliferation. Human and feline ASCs readily proliferated in culture with comparable doubling times from passage 3-6 (clinically relevant passage numbers, FIG. 9A). Previous data from our lab and others has demonstrated a significant slowing of feline ASC proliferation after passage 5 (30, 40). Human and feline ASCs significantly reduced activated T cell proliferation (p<0.004, all conditions compared to positive control, FIGS. 9B and 9C). This inhibition occurred with or without ASC-T cell contact. However, human ASCs, when in direct contact with activated T cells, did more potently reduce activated T cell proliferation as compared to human ASCs plated in transwells (p=0.03, FIG. 9C). These findings are consistent with the conclusion that feline ASCs, like other species, are potent modulators of activated T cell proliferation and that this modulation is largely mediated by secreted factors. Interestingly, human ASCs also markedly decrease activated T cell proliferation, but this regulation is stronger when ASCs are in direct contact with T cells.

Activated human and feline ASCS secrete high concentrations of immunomodulatory mediators. ASCs function in a large part via the secretion of mediators that regulate cells of the cellular and humoral immune system. We measured a number of mediators implicated in the immunomodulatory function of ASCs in parallel feline and human assays, with and without activation, and with or without cell-cell contact, to define feline ASCs and dissect out similarities and dissimilarities between cat and human ASCs. ASCs of both species variably secrete very low concentrations of IDO, PGE2, IL6 and VEGF at baseline in culture, or in the context of allogeneic PBMCs; however, ASCs in the context of mitogen-activated T cells secrete significantly higher concentrations of immunomodulatory mediators. Activated feline ASCs secrete high concentrations of EDO (FIG. 10A) similar to canine and human MSCs (FIG. 10B) but unlike murine MSCs (21). Activated feline ASCs also secrete high concentrations of PGE2 (FIG. 10C) that, unlike human ASCs (FIG. 10D), is significantly augmented by ASC-T cell contact. Activated feline and human ASCs secrete high concentrations of IL6 (FIG. 10E, 10F) and VEGF (FIG. 10G, 10H), with or without MSC-T cell contact. Human ASC secretion of VEGF was not enhanced by T cell activation (FIG. 10H) suggesting that, in humans, this growth factor is constitutively expressed and that co-incubation with activated T cells is not a primary regulator of VEGF expression.

We measured 2 mediators, IL8 and TGFβ, that are potentially secreted by both activated PBMCs and ASCs (FIG. 11). For both feline and human cells, more IL8 is present in activated ASC-PBMC co-cultures than is present in cultures with ASCs alone (FIGS. 11A and 11B, human ASCs trend, p=0.08) regardless of cell-cell contact. However, contact significantly increased IL8 secretion for human cultures and there was a similar trend for feline cultures as well (p=0.12). Feline TGFβ secretion mimicked our findings for human ASCs. Regardless of species, TGFβ was secreted by activated PBMCs, by ASCs at baseline, and in the context of ASC-PBMC co-incubation, with or without activation and with or without contact (FIGS. 11C and 11D). The concentrations varied between conditions however there was no condition which significantly altered TGFβ secretion. Findings agree with previous data from horses, humans and dogs in which TGFβ is constitutively secreted and not, by definition, upregulated by activation (14, 43, 44).

Activation of PBMCs results in the secretion of IFNγ, TNFα, and IL10, however, neither feline nor human MSCs secreted these mediators (FIG. 12). Typically, the inhibition of lymphocyte proliferation is associated with decreased IFNγ and TNFα production and variable IL10 secretion.

Unlike human ASCs, feline ASCs only inhibited IFNγ secretion in the absence of direct MSC-T cell contact whereas when ASCs were in contact with T cells, IFNγ was not inhibited. Conversely, human ASCs were capable of inhibiting IFNγ secretion when ASCs and T cells were in direct contact however, in the absence of contact, ASCs were not able to inhibit IFNγ (FIGS. 12A and 12B). Both feline and human ASCs inhibited TNFα secretion however feline ASCs were more able to inhibit TNFα, like IFNγ, when ASCs were not in direct contact with T cells (FIGS. 12C and 12D). IL10 is a regulatory, generally anti-inflammatory, mediator whose secretion by PBMCs can be augmented by MSCs. Activated feline ASCs did increase PBMC secretion of IL10 however activated human ASCs did not alter IL10 secretion regardless of cell-cell contact (FIGS. 12E and 12F).

These data suggest that there are multiple different mechanisms by which human and feline ASCs regulate inflammatory (most notably IFNγ) and regulatory mediator secretion by activated PBMCs, one dependent on cell contact and one primarily mediated by soluble factors. Deciphering these mechanisms is critical as although both cell-cell contact and soluble mediator production are likely important in vivo, there is at least one condition under which IFNγ secretion is not decreased. Sustained secretion of IFNγ may have important implications for particular clinical applications as IFNγ stimulates MSCs, derived from a number of tissues, to produce IDO, TGFβ, and HGF, to increase cell-cell signaling via the upregulation of PD-L1 and ICAM-1 and to generate regulatory CD8+ T cells (21, 45-50). These data are in agreement with data from our in vivo study where 2 cats with severe, chronic, oral inflammation that fully responded to ASC therapy (complete, sustained disease resolution) did so in the context of high serum concentrations of IFNγ (24).

Transcriptome analysis of feline ASCs demonstrates their relatedness and insight into their biological properties. Having defined and compared the biological features of feline ASCs, transcriptome analysis was next performed in order to evaluate the relatedness of the feline ASCs to each other, as well as to human ASCs, and to gain insight into the functional implications of the ASC gene expression profile. Towards this goal, RNA-Seq analysis was performed on total mRNA prepared from 3 separate feline non-induced ASC culture preparations (p3), followed by data analysis with a standard HISAT-Cufflinks pipeline to yield gene expression values expressed as FPKM (35). Pair-wise correlation analyses of the gene-level expression data (i.e., FPKM) for each ASC culture demonstrated that there was a high level of similarity between the ASC preparations isolated from the 3 cats (Pearson r=0.853, 0.891, 0.974). There was a significant overlap of genes (2,743 genes, 89.00-90.47%) that exhibited at least a moderate level of expression (i.e., ≥15 FPKM) in each ASC preparation. Significant overlap of gene expression profiles from the 3 feline ASC lines was highly expressed in 401 genes (≥100 FPKM). In order to gain insight into the functional significance of the ASC expression repertoire, functional annotation analysis was performed on the most highly expressed genes (i.e., ≥100 FPKM; 401 genes) that were common to all ASCs, with the notion that this would highlight the most prominent processes. For this, the gene set was analyzed with tools available from DAVID Bioinformatics Resources 6.7, that evaluate gene-gene functional relationships and enrichment for biological "modules" (37, 38). There was over-representation of gene ontology categories involved in a number of processes, including 1) the regulation of apoptosis, 2) cell adhesion, 3) response to oxidative stress, 4) regulation of cell differentiation, and 5) various metabolic processes, including phosphate metabolism, sterol metabolism, and oxidative phosphorylation.

Finally, the potential similarity of feline ASCs to their human counterparts was investigated by performing meta-analysis with an RNA-Seq dataset from human ASCs that were either undifferentiated (non-induced) or induced to differentiate along the adipogenic, osteogenic, and chondrogenic lineages (NCBI GEO Accession GSE37521 (39). Genes exhibiting variance across the human ASC cell types (≥2×fold change relative to undifferentiated ASCs) were determined and then used as the basis for hierarchical clustering with the feline ASCs. The feline ASCs clustered closely with the undifferentiated human ASCs, demonstrating their similar patterns of gene expression to the human ASCs, and providing additional evidence that the feline ASCs are representative of undifferentiated phenotype.

Discussion

Clinical trials with cell therapies are increasingly taking advantage of companion animals with naturally occurring diseases as relevant, surrogate models to support novel human investigational drug applications (IND) and veterinary investigational new animal drug applications (INAD) (19, 20, 51, 52). Cats are a particularly important translational model for a number of diseases that are similar in cats and humans, including FIV (HIV) (53), T cell mediated oral mucosa inflammation (24), chronic renal failure (54), asthma (25), chronic enteropathy (26) and osteoarthritis. The goal of this work was to profile feline ASCs and directly compare their phenotypic, cellular and immunomodulatory profiles with human ASCs to deepen our understanding of MSC-based therapies as we move towards mechanism of action studies in animals and people. We found that feline ASCs, like human ASCs, can be defined as MSCs based on defined criteria (surface phenotype, differentiation potential, morphology, doubling time, normal karyotype) and that their transcriptome clusters with un-induced (un-differentiated) human ASCs. Feline ASCs inhibit activated T cell proliferation and their profile of secreted immunomodulatory mediators closely mimics that of human ASCs, dominated by IDO, PGE2, TGFβ, IL6 and IL8. Feline ASCs are highly activated and functional in the presence of the pro-inflammatory cytokines, IFNγ and TNFα, and, like human6 and canine ASCs (12), their regulation of IFNγ is complex and likely dictated by at least 2 mechanisms, depending on whether or not the ASCs are in direct contact with activated PBMCs.

The data we generated from human ASCs largely mimicked data from studies that either compared human ASCs with MSCs from other sources, especially bone marrow, or studies that determined the immunomodulatory phenotype of human ASCs. Similar to others, we found that ASCs were able to inhibit activated T cell proliferation with or without direct ASC-T cell contact (48, 55) however we also found that this inhibition was more marked when ASCs were in contact with activated cells. MSC-immune cell contact, especially in the context of both IFNγ and TNFα, has been shown to upregulate PD-1, VCAM-1 and ICAM-1 and this contact can then augment the production of soluble mediators, notably IDO (7, 21, 50). Our data are also aligned with data from fetal membrane, or decidual, MSCs that also inhibit lymphocyte proliferation more profoundly in the presence of MSC-immune cell contact (49, 50). Contact dependent inhibition of immune cell function is thought to be more important for local immunosuppression (49). In the absence of cell-cell contact, human ASCs were unable to inhibit IFNγ secretion and IL8 production was decreased.

Unlike human and other veterinary species studied to date (11, 33), feline ASCs expanded in standard culture conditions, do not proliferate robustly in vitro after passage 5 or 6 (30, 42). This is in spite of the fact that, similar to horses (33) and humans (56), adipose tissue is still the tissue of choice for feline MSC therapy due to ease of collection, tissue abundance and faster growth kinetics (41). The most likely consideration for this poor, late passage proliferation is inadequate cell culture condition optimization. This phenomenon is independent of feline foamy virus (FFV) infection as it occurs in ASC lines from specific pathogen free (SPF) cats as well as client-owned cats free of FFV infection (30). Our group has not investigated cell culture optimization with media supplementation of growth factors, increased FBS concentration, or cytokine supplementation however optimization would likely improve growth kinetics. Creating working cell banks of autologous or allogeneic ASCs at PI and expanding to doses of $5 \times 10^6$ cells/kg (P2 or P3) for clinical use is readily achieved given the high number of ASCs obtained from small feline fat samples even without culture optimization.

Mesenchymal stem cells derived from different tissues can vary substantially in size, for example, equine cord blood derived MSCs are much larger than equine ASCs (57). In this study, we found that ASCs in humans and cats differ in size, with feline ASCs being much smaller than human ASCs. Cell size differences are likely to be irrelevant for basic biological functions however recognizing cell size differences may inform species specific tissue engineering protocols and scaffold features (58). MSC size has also been implicated in determining pulmonary entrapment after intravascular cell administration (59).

The key mediators secreted by human and feline ASCs were similar. We did not attempt to compare absolute concentrations of secreted mediators as the mitogens selected (ConA and PHA) were different and both are non-specific. Mitogen selection and concentration was based on our early data examining proliferation kinetics and degree of activation as well as other published data in cats and humans. Regardless, a few patterns are of interest. TGF-β1, VEGF and, to a lesser extent, PGE2 were the only mediators secreted to a measurable level by feline and human ASCs at baseline with no activation. The constitutive secretion of TGFβ1 concurs with previous findings in human (6, 7), equine (14) and canine (12) ASCs. TGFβ1 is involved in immune regulation by and differentiation of Foxp3+ regulatory T cells and Th17 cells and may play in important part in MSC immunomodulation although it is not involved in the inhibition of lymphocyte proliferation (7, 12, 60). Interestingly, VEGF secretion was not increased after mitogen stimulation in human ASCs however VEGF secretion did increase after feline ASC activation. It may be that VEGF secretion in human ASCs is more sensitive to hypoxic signals rather than T cell mitogens (61).

Our findings suggest that un-induced feline ASCs are highly similar to human ASCs in their basic morphology, phenotype and transcriptome. Activation of feline ASCs potentiates the secretion of a panel of immunomodulatory mediators that is comparable to human ASCs and human fetal decidual stem cells with one end result of decreasing lymphocyte proliferation. These data provide additional rationale for the use of naturally occurring diseases in cats as appropriate surrogate models for human regenerative medicine trials with MSCs when the diseases are also shown to be comparable. These data also provide the first published immunomodulatory (secretion) and transcriptome profile of feline ASCs from which further mechanism of action studies can result.

CONCLUSION

These data provide the first comprehensive side-by-side evaluation of human and feline ASCs including phenotype, immunomodulatory profile and transcriptome. Findings suggest that feline ASCs are multipotent mesenchymal stem cells that, when activated by IFNγ, modulate lymphocyte proliferation using soluble mediators that mirror human ASC secretion pattern. Transcriptome analysis revealed similar gene expression profiles to uninduced human ASCs and set the stage for deeper investigations using cats as surrogate models for human cell therapy based clinical trials.

REFERENCES FOR EXAMPLE 3

1. Dominici M, Le Blanc K, Mueller I et al. Minimal criteria for defining multipotent mesenchymal stromal cells. The International Society for Cellular Therapy position statement. Cytotherapy 2006; 8: 315-317.
2. Gimble J M, Katz A J, Bunnell B A. Adipose-derived stem cells for regenerative medicine. Circ Res 2007; 100: 1249-1260.
3. Ivanova-Todorova E, Bochev I, Mourdjeva M et al. Adipose tissue-derived mesenchymal stem cells are more potent suppressors of dendritic cells differentiation compared to bone marrow-derived mesenchymal stem cells. Immunol Lett 2009; 126: 37-42.
4. Jansen B J H, Gilissen C, Roelofs H et al. Functional Differences Between Mesenchymal Stem Cell Populations Are Reflected by Their Transcriptome. Stem Cells and Development 2009; 19: 481-490.
5. Keyser K A, Beagles K E, Kiem H P. Comparison of mesenchymal stem cells from different tissues to suppress T-cell activation. Cell transplantation 2007; 16: 555-562.
6. Melief S M, Zwaginga J J, Fibbe W E et al. Adipose tissue-derived multipotent stromal cells have a higher immunomodulatory capacity than their bone marrow-derived counterparts. Stem cells translational medicine 2013; 2: 455-463
7. Yoo K H, Jang I K, Lee M W et al. Comparison of immunomodulatory properties of mesenchymal stem cells derived from adult human tissues. Cellular immunology 2009; 259: 150-156.
8. Glenn J D, Whartenby K A. Mesenchymal stem cells: Emerging mechanisms of immunomodulation and therapy. World J Stem Cells 2014; 6: 526-539.
9. Le Blanc K, Davies L C. Mesenchymal stromal cells and the innate immune response. Immunol Lett 2015;
10. Carrade D D, Borjesson D L. Immunomodulation by mesenchymal stem cells in veterinary species. Comparative medicine 2013; 63: 207-217.
11. Clark K C, Kol A, Shahbenderian S et al. Canine and Equine Mesenchymal Stem Cells Grown in Serum Free Media Have Altered Immunophenotype. Stem cell reviews 2016; 12: 245-256.
12. Kang J W, Kang K S, Koo H C et al. Soluble factors-mediated immunomodulatory effects of canine adipose tissue-derived mesenchymal stem cells. Stem Cells Dev 2008; 17: 681-693.
13. Kol A, Foutouhi S, Walker N J et al. Gastrointestinal microbes interact with canine adipose-derived mesenchymal stem cells in vitro and enhance immunomodulatory functions. Stem Cells Dev 2014; 23: 1831-1843, 14. Carrade D D, Lame M W, Kent M S et al. Comparative Analysis of the Immunomodulatory Properties of Equine Adult-Derived Mesenchymal Stem Cells( ). Cell Med 2012; 4: 1-11.
15. Cahill E F, Sax T, Hartmann I et al. Mesenchymal stromal cells protect endothelial cells from cytotoxic T lymphocyte induced lysis. Scandinavian journal of immunology 2016;
16. Ciccocioppo R, Cangemi G C, Kruzliak P et al. Ex vivo immunosuppressive effects of mesenchymal stem cells on Crohn's disease mucosal T cells are largely dependent on indoleamine 2,3-dioxygenase activity and cell-cell contact. Stem cell research & therapy 2015; 6: 137.
17. Franquesa M, Mensah F K, Huizinga R et al. Human adipose tissue-derived mesenchymal stem cells abrogate plasmablast formation and induce regulatory B cells independently of T helper cells. Stem cells (Dayton, Ohio) 2015; 33: 880-891.
18. Galipeau J, Krampera M, Barrett J et al. International Society for Cellular Therapy perspective on immune functional assays for mesenchymal stromal cells as potency release criterion for advanced phase clinical trials. Cytotherapy 2016; 18: 151-159.
19. Lairmore M D, Khanna C. Naturally Occurring Diseases in Animals: Contributions to Translational Medicine. ILAR Journal 2014; 55: 1-3.
20. Kol A, Arzi B, Athanasiou K A et al. Companion animals: Translational scientist's new best friends. Science translational medicine 2015; 7: 308ps321.
21. Ren G, Su J, Zhang L et al. Species variation in the mechanisms of mesenchymal stem cell-mediated immunosuppression. Stem cells (Dayton, Ohio) 2009; 27: 1954-1962.
22. Strioga M, Pasukoniene V, Characiejus D. CD8+ CD28− and CD8+ CD57+ T cells and their role in health and disease. Immunology 2011; 134: 17-32.
23. Vallejo A N. CD28 extinction in human T cells: altered functions and the program of T-cell senescence. Immunol Rev 2005; 205: 158-169.
24. Arzi B, Mills-Ko E, Verstraete F J et al. Therapeutic Efficacy of Fresh, Autologous Mesenchymal Stem Cells for Severe Refractory Gingivostomatitis in Cats. Stem cells translational medicine 2016; 5: 75-86.
25. Trzil J E, Masseau I, Webb T L et al. Intravenous adipose-derived mesenchymal stem cell therapy for the treatment of feline asthma: a pilot study. Journal of feline medicine and surgery 2015;
26. Webb T L, Webb C B. Stem cell therapy in cats with chronic enteropathy: a proof-of-concept study. Journal of feline medicine and surgery 2015; 17: 901-908.
27. Bascones-Martinez A, Garcia-Garcia V, Meurman J H et al. Immune-mediated diseases: what can be found in the oral cavity? Int J Dermatol 2015; 54: 258-270.
28. Harley R, Gruffydd-Jones T J, Day M J. Immunohistochemical characterization of oral mucosal lesions in cats with chronic gingivostomatitis. J Comp Pathol 2011; 144: 239-250.
29. Cary W A, Hori C N, Pham M T et al. Efficient Generation of Induced Pluripotent Stem and Neural Progenitor Cells From Acutely Harvested Dura Mater Obtained During Ventriculoperitoneal Shunt Surgery. World Neurosurgery 2015; 84: 1256-1266.e1251.
30. Arzi B, Kot A, Murphy B et al. Feline foamy virus adversely affects feline mesenchymal stem cell culture and expansion: implications for animal model development. Stem Cells Dev 2015; 24: 814-823.
31. Beegle J, Lakatos K, Kalomoiris S et al. Hypoxic preconditioning of mesenchymal stromal cells induces metabolic changes, enhances survival, and promotes cell retention in vivo. Stem cells (Dayton, Ohio) 2015; 33: 1818-1828.
32. Martin D R, Cox N R, Hathcock T L et al. Isolation and characterization of multipotential mesenchymal stem cells from feline bone marrow. Experimental hematology 2002; 30: 879-886.
33. Vidal M A, Walker N J, Napoli E et al. Evaluation of senescence in mesenchymal stem cells isolated from equine bone marrow, adipose tissue, and umbilical cord tissue. Stem Cells Dev 2012; 21: 273-283.
34. Bentley D R, Balasubramanian S, Swerdlow H P et al. Accurate whole human genome sequencing using reversible terminator chemistry. Nature 2008; 456: 53-59.
35. Kim D, Langmead B, Salzberg S L. HISAT: a fast spliced aligner with low memory requirements. Nature methods 2015; 12: 357-360.
36. Trapnell C, Williams B A, Pertea G et al. Transcript assembly and quantification by RNA-Seq reveals unannotated transcripts and isoform switching during cell differentiation. Nature biotechnology 2010; 28: 511-515.
37. Huang da W, Sherman B T, Lempicki R A. Systematic and integrative analysis of large gene lists using DAVID bioinformatics resources. Nature protocols 2009; 4: 44-57.
38. Huang da W, Sherman B T, Lempicki R A. Bioinformatics enrichment tools: paths toward the comprehensive functional analysis of large gene lists. Nucleic acids research 2009; 37: 1-13.
39. Jaager K, Islam S, Zajac P et al. RNA-Seq Analysis Reveals Different Dynamics of Differentiation of Human Dermis- and Adipose-Derived Stromal Stem Cells. PLoS ONE 2012; 7: e38833.
40. Kim H R, Lee J, Byeon J S et al. Extensive characterization of feline intra-abdominal adipose-derived mesenchymal stem cells. Journal of veterinary science 2016;
41. Webb T L, Quimby J M, Dow S W. In vitro comparison of feline bone marrow-derived and adipose tissue-derived mesenchymal stem cells. Journal of feline medicine and surgery 2012; 14: 165-168.
42. Kono S, Kazama T, Kano K et al. Phenotypic and functional properties of feline dedifferentiated fat cells and adipose-derived stem cells. Veterinary journal (London, England: 1997) 2014; 199: 88-96.
43. Groh M E, Maitra B, Szekely E et al. Human mesenchymal stem cells require monocyte-mediated activation to suppress alloreactive T cells. Experimental hematology 2005; 33: 928-934.
44. Screven R, Kenyon E, Myers M J et al. Immunophenotype and gene expression profile of mesenchymal stem cells derived from canine adipose tissue and bone marrow. Veterinary immunology and immunopathology 2014; 161: 21-31.
45. Myers L, Croft M, Kwon B S et al. Peptide-specific CD8 T regulatory cells use IFN-gamma to elaborate TGF-beta-based suppression. J Immunol 2005; 174: 7625-7632.
46. Niederkorn J Y. Emerging concepts in CD8+ T regulatory cells. Current Opinion in Immunology 2008; 20: 327-331.
47. Ryan J M, Barry F, Murphy J M et al. Interferon-gamma does not break, but promotes the immunosuppressive capacity of adult human mesenchymal stem cells. Clinical and experimental immunology 2007; 149: 353-363.
48. Krampera M, Cosmi L, Angeli R et al. Role for interferon-gamma in the immunomodulatory activity of human bone marrow mesenchymal stem cells. Stem cells (Dayton, Ohio) 2006; 24: 386-398.
49. Erkers T, Nava S, Yosef J et al. Decidual stromal cells promote regulatory T cells and suppress alloreactivity in a cell contact-dependent manner. Stem Cells Dev 2013; 22: 2596-2605.
50. Karlsson H, Erkers T, Nava S et al. Stromal cells from term fetal membrane are highly suppressive in allogeneic settings in vitro. Clinical and experimental immunology 2012; 167: 543-555.
51. Grimm D. From bark to bedside. Science (New York, N.Y.) 2016; 353: 638-640.
52. Hoffman A M, Dow S W. Concise Review: Stem Cell Trials Using Companion Animal Disease Models. Stem cells (Dayton, Ohio) 2016; 34: 1709-1729.
53. Miller M M, Fogle J E, Ross P et al. Feline glycoprotein A repetitions predominant anchors transforming growth factor beta on the surface of activated CD4(+)CD25(+) regulatory T cells and mediates AIDS lentivirus-induced T cell immunodeficiency. AIDS Res Hum Retrovi ruses 2013; 29: 641-651.
54. Quimby J M, Webb T L, Randall E et al. Assessment of intravenous adipose-derived allogeneic mesenchymal stem cells for the treatment of feline chronic kidney disease: a randomized, placebo-controlled clinical trial in eight cats. Journal of feline medicine and surgery 2016; 18: 165-171.
55. Rasmusson I, Ringden O, Sundberg B et al. Mesenchymal stem cells inhibit the formation of cytotoxic T lymphocytes, but not activated cytotoxic T lymphocytes or natural killer cells. Transplantation 2003; 76: 1208-1213.
56. Kern S, Eichler H, Stoeve J et al. Comparative analysis of mesenchymal stem cells from bone marrow, umbilical cord blood, or adipose tissue. Stem cells (Dayton, Ohio) 2006; 24: 1294-1301.
57. Toupadakis C A, Wong A, Genetos D C et al. Comparison of the osteogenic potential of equine mesenchymal stem cells from bone marrow, adipose tissue, umbilical cord blood, and umbilical cord tissue. American journal of veterinary research 2010; 71: 1237-1245.
58. Di Luca A, Ostrowska B, Lorenzo-Moldero I et al. Gradients in pore size enhance the osteogenic differentiation of human mesenchymal stromal cells in three-dimensional scaffolds. Scientific reports 2016; 6: 22898.
59. Campbell N G, Kaneko M, Shintani Y et al. Cell Size Critically Determines Initial Retention of Bone Marrow Mononuclear Cells in the Heart after Intracoronary Injection: Evidence from a Rat Model. PLoS One 2016; 11: e0158232.
60. Carrade Holt D D, Wood J A, Granick J L et al. Equine mesenchymal stem cells inhibit T cell proliferation through different mechanisms depending on tissue source. Stem Cells Dev 2014; 23: 1258-1265.
61. Lakatos K, Kalomoiris S, Merkely B et al. Mesenchymal Stem Cells Respond to Hypoxia by Increasing Diacylglycerols. Journal of cellular biochemistry 2016; 117: 300-307.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating gingivostomatitis in a feline in need thereof, comprising:
    a) measuring the level of CD8lo T cells in a biological sample from the feline, wherein the biological sample comprises CD8+ T cells;
    b) identifying a level of CD8lo T cells in the biological sample that is below a threshold level of 15% CD8lo T cells of total CD8+ T cells, wherein a threshold level below 15% indicates a responsiveness to administered mesenchymal stem cells (MSCs);
    c) selecting a feline with a CD8lo T cells level below 15%;
    d) isolating MSCs from adipose tissue obtained from the feline of step (c), thereby obtaining adipose-derived mesenchymal stem cells (AdMSCs); and
    e) administering to the feline in need thereof an effective amount of the AdMSCs to treat feline gingivostomatitis.

2. The method of claim 1, wherein the CD8lo T cells express cell surface CD57.

3. The method of claim 1, wherein the MSCs are positive for CD44+, CD90+ and CD105+ and negative for CD34−, CD45− and MHC class II−.

4. The method of claim 1, wherein the feline has a CD4/CD8 ratio in blood that is less than 1.0 prior to administration of the MSCs and a CD4/CD8 ratio in blood that is greater than 1.3 after one or more administrations of the MSCs.

* * * * *